(12) United States Patent
Shioda et al.

(10) Patent No.: US 8,221,304 B2
(45) Date of Patent: Jul. 17, 2012

(54) OPERATION MICROSCOPE

(75) Inventors: Keiji Shioda, Hachioji (JP); Kazuhito Nakanishi, Hachioji (JP); Masakazu Mizoguchi, Tsukui-gun (JP); Takashi Fukaya, Tama (JP); Wataru Ohno, Hachioji (JP); Masahiko Kinukawa, Sagamihara (JP); Masaaki Ueda, Sagamihara (JP); Motokazu Nakamura, Hino (JP); Toru Shinmura, Hachioji (JP); Kazuo Morita, Hachioji (JP)

(73) Assignee: Olympus Corporation, Tokyo (JP)

( * ) Notice: Subject to any disclaimer, the term of this patent is extended or adjusted under 35 U.S.C. 154(b) by 83 days.

(21) Appl. No.: 10/911,970

(22) Filed: Aug. 5, 2004

(65) Prior Publication Data
US 2005/0020876 A1    Jan. 27, 2005

Related U.S. Application Data

(63) Continuation of application No. 09/837,787, filed on Apr. 18, 2001, now abandoned.

(30) Foreign Application Priority Data

| Apr. 20, 2000 | (JP) | 2000-119995 |
| Jun. 15, 2000 | (JP) | 2000-180224 |
| Jun. 26, 2000 | (JP) | 2000-191476 |
| Jun. 27, 2000 | (JP) | 2000-193223 |
| Jun. 28, 2000 | (JP) | 2000-194807 |

(51) Int. Cl.
*A61B 1/00* (2006.01)

(52) U.S. Cl. ........ 600/102; 600/103; 600/111; 600/117; 600/118; 600/166; 359/368; 359/372; 348/79

(58) Field of Classification Search .................. 600/102, 600/103, 111, 117, 118, 166; 359/368, 372; 348/79
See application file for complete search history.

(56) References Cited

U.S. PATENT DOCUMENTS

| 4,958,932 A | 9/1990 | Kegelman et al. |
| 5,095,887 A | 3/1992 | Leon et al. |
| 5,098,426 A * | 3/1992 | Sklar et al. ........................ 606/5 |
| 5,339,799 A | 8/1994 | Kami et al. |
| 5,601,549 A * | 2/1997 | Miyagi ............................ 606/4 |
| 5,732,703 A | 3/1998 | Kalfas et al. |
| 5,787,760 A * | 8/1998 | Thorlakson .................... 74/512 |

(Continued)

FOREIGN PATENT DOCUMENTS

JP    58-032735    2/1983

(Continued)

OTHER PUBLICATIONS

Japanese Official Action dated Aug. 10, 2010 together with an English language translation.

(Continued)

*Primary Examiner* — Aaron Roane
(74) *Attorney, Agent, or Firm* — Scully, Scott, Murphy & Presser, P.C.

(57) ABSTRACT

There is disclosed an operation microscope in which an observing and displaying system of an operating instrument are selected, and an endoscope image for observing a dead angle of the microscope and a navigation image are selectively displayed in a microscope observation field, so that a tomographic image, three-dimensionally constructed image, and the like can be selectively displayed in a display screen in accordance with a treatment position displayed in a monitor or an observation position of the operation microscope.

4 Claims, 50 Drawing Sheets

U.S. PATENT DOCUMENTS

| | | | |
|---|---|---|---|
| 5,876,325 A | | 3/1999 | Mizuno et al. |
| 5,957,832 A | | 9/1999 | Taylor et al. |
| 5,961,456 A | * | 10/1999 | Gildenberg .................. 600/429 |
| 6,054,985 A | * | 4/2000 | Morgan et al. ................ 715/804 |
| 6,081,371 A | * | 6/2000 | Shioda et al. ................. 359/372 |
| 6,398,721 B1 | * | 6/2002 | Nakamura et al. ............ 600/102 |
| 6,539,250 B1 | * | 3/2003 | Bettinger ........................ 604/20 |

FOREIGN PATENT DOCUMENTS

| | | |
|---|---|---|
| JP | 62-073223 | 4/1987 |
| JP | 3-284254 | 12/1991 |
| JP | 5-211991 | 8/1993 |
| JP | 7-163527 | 6/1995 |
| JP | 8-10263 | 1/1996 |
| JP | 08-101354 | 4/1996 |
| JP | 8-140991 | 6/1996 |
| JP | 8-196513 | 8/1996 |
| JP | 08-201026 | 8/1996 |
| JP | 08-285541 | 11/1996 |
| JP | 9-56669 | 3/1997 |
| JP | 9-266919 | 10/1997 |
| JP | 10-333047 | 12/1998 |
| JP | 11-258514 | 9/1999 |
| JP | 2000-89123 | 3/2000 |
| JP | 2000-237118 | 9/2000 |
| JP | 2001-104335 | 4/2001 |

OTHER PUBLICATIONS

Japanese Official Action dated Dec. 8, 2009 together with an English language translation.

Japanese Official Action dated Jul. 6, 2010 together with an English language translation.

* cited by examiner

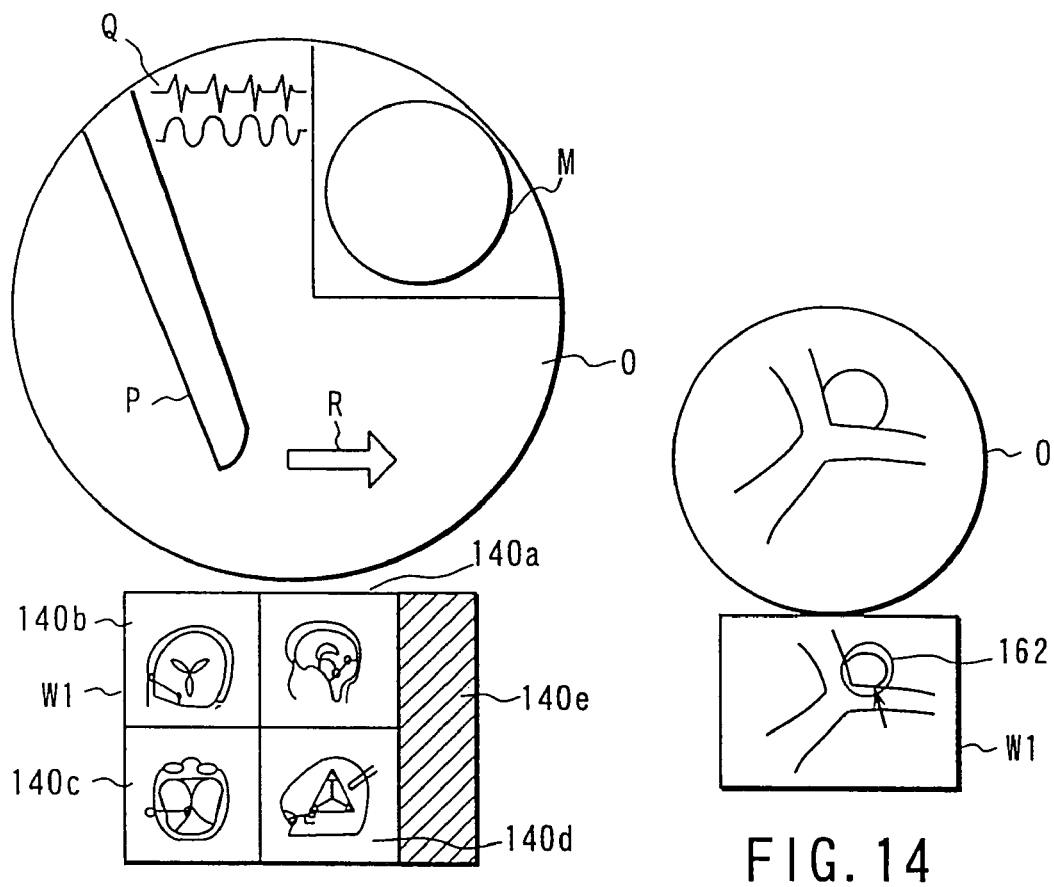
FIG. 12
FIG. 14
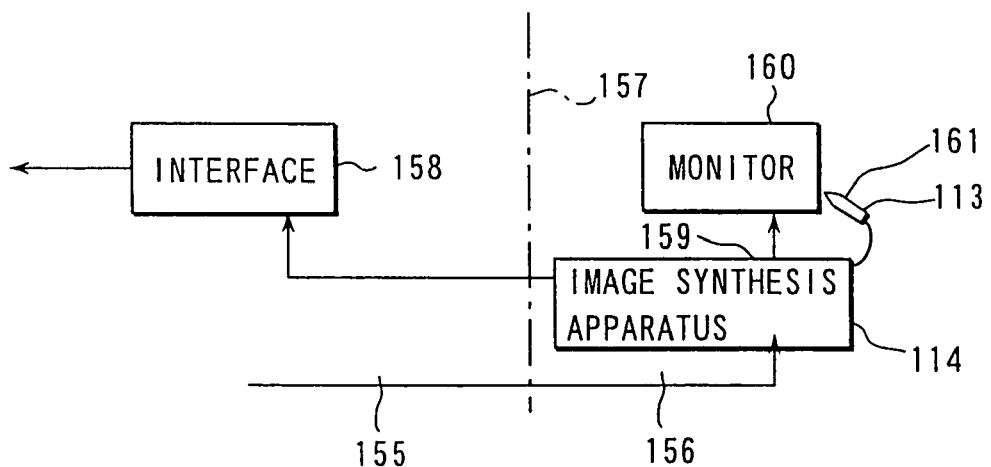
FIG. 13

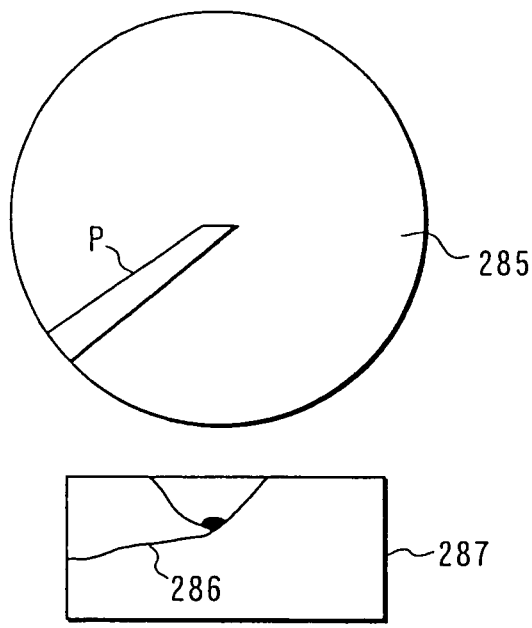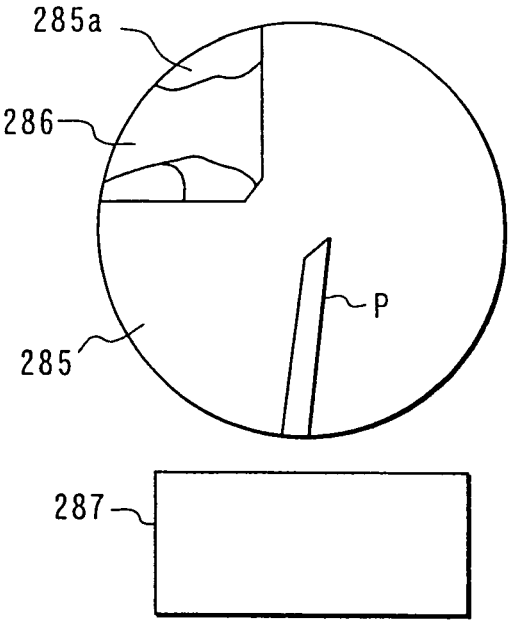
FIG. 27  FIG. 28
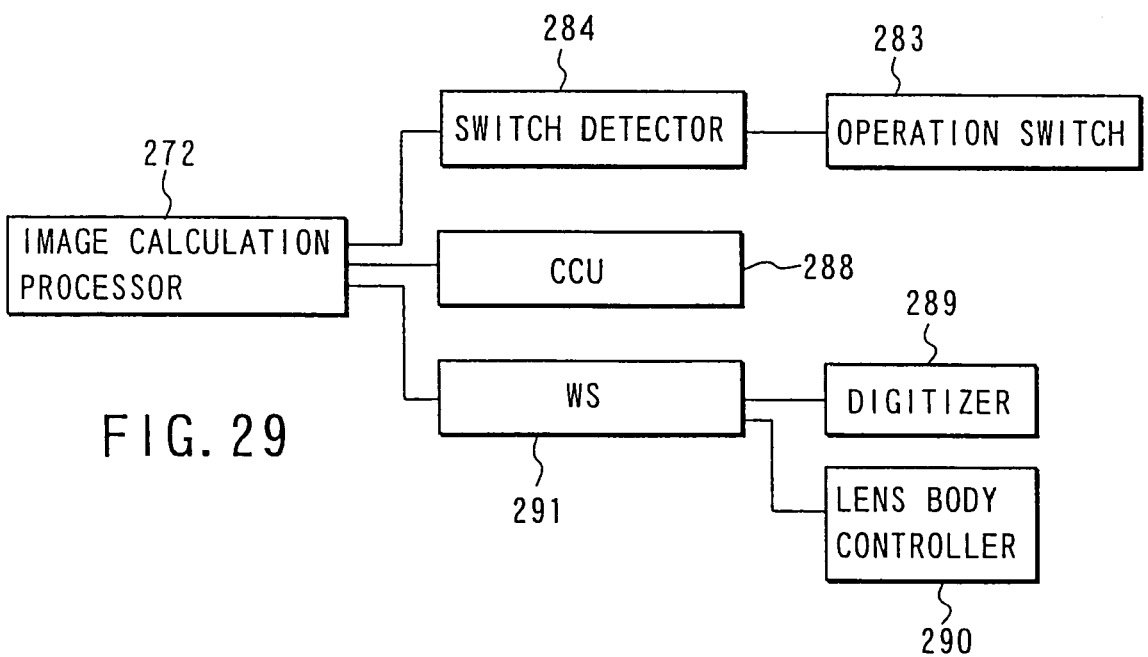
FIG. 29

| DURING ULTRASONIC OBSERVATION | → | SMALL SCREEN:PRE-OPERATIVE IMAGE (ULTRASONIC OBSERVER PLANE IMAGE) LARGE SCREEN:ULTRASONIC OBSERVATION IMAGE |

| EXCEPT FOR ULTRASONIC OBSERVATION | → | SMALL SCREEN:PRE-OPERATIVE IMAGE (ENTIRE HEAD IMAGE) LARGE SCREEN:ULTRASONIC OBSERVATION IMAGE |

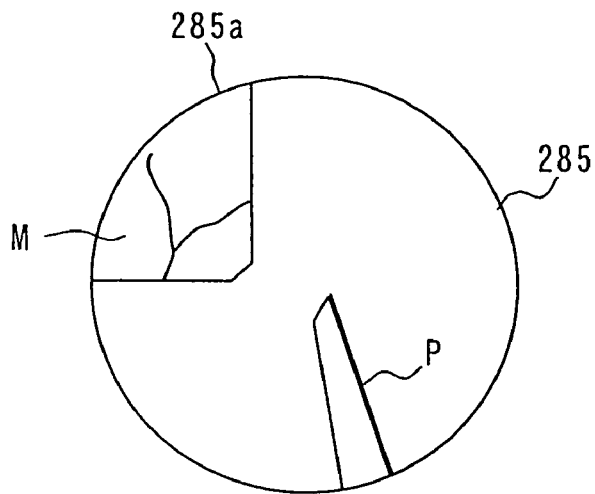
FIG. 39
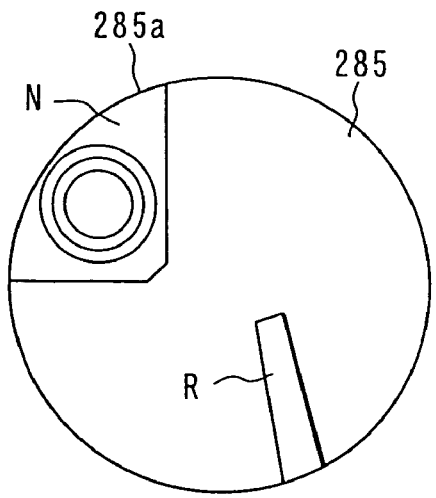
FIG. 40
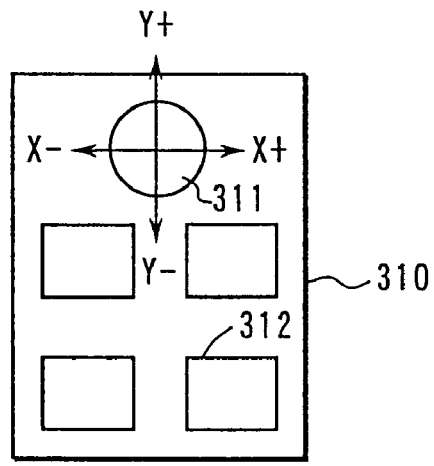
FIG. 41
WHEN ENDOSCOPE IMAGE IS
DISPLAYED IN FIELD
X+: ENDOSCOPE ZOOM-UP
X-: ENDOSCOPE ZOOM-DOWN
Y+: ENDOSCOPE LIGHT AMOUNT UP
Y-: ENDOSCOPE LIGHT AMOUNT DOWN
FIG. 42

```
WHEN ULTRASONIC IMAGE IS
DISPLAYED IN FIELD
X+:SCAN START
X-:SCAN STOP
Y+:DISPLAYED IMAGE RIGHT ROTATION
Y-:DISPLAYED IMAGE LEFT ROTATION
```
FIG. 43
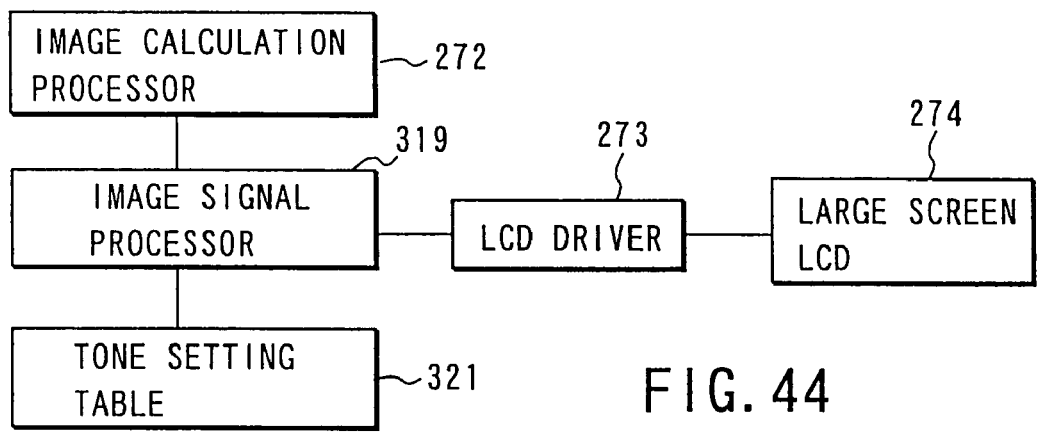
FIG. 44
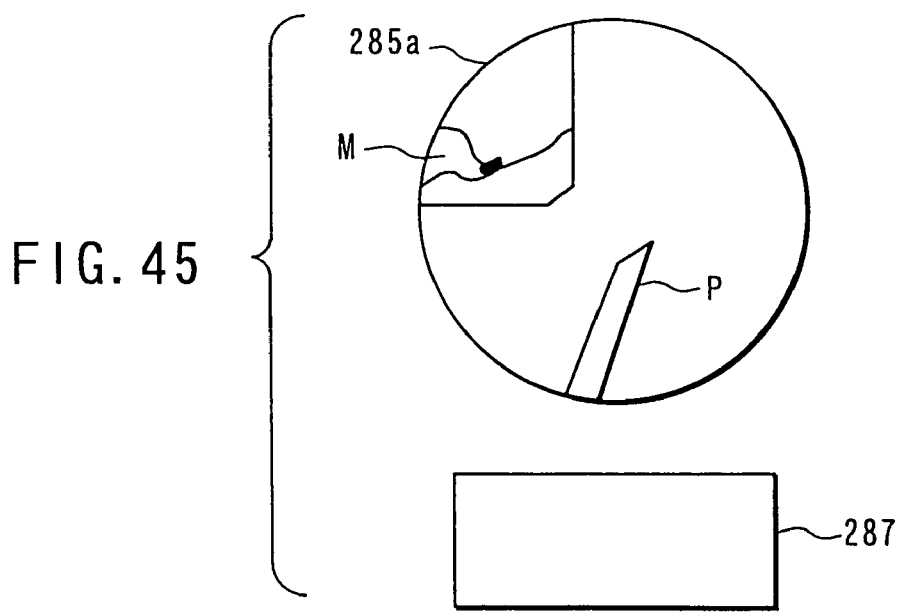
FIG. 45

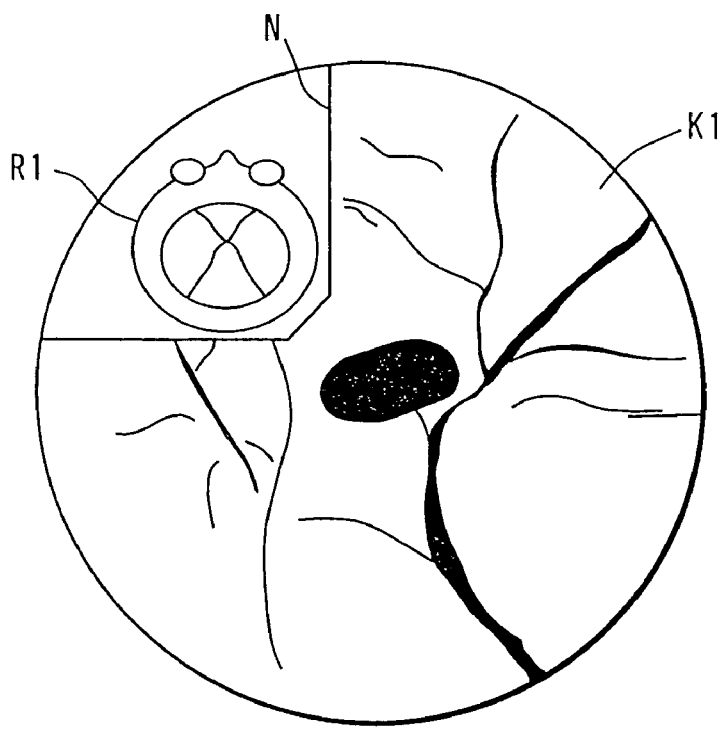
FIG. 64
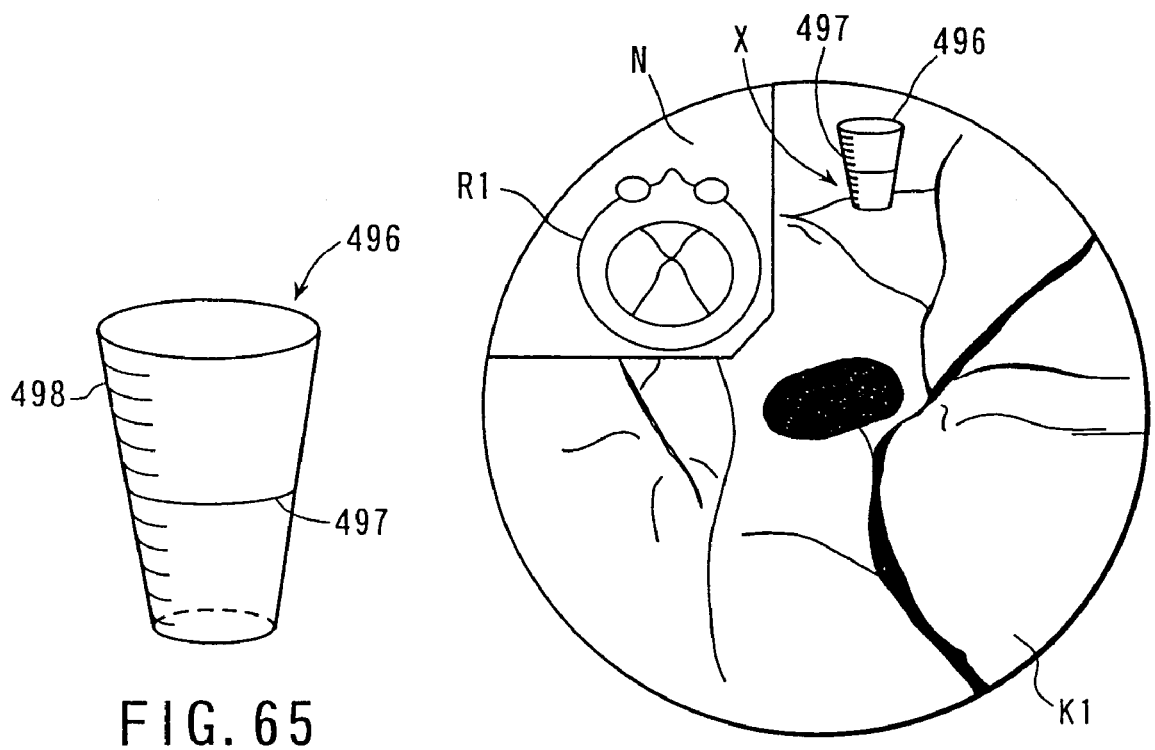
FIG. 65
FIG. 66

OPERATION MICROSCOPE

CROSS REFERENCE TO RELATED APPLICATIONS

This application is a continuation application of application Ser. No. 09/837,787 filed on Apr. 18, 2001 now abandoned which is based upon and claims the benefit of priority from the prior Japanese Patent Applications No. 2000-119995, filed Apr. 20, 2000; No. 2000-180224, filed Jun. 15, 2000; No. 2000-191476, filed Jun. 26, 2000; No. 2000-193223, filed Jun. 27, 2000; and No. 2000-194807, filed Jun. 28, 2000, the entire contents of all of which are incorporated herein by reference.

BACKGROUND OF THE INVENTION

The present invention relates particularly to an operation microscope for use in a surgical operation of a fine portion in cranial nerve surgery, and the like.

In conventional cranial nerve surgery, to absolutely perform a delicate operation, an operation microscope for stereoscopically enlarging an image of a portion being subjected to the operation has been utilized in many cases. Furthermore, in recent years, to certainty carry out an operation, endoscope observation is performed in a conventional operation concurrently with the operation microscope. Therefore, it has been desired that an operation microscope observation image and an endoscope observation image can be simultaneously observed in a field of view of the operation microscope. Moreover, it has also been desired that not only the operation microscope observation image, endoscope observation image, and nerve monitor information but also preoperative CT and MR images can be simultaneously observed during the operation.

Examples of a known prior art include Jpn. Pat. Appln. KOKAI Publication Nos. 9-56669, 11-258514 and Published Japanese Patent No. 11-288328. In these publications, at least a part of an observation image of a second observation means is displayed as an in-field display image in a field of the microscope observation image as first observation means for observing the operative portion. For example, a liquid crystal filter is used to shield the microscope observation image, an image is projected into the shielded portion, and the observation image of the second observation means can be displayed in an arbitrary position in a field of the microscope observation image. Thereby, a dead angle portion which cannot be observed with the microscope observation image and a state inside a body tissue can be recognized by the observation image of the second observation means.

However, in the aforementioned prior art, since the size or the like of the in-field display image displayed in the field of the microscope observation image cannot be freely changed, the image display itself can possibly interfere with the orientation handling of endoscope observation. Furthermore, since the observation image of the second observation means cannot be observed as a large image, there is a problem that the observation image of the second observation means cannot be as finely observed as the large image.

BRIEF SUMMARY OF THE INVENTION

The present invention has been developed in consideration of the aforementioned situations, and an object thereof is to provide an operation microscope by which an endoscope observation image for observing a dead angle of a microscope observation image, image information of a microscope or endoscope observation position by a navigation apparatus, and image information such as an endoscope observation direction are displayed alone or as an arbitrary combination thereof. An operating person can obtain desired image information in accordance with an operational situation, and an operation can be efficiently carried out.

To achieve the aforementioned object, according to the present invention, there is provided an operation microscope provided with a microscope body including an optical eyepiece system for stereoscopically observing an operative portion of a surgical operation, and a microscope image observer for observing an observation image formed for stereoscopic observation by the microscope body, the operation microscope comprising:

a plurality of image forming sections for forming images other than the observation image of the microscope image observer;

an image display for selectively displaying the respective images of the plurality of image forming sections in the microscope image observer;

a display driver for controlling display states of the plurality of images formed by the plurality of image forming sections independently of one another; and an operator for controlling an operation of the display driver.

Moreover, in the present invention, the plurality of image forming sections form the images other than the observation image of the microscope image observer, and the image display selectively displays the respective images of the plurality of image forming sections in the microscope image observer. In this case, the operator controls the operation of the display driver, and controls the display states of the plurality of images formed by the plurality of image forming sections independently of each other.

Therefore, according to the present invention, images other than the observation image of the microscope image observer, such as an endoscope observation image for observing a dead angle of a microscope, image information of a microscope or endoscope observation position by a navigation apparatus, and a plurality of pieces of image information such as endoscope observation direction image information, are displayed alone or as an arbitrary combination thereof. An operating person can obtain appropriate image information in accordance with the operating situation, and the surgical operation can be efficiently carried out.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 12 is a process explanatory view showing the second image display state of the microscope observation field in the operation microscope of the second embodiment.

FIG. 13 is a block diagram showing a main constitution in the operation microscope according to a third embodiment of the present invention.

FIG. 14 is a process explanatory view showing an image display state of the microscope observation field in the operation microscope of the third embodiment.

FIG. 27 is a diagram showing the microscope observation field during fixing of the scope holder in the operation microscope apparatus of the sixth embodiment.

FIG. 28 is a diagram showing the microscope observation field during moving of the scope holder in the operation microscope apparatus of the sixth embodiment.

FIG. 29 is a block diagram showing the control system of the operation microscope apparatus according to a seventh embodiment of the present invention.

FIG. 39 is a diagram showing the microscope observation field during use of an endoscope in the operation microscope apparatus of the ninth embodiment.

FIG. 40 is a diagram showing the microscope observation field whilst using the ultrasonic probe in the operation microscope apparatus of the ninth embodiment.

FIG. 41 is a plan view of a foot switch in the operation microscope apparatus of the ninth embodiment.

FIG. 42 is a process explanatory view of an XY switch when an endoscope observation image is displayed in the microscope observation field in the operation microscope apparatus of the ninth embodiment.

FIG. 43 is a process explanatory view of the XY switch when an ultrasonic probe observation image is displayed in the microscope observation field in the operation microscope apparatus of the ninth embodiment.

FIG. 44 is a block diagram of the control system of the operation microscope apparatus according to a tenth embodiment of the present invention.

FIG. 45 is a diagram showing one example of a superimposed display state of the microscope observation field in the operation microscope apparatus of the tenth embodiment.

FIG. 64 is a plan view showing an image in which a preoperative image is displayed in the sub-screen in the microscope observation image displayed in a field of view of an eyepiece in the operation microscope of the fourteenth embodiment.

FIG. 65 is a perspective view showing a conical character generated by the workstation in the operation microscope of the fourteenth embodiment.

FIG. 66 is a plan view showing an image in which the character is superposed in the microscope observation image in the operation microscope of the fourteenth embodiment.

DETAILED DESCRIPTION OF THE INVENTION

Respective embodiments of the present invention will be described hereinafter with reference to the drawings.

Figure 1:
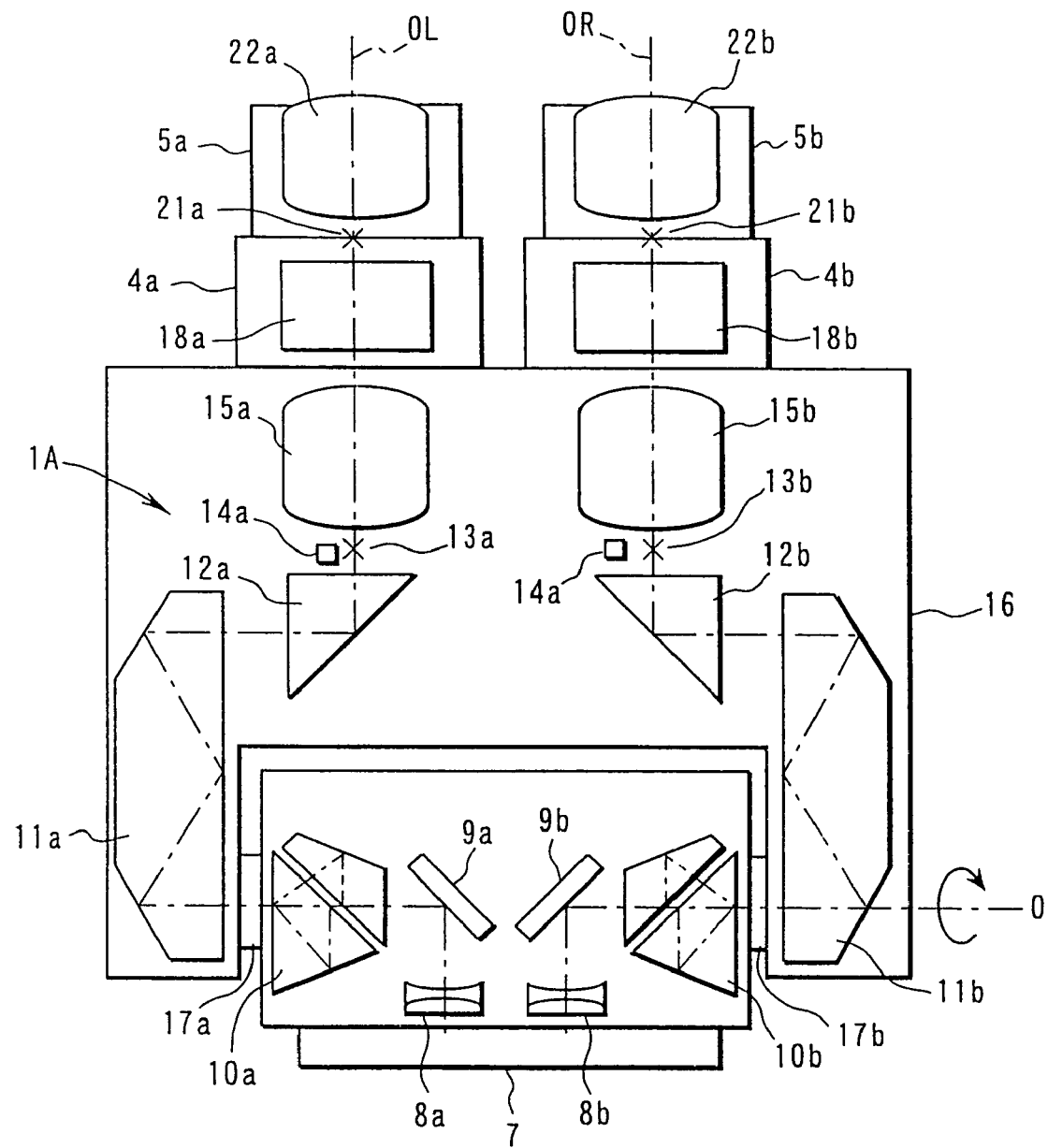
FIG. 1 is a diagram showing an optical constitution of a binocular eyepiece lens tube in an operation microscope according to a first embodiment of the present invention.
Figure 2:
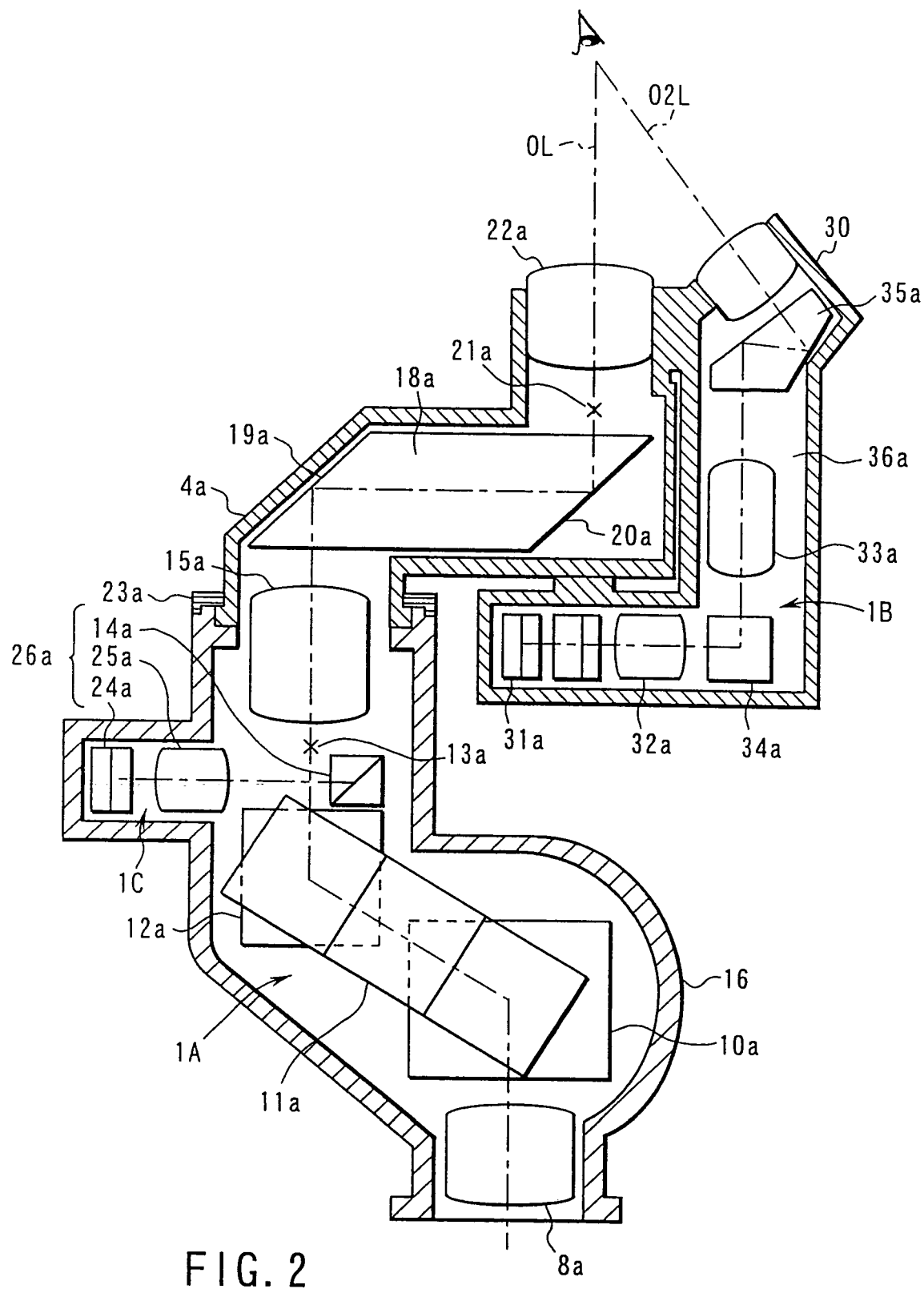
FIG. 2 is a side view showing a left side observation optical system in the binocular eyepiece lens tube of the operation microscope of the first embodiment.

FIG. 1 to FIG. 8 show a first embodiment. FIG. 1 shows an internal optical system constitution of a binocular eyepiece lens tube of an operation microscope 101 (see FIG. 6), and FIG. 2 is a diagram showing a left side optical observation system of FIG. 1. Additionally, a right side optical observation system of the binocular eyepiece lens tube has the same constitution as that of the left optical observation system of FIG. 2, and only the constitution of the left side optical observation system of FIG. 2 will be described here.

As shown in FIG. 1, a fixed housing 7, and a movable housing 16 are disposed in a microscope body 104 (see FIG. 6) of the binocular eyepiece lens tube of the operation microscope 101 of the present embodiment. A pair of left and right image forming lenses 8a, 8b are disposed inside the fixed housing 7. The respective image forming lenses 8a, 8b are optically connected to a first optical observation system 1A. Additionally, besides the first observation optical system 1A, a plurality of optical observation systems, for example, two optical observation systems, as described later in the present embodiment (second and third observation optical systems 1B and 1C) are incorporated in the microscope body 104 of the binocular eyepiece lens tube of the present embodiment.

Moreover, mirrors 9a, 9b for reflecting left and right observation fluxes incident via the image forming lenses 8a, 8b outwardly by 90° are disposed in the first observation optical system 1A. Image rotator prisms 10a, 10b are disposed on outgoing light axes of the mirrors 9a, 9b. Prisms 11a, 11b for reversing each observation flux by 180° are disposed behind the image rotor prisms 10a, 10b. Furthermore, triangular prisms 12a, 12b for reflecting the outgoing light axes from the prisms 11a, 11b in parallel with left and right observation light axes OL, OR by an optical eyepiece system described later are disposed/fixed behind the reversing prisms. First, intermediate image forming points 13a, 13b at which images are formed by the image forming lenses 8a, 8b are positioned behind the triangular prisms 12a, 12b.

Here, upper surfaces of prisms 14a, 14b as light guiding means, as described later, are disposed so as to be aligned substantially on the same plane in the vicinity of the first intermediate image forming points 13a, 13b. Furthermore, relay lenses 15a, 15b for relaying the images are disposed/fixed behind the first intermediate image forming points 13a, 13b.

Moreover, the prisms 11a, 11b, triangular prisms 12a, 12b, and relay lenses 15a, 15b are contained in the movable housing 16. The movable housing 16 is rotatably connected to the fixed housing 7 via connection members 17a, 17b so as to be rotatable around a rotation axis O, that is, the incident light axes of the prisms 11a, 11b.

Furthermore, each of the rotator prisms 10a, 10b can rotate centering on the rotation axis O by an angle of ½ with respect to rotation of the movable housing 16 to the fixed housing 7 by a cam mechanism (not shown).

Additionally, a pair of left and right eye distance adjustment housings 4a, 4b are disposed on respective outgoing light paths from the left and right relay lenses 15a, 15b in the movable housing 16. Parallel prisms 18a, 18b as reflection members are contained in these eye distance adjustment housings 4a, 4b. As shown in FIG. 2, incident reflection surfaces 19a, 19b and outgoing reflection surfaces 20a, 20b are disposed in the respective parallel prisms 18a, 18b. Here, images transmitted via the relay lenses 15a, 15b from the first intermediate image forming points 13a, 13b are formed on second intermediate image forming points 21a, 21b from outgoing reflection surfaces 20a, 20b of the parallel prisms 18a, 18b in the eye distance adjustment housings 4a, 4b.

Moreover, the pair of left and right eye distance adjustment housings 4a, 4b are connected to left and right eyepiece housings 5a, 5b. Moreover, the images formed on the second intermediate image forming points 21a, 21b are guided to a pair of optical eyepiece systems 22a, 22b contained in the eyepiece housings 5a, 5b, and observation light axes OR, OL as microscope optical observation images of the first optical observation system 1A are constituted.

Furthermore, the eye distance adjustment housings 4a, 4b are connected to the movable housing 16 such that the housings 4a, 4b can rotate around axes substantially corresponding to the outgoing light axes (vertical direction in FIG. 2) from the triangular prisms 12a, 12b. Here, as shown in FIG. 2, stoppers 23a, 23b are attached to connection members of the eye distance adjustment housings 4a, 4b with respect to the movable housing 16. Moreover, the eye distance adjustment housings 4a, 4b are supported by the respective stoppers 23a, 23b such that the housings 4a, 4b are immobile in an axial direction with respect to the movable housing 16. Additionally, the present structure and parallel prisms 18a, 18b constitute a so-called G ten top eye distance adjustment mechanism.

Moreover, as shown in FIG. 2, a second eyepiece housing 30 for containing the second observation optical system 1B is disposed outside the eye distance adjustment housings 4a, 4b in the first observation optical system 1A.

The second optical observation system 1B is constituted as follows. FIG. 2 only shows the left light path, because the right light path is similar in structure to the left light path. Numeral 31a denotes a small-sized LCD monitor, controlled by a display controller 46 described later (see FIG. 5), for displaying an image of an endoscope or the like as an electronic image. This small-sized LCD monitor 31a is disposed/ fixed between the eye distance adjustment housing 4*a* and the movable housing 16 disposed below the housing.

Reference numerals 32*a*, 33*a* denote an optical relay system disposed on an outgoing light axis O2L from the LCD monitor 31*a*, and a prism 34*a* for reflecting the light axis O2L substantially by 90° is disposed inside.

Moreover, numeral 35*a* denotes a prism for deflecting the light axis reflected by the prism 34*a* in a direction of an observation light axis OL. A second optical eyepiece system 36*a* is optically disposed/connected on the outgoing light axis O2L of the prism 35*a*. Moreover, the observation light axes OL and O2L intersect each other in the vicinity of an emission pupil position. Thereby, an operating person changes a state in which a line of sight is turned in a direction of the observation light axis OL and a state in which the line of sight is turned in a direction of the outgoing light axis O2L of the prism 35*a* in the same place, and can observe different display screens. Here, when the operating person turns the line of sight in the direction of the observation light axis OL, the operating person can observe a microscope optical observation image of the first optical observation system 1A. Moreover, when the line of sight is turned in the direction of the outgoing light axis O2L of the prism 35*a*, the state can be changed to a second observation state for observing a display image W1 of the LCD monitor 31*a*.

Figure 3:
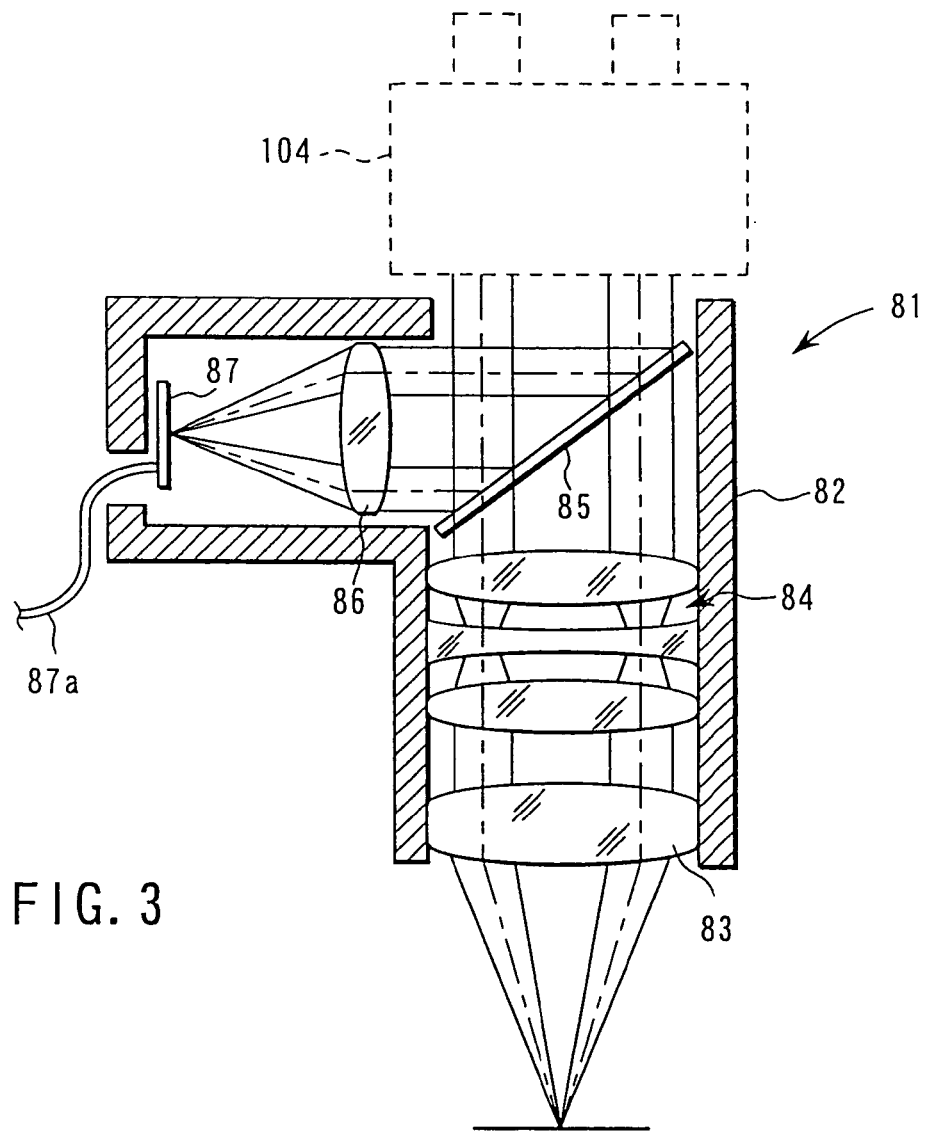
FIG. 3 is a longitudinal sectional view of an overlay display unit in the operation microscope of the first embodiment.

Furthermore, the operation microscope 101 of the present embodiment is provided with an overlay display unit 81 for overlaying/displaying image data such as character data and an arrow in the observation image of the operation microscope 101 as shown in FIG. 3. The overlay display unit 81 includes a microscope body 82 disposed in the light axis of the observation image of the operation microscope 101. The microscope body 82 contains an optical objective system 83 and variable power optical system 84, and a pair of left and right light paths are disposed. Here, a variable focus mechanism and focal distance detecting sensor are disposed in the optical objective system 83. Furthermore, a variable power mechanism and variable power detecting sensor are disposed in the variable power optical system 84.

Furthermore, a half mirror 85 and image insertion optical system 86 as light path insertion means are disposed in the microscope body 82 of the overlay display unit 81. The optical image insertion system 86 combines fluxes emitted from a displaying monitor 87 of a navigation apparatus 59 as an afocal flux, and allows the afocal flux to be incident upon the half mirror 85. Additionally, numeral 87*a* denotes the cable for transmitting an image signal to the image superimposing monitor 87 from the navigation apparatus 59. The image data such as the character data and arrow are displayed in the image superimposing monitor 87.

Moreover, in the half mirror 85 of the overlay display unit 81, the observation image of the operation microscope 101 is sent toward the microscope body 104 of the binocular eyepiece lens tube while the image data such as the character data and arrow displayed in the image superimposing monitor 87 are overlaid/displayed in the observation image of the operation microscope 101 incident from the optical objective system 83.

Figure 4:
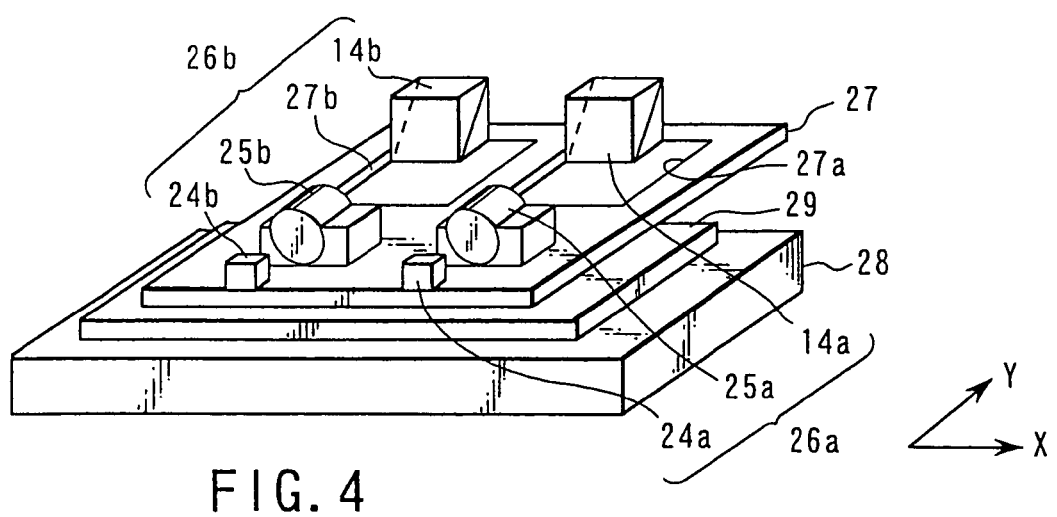
FIG. 4 is a perspective view showing an LCD optical system in the operation microscope of the first embodiment.

Furthermore, left and right LCD optical systems 26*a*, 26*b* are disposed as the third optical observation system 1C for display in a field of view in side positions of the prisms 14*a*, 14*b* in the movable housing 16. FIG. 4 is a perspective view of the LCD optical systems 26*a*, 26*b*. The respective LCD optical systems 26*a*, 26*b* are provided with a pair of small-sized LCD monitors 24*a*, 24*b*, controlled by a controller (not shown), for displaying the image of the endoscope or the like, and image forming lenses 25*a*, 25*b* as optical projection systems disposed on the outgoing light axes of the respective LCD monitors 24*a*, 24*b*. Furthermore, these components are arranged/fixed in such a manner that the images of the LCD monitors 24*a*, 24*b* are formed on the upper surfaces of the prisms 14*a*, 14*b*. Here, one LCD monitor 24*a*, image forming lens 25*a*, and prism 14*a* constitute, for example, the left side LCD optical system 26*a*. Furthermore, the other LCD monitor 24*b*, image forming lens 25*b*, and prism 14*b* constitute the right side LCD optical system 26*b*.

Additionally, the LCD optical systems 26*a*, 26*b* are integrally fixed to a fixing plate 27. This fixing plate 27 is provided with holes 27*a*, 27*b* for avoiding fluxes. The fixing plate 27 is fixed onto an XY table 28*a* as drive means. The XY table 28*a* is disposed so that the table can move in XY directions on a plane crossing at right angles to the light axes of the LCD optical systems 26*a*, 26*b*.

Figure 5:
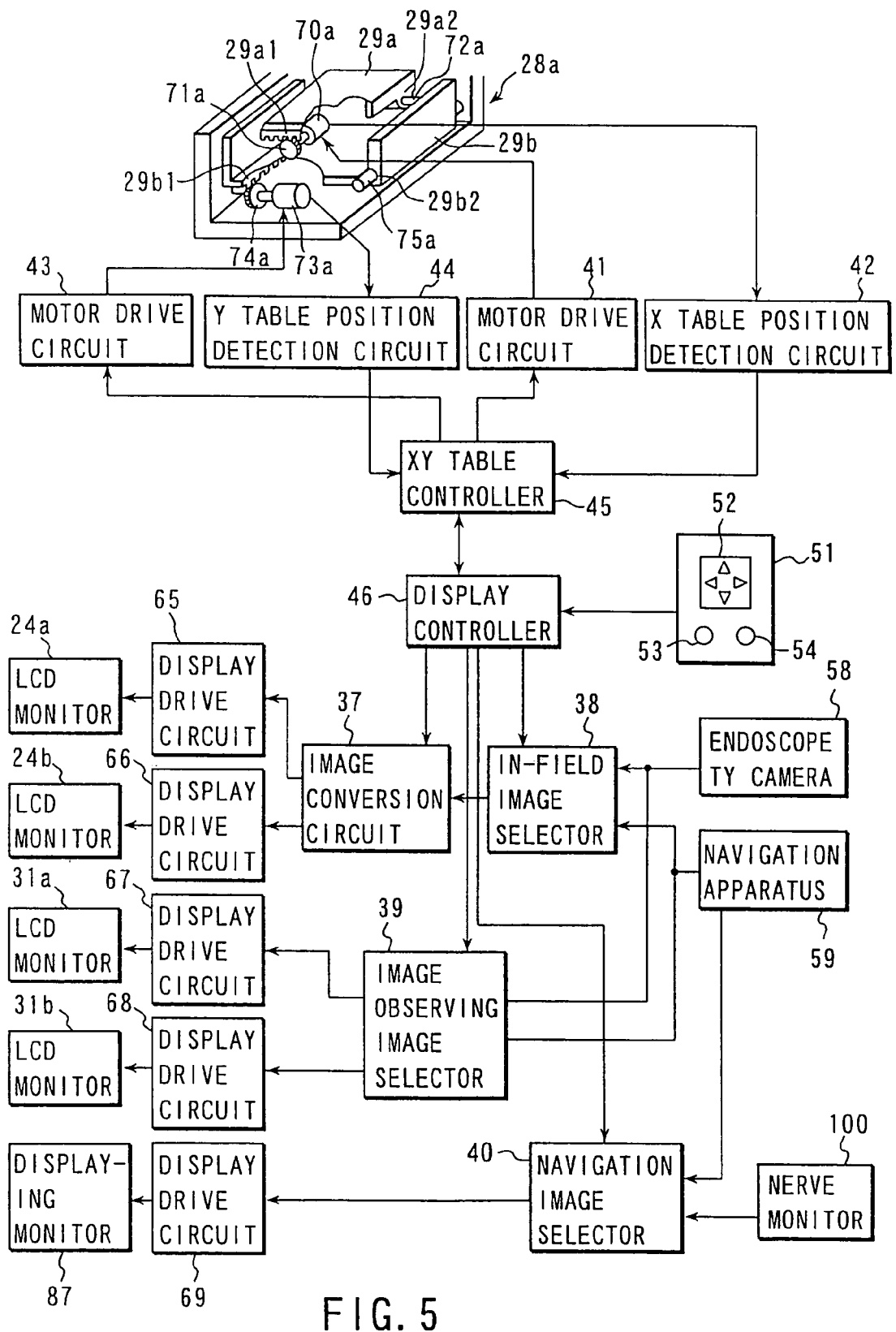
FIG. 5 is a block diagram of a control system of an XY table in the operation microscope of the first embodiment.

FIG. 5 shows a perspective view showing an internal constitution of the XY table 28*a* and a block diagram of a control system. In the XY table 28*a* an X table 29*a* and Y table 29*b* are disposed so that the tables can move in X and Y directions crossing at right angles to each other. The X table 29*a* is provided with a rack 29*a*1 and shaft bearing 29*a*2. The rack 29*a*1 meshes with a pinion gear 71*a* fixed to a rotation shaft of an X table motor 70*a*. Moreover, a guide shaft 72*a* is passed through the shaft bearing 29*a*2. The X table motor 70*a* and guide shaft 72*a* are fixed to the Y table 29*b* as described later. Furthermore, the fixing plate 27 is fixed onto the X table 29*a*.

The Y table 29*b* is provided with a rack 29*b*1 and shaft bearing 29*b*2. The rack 29*b*1 meshes with a pinion gear 74*a* fixed to a rotation shaft of a Y table motor. 73*a*. Moreover, a guide shaft 75*a* is passed through the shaft bearing 29*b*2.

The X and Y table motors 70*a* and 73*a* include encoders, and are electrically connected to a control system described later. That is, the X table motor 70*a* is connected to a motor drive circuit 41, and the encoder is connected to an X table position detection circuit 42. Moreover, the Y table motor 73*a* is connected to a motor drive circuit 43, and the encoder is connected to a Y table position detection circuit 44. Furthermore, the motor drive circuit 41, X table position detection circuit 42, motor drive circuit 43 and Y table position detection circuit 44 are connected to an XY table controller 45.

On the other hand, a controller 51 is operation input means, actuated by the operating person. The controller 51 includes four-direction XY switches 52 for actuating the XY table 28*a* in four XY directions, observer selection switch 53, and display selection switch 54.

The controller 51 is connected to the display controller 46. The display controller 46 is connected to the XY table controller 45. The display controller 46 is connected to an image conversion circuit 37 and in field image selector 38. The in-field image selector 38 is connected to an endoscope TV camera 58 and navigation apparatus 59. Moreover, the image conversion circuit 37 is connected to the LCD monitor 24*a* via a display drive circuit 65 and further to the LCD monitor 24*b* via a display drive circuit 66.

The display controller 46 is further connected to an image selector 39 for observing the image and a navigation image superimposing image selector 40. The image observing image selector 39 is also connected to the endoscope TV camera 58 and navigation apparatus 59. Furthermore, the navigation image superimposing image selector 40 is connected to the navigation apparatus 59 and also to a nerve monitor 100.

The image observing image selector 39 is connected to one (left light path) LCD monitor 31 via a display drive circuit 67, and further to the other (right light path) LCD monitor 31 via a display drive circuit 68. Moreover, the navigation image superimposing image selector 40 is connected to the displaying monitor 87 of the navigation apparatus 59 via a display drive circuit 69.

Figure 6:
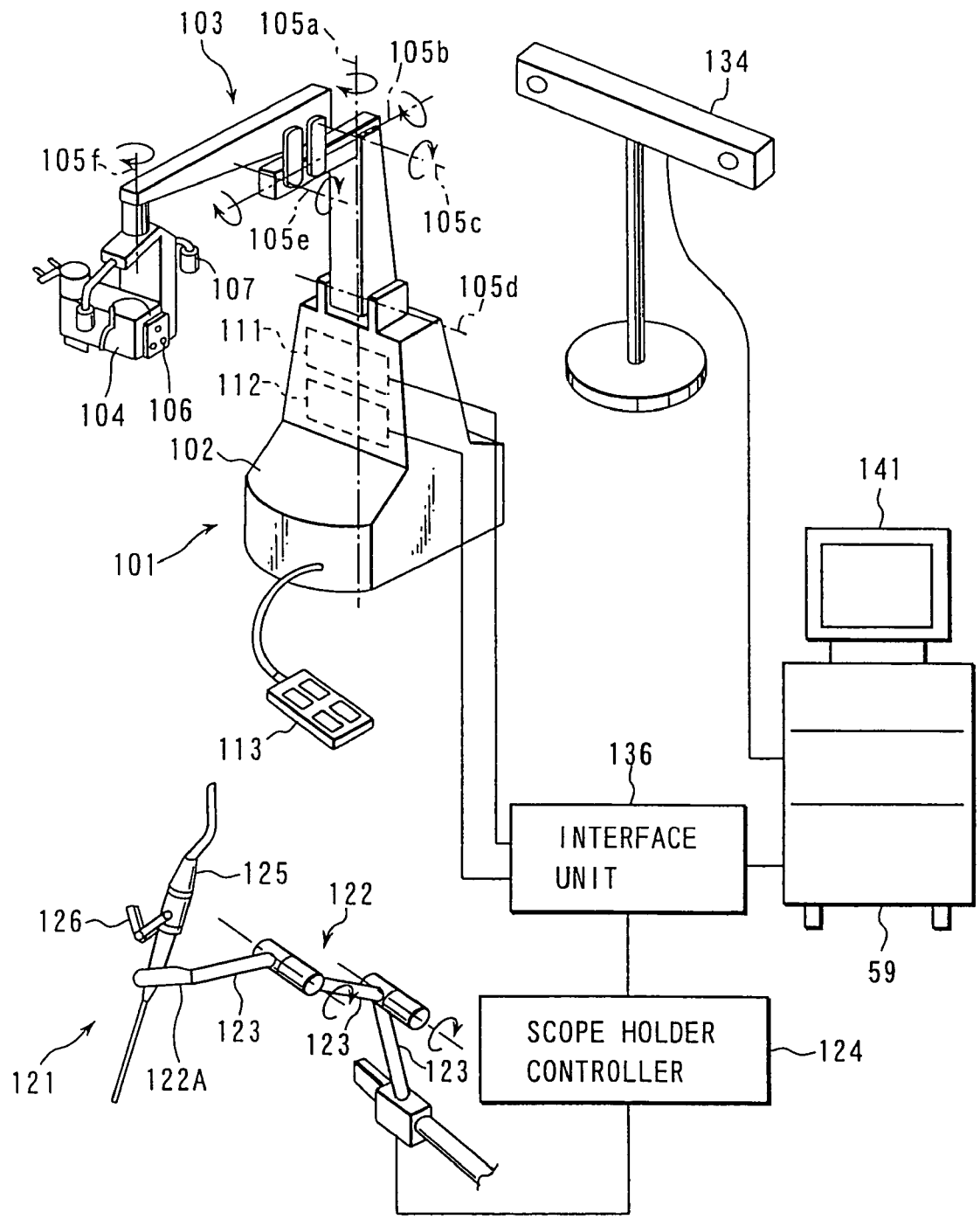
FIG. 6 is a schematic constitution view of the entire operation microscope system in the first embodiment.

Moreover, FIG. 6 is a perspective view showing a constitution of the entire system of an operation microscope apparatus. As shown in FIG. 6, the operation microscope apparatus includes the operation microscope 101 having a solid microscope, endoscope 121 formed of a rigid endoscope for obtaining an observation image other than the observation image of the operation microscope 101, and displaying monitor 141 as display means for displaying the observation images of the operation microscope 101 and endoscope 121.

Moreover, a base 102, balance arm 103 disposed on an upper part of the base 102, and microscope body 104 supported by the balance arm 103 are disposed in the operation microscope 101. Additionally, the respective first to third optical observation systems 1A to 1C shown in FIG. 1 and FIG. 2 are incorporated in the microscope body 104.

Here, the balance arm 103 includes a plurality of movable arms, and six rotation axes 105a to 105f. Furthermore, the respective rotation axes 105a to 105f are provided with electromagnetic locks (not shown) for switching a locking state in which rotation positions of the respective rotation arms of the balance arm 103 are fixed and an unlocked state in which the locked rotation positions are released. Moreover, the microscope body 104 is supported in such a manner that the microscope body 104 can move in a spatial position centering on the respective six rotation axes 105a to 105f of the respective rotation arms of the balance arm 103 with a switching operation for locking/unlocking the electromagnetic locks.

Moreover, the microscope body 104 includes a sensor arm 106 and a grip 107 for controlling a position of the microscope body 104. The grip 107 is provided with respective operation switches for focus adjustment, variable power operation, and arm operation.

Furthermore, the operation microscope 101 incorporates a microscope body controller 111 and arm controller 112. The respective switches of the grip 107 are connected to the microscope body controller 111 and arm controller 112. Additionally, the microscope body controller 111 and arm controller 112 are connected to a foot switch 113 including respective switches for focus adjustment and variable power operation similarly as the respective switches of the grip 107.

Moreover, the endoscope 121 is supported by a scope holder 122 attached to an operating table (not shown). This scope holder 122 is constituted by an articulated arm including a plurality of movable arms 123. Joints among the respective movable arms 123 are rotatably connected to one another. Moreover, the endoscope 121 is movably supported by the scope holder 122.

Furthermore, each rotary member of the scope holder 122 is provided with electromagnetic locking for switching a locking state in which rotation positions of the respective rotation arms 123 of the scope holder 122 are fixed and an unlocked state in which the locked rotation positions are released. Moreover, the endoscope 121 is supported so that the endoscope 121 can move with a switching operation for locking/unlocking the electromagnetic locks.

Moreover, the electromagnetic lock of each rotation member is connected to a scope holder controller 124. Furthermore, a switch 122A for actuating the electromagnetic lock is disposed on a tip end of the scope holder 122. The switch 122A is connected to the scope holder controller 124. Additionally, a TV camera 125 and substantially V-shaped endoscope sensor arm 126 are attached to the endoscope 121.

Furthermore, a digitizer 134 as a photographing apparatus for detecting observation positions of the operation microscope 101 and endoscope 121 is disposed. The digitizer 134 detects the sensor arm 106 of the operation microscope 101 and the sensor arm 126 in the endoscope 121, and the navigation apparatus 59 calculates the correlation of the information with a reference index attached to a patient's head (not shown), to detect the observation positions of the operation microscope 101 and endoscope 121.

The digitizer 134 is connected to the navigation apparatus 59. The navigation apparatus 59 incorporates a memory for diagnosing the image, and also includes correlation processing means with respect to image diagnosis. Furthermore, the navigation apparatus 59 is connected to the display monitor 141, and an interface unit 136. Additionally, image information obtained by the digitizer 134 is inputted to the navigation apparatus 59, and the navigation apparatus 59 calculates the correlation of the information with a reference index attached to the patient's head.

An action of the present embodiment constituted as described above will next be described. During use of the system of the operation microscope apparatus of the present embodiment, the operating person actuates the balance arm 103 of the operation microscope 101 to dispose/fix the microscope body 104 in a desired position. Subsequently, the movable housing 16 is rotated around the axial direction centering on the rotation axis O, and the optical eyepiece systems 22a, 22b are disposed near the operating person's eyes. In this case, the image rotator prisms 10a, 10b in the fixed housing 7 are rotated by ½ of the rotation of the movable housing 16 around the rotation axis O.

In this state, an operated portion is observed by the operation microscope 101. In this case, light emitted from the operated portion is incident upon the image forming lenses 8a, 8b of the first optical observation system 1A via an optical magnification system (not shown) in the microscope body 104. Left and right fluxes are passed through the image rotator prisms 10a, 10b, and rotation of the image is corrected by rotating the movable housing 16 around the axis O. Subsequently, the light is reflected by the prisms 11a, 11b and triangular prisms 12a, 12b, and images are formed in the first intermediate image forming points 13a, 13b.

Subsequently, the light is transmitted via the relay lenses 15a, 15b, and reflected by the parallel prisms 18a, 18b. Thereafter, the image is again formed in the second intermediate image forming point. Then, the image is guided to the optical eyepiece systems 22a, 22b. Therefore, when the operating person looks into the optical eyepiece systems 22a, 22b, stereoscopic observation of the microscope image is performed at a desired scaled-up magnification.

Moreover, when a distance between the left and right observation light axes OL and OR deviates from an operating person's eye distance and stereoscopic observation is impossible, the eye distance adjustment housings 4a and 4b are rotated around an axes substantially agreeing with the outgoing light axes from the triangular prisms 12a, 12b with respect to the movable housing 16. Thereby, so-called eye distance adjustment is performed in order to adjust the left and right observation light axes OL, OR in accordance with the operating person's eye distance.

On the other hand, when the endoscope observation image and images of CT, MR, and the like are to be observed simultaneously with the microscope image, the operating person actuates the controller 51, so that desired image data is displayed in the LCD monitors 24a, 24b of the third optical observation system 1C. In this case, the light emitted by the LCD monitors 24a, 24b is formed into the images on the upper surfaces of the prisms 14a, 14b by the image forming lenses 25a, 25b. Since the upper surfaces of the prisms 14a, 14b are in the vicinity of the first image forming point, the image data of the LCD monitors 24a, 24b, for example, an endoscope image M is displayed on a microscope observation field O as shown by a first image display state of FIG. 7.

Here, when the endoscope image M is displayed on the microscope observation field O, the following process is performed. First, the endoscope TV camera 58 (endoscope image) and navigation apparatus 59 (navigation image) are selected by the display selection switch 54 of the controller 51.

Subsequently, while the endoscope TV camera 58 (endoscope image) is selected by the display selection switch 54, the observer selection switch 53 of the controller 51 is turned ON. In this case, as shown by the first image display state of FIG. 7, a part of the microscope observation field O is cut, and the endoscope image M is displayed in this cut part. Then, the four-direction switch 52 is in a step mode, and turned OFF to obtain a free mode. In this state, when the four-direction switch 52 is selectively turned ON, the XY table 28a is driven in an arbitrary direction and the position of the endoscope image M on the microscope observation field O can be moved in the desired direction.

For example, when the X table motor 70a is driven via the motor drive circuit 41 by operating the four-direction switch 52, the pinion gear 71a rotates. Here, for the X table 29a, the bearing 29a2 is supported by the guide'shaft 72a fixed to the Y table 29b. Therefore, the rack 29a1 moves in the X direction along the guide shaft 72a with the rotation of the pinion gear 71a. Thereby, the fixing plate 27a fixed onto the X table 29a also moves, and the prism 14a moves in the X direction on the first intermediate image forming point 13a. As a result, the endoscope image M moves in the X direction.

Moreover, when the Y table motor 73a is driven via the motor drive circuit 43 by operating the four-direction switch 52, the pinion gear 74a rotates. For the Y table 29b, the bearing 29b2 is supported by the guide shaft 75a fixed to the X table 29a. Therefore, the rack 29b1 moves in the Y direction along the guide shaft 75a with the rotation of the pinion gear 74a. Thereby, the fixing plate 27a fixed onto the Y table 29b also moves, and the prism 14a moves in the Y direction on the first intermediate image forming point 13a. As a result, the endoscope image M moves in the Y direction.

Figure 7:
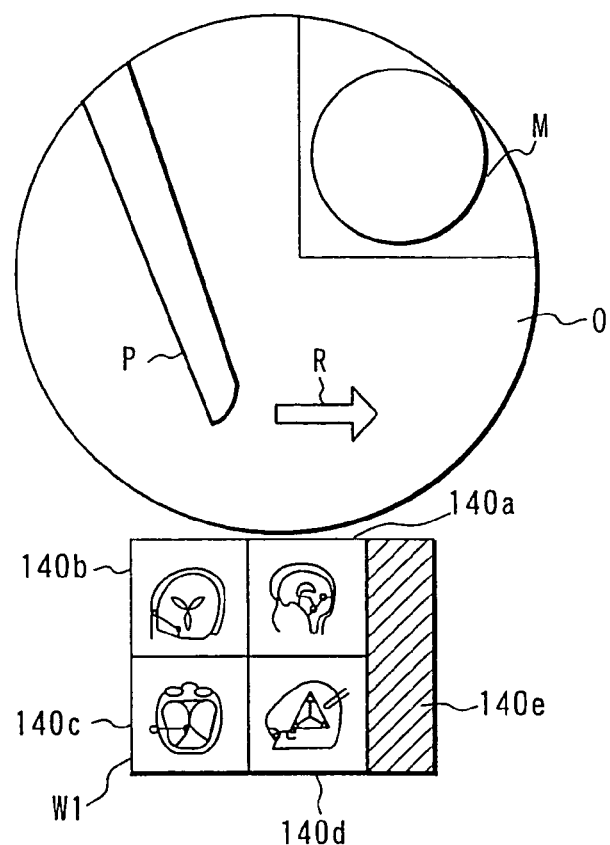
FIG. 7 is a process explanatory view showing a first image display state of a field of microscope observation in the operation microscope of the first embodiment.

Moreover, when the observer selection switch 53 and display selection switch 54 of the controller 51 are operated, as shown in FIG. 7, the endoscope observation image M for observing a dead angle of the microscope 101, image P of the endoscope 121 observed in the microscope observation field O, and perspective direction (arrow) R of the endoscope 121 by navigation can selectively be displayed in the microscope observation field O. In this case, a tomographic image or a three-dimensionally constructed image is displayed in the display screen W1 of the LCD monitors 31a, 31b of the second optical observation system 1B in accordance with treatment positions displayed in the LCD monitors 24a, 24b of the third observation optical system 1C, or the observation position of the operation microscope 101.

That is, three-directional images (respective tomographic image information of sagital, coronal and axial directions) 140a to 140c in accordance with the treatment positions, or the observation positions of the operation microscope 101, and a three-dimensionally constructed image (3D) 140d prepared based on the tomographic images are displayed in the display screen W1 of the LCD monitors 31a, 31b of the second optical observation system 1B. The three-dimensionally constructed image 140d is based on the detection of a microscope observation position, and is a superimposed image of a target (a set pathologically changed portion) indicating an observation point, observation direction, and pre-operation or another simulation result. Additionally, a data display area 140e of a microscope observation position detection apparatus is disposed beside the display screen W1 of the LCD monitors 31a, 31b.

Therefore, the microscope observation image of the operated portion by the first optical observation system 1A and display images of the LCD monitors 24a, 24b can simultaneously be observed through the optical eyepiece systems 22a, 22b of the operation microscope 101. In this case, when the operating person looking into the optical eyepiece systems 22a, 22b casts eyes in an oblique direction, for example, in an outgoing light axis O2L direction from the LCD monitors 31a, 31b of the second observation optical system 1B as shown in FIG. 2, the operating person can observe the displayed screen W1 on the LCD monitors 31a, 31b of the second optical observation system 1B disposed under the microscope observation field O by the optical eyepiece systems 22a, 22b of the operation microscope 101 in FIG. 7. Moreover, the three-dimensionally constructed image 140d is displayed in the LCD monitors 24a, 24b of the third optical observation system 1C, and characters (3D) are displayed in the display images of the LCD monitors 24a, 24b.

Figure 8:
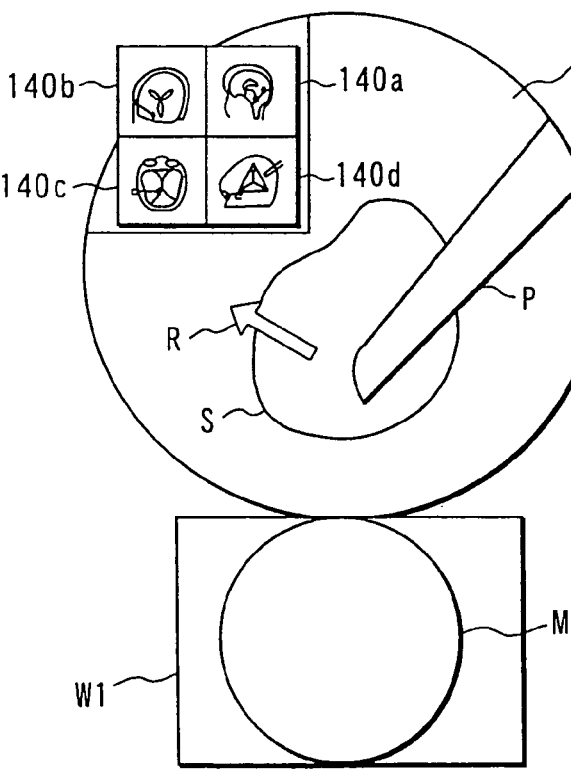
FIG. 8 is a process explanatory view showing a second image display state of the microscope observation field in the operation microscope of the first embodiment.

Moreover, the state can be changed to the second image display state of the microscope observation field O shown in FIG. 8 by operating the observer selection switch 53 and display selection switch 54 of the controller 51. Additionally, FIG. 8 shows a case in which a tumor outline shape display S constituted by a pre-operative diagnosis image obtained by the navigation apparatus 59 is selectively displayed. Here, the observed image P of the endoscope 121, tumor outline shape display S by the preoperative diagnosis image by the navigation apparatus 59, and image displayed in the displaying monitor 87 of the navigation apparatus 59, that is, the oblique direction (arrow) R of the endoscope 121 are superimposed/displayed in the microscope observation field O. Furthermore, the three-dimensional tomographic images 140a to 140c, in accordance with the treatment position by the LCD monitors 24a, 24b or the observation position of the operation microscope, and the three-dimensionally constructed image (3D) 140d are displayed in a part of the microscope observation field O. Moreover, the endoscope image M of the endoscope 121 of that time is displayed in the display screen W1 on the LCD monitors 31a, 31b of the second optical observation system 1B.

Then, the following effect is produced in the aforementioned constitution. That is, in the operation microscope 101 of the present embodiment, the first optical observation system 1A, the additional two optical observation systems (second and third optical observation systems 1B and 1C), and further overlay display unit 81 are disposed in the microscope body 104 of the binocular eyepiece lens tube. Moreover, the operating person stereoscopically observes the microscope image of the operated portion by the first optical observation system 1A of the operation microscope 101 by looking into the optical eyepiece systems 22a, 22b. Furthermore, the endoscope image M displayed in the LCD monitors 24a, 24b of the third optical observation system 1C can be displayed in a part of the microscope observation field O as shown by the first image display state of FIG. 7. In this case, the tomographic image in accordance with the treatment position displayed in the LCD monitors 24a, 24b of the third optical observation system 1C, or the observation position of the operation microscope 101, and the three-dimensionally constructed image can simultaneously be displayed in the display screen W1 of the LCD monitors 31a, 31b of the second optical observation system 1B. Furthermore, the character data, and image data such as the arrow can be overlaid/displayed in the observation image of the operation microscope 101 by the overlay display unit 81 if necessary. Therefore, when the operating person manually operates the observer selection switch 53 and display selection switch 54 of the controller 51 in accordance with operation situations in the operation microscope 101 of the present embodiment, for example, the endoscope observation image M for observing the dead angle of the microscope 101, image information of the microscope and endoscope observation positions by the navigation apparatus 59, and a plurality of pieces of image information such as the endoscope observation direction can be obtained alone or as an arbitrary combination thereof and can simultaneously be displayed. Since desired image information can be obtained in this manner, the operation can efficiently and effectively be carried out.

As described above, two display units are provided, each comprising one LCD monitor and one image selector. One of the display units displays an image that has parallax with respect to the image displayed by the other display unit. Hence, the display units cooperate to display a three-dimensional image. Nonetheless, it may be suffices to use only one display unit. In this case, a two-dimensional image will be displayed, not a three-dimensional image.

Moreover, FIG. 9 to FIG. 12 show a second embodiment of the present invention. The second embodiment is obtained by changing the constitution of the operation microscope 101 of the first embodiment (see FIG. 1 to FIG. 8) as follows.

That is, in the second embodiment, an image input function from the nerve monitor 100 as an operation diagnosis apparatus for checking a function of a cranial nerve is added to the constitution of the operation microscope 101 of the first embodiment. Furthermore, waveform monitor means for monitoring a waveform of the nerve monitor 100 is disposed, the result is used to change the display state of the nerve monitor 100 in accordance with the state of the waveform monitor means, and the waveform can be displayed in the microscope observation field O.

Figure 9:
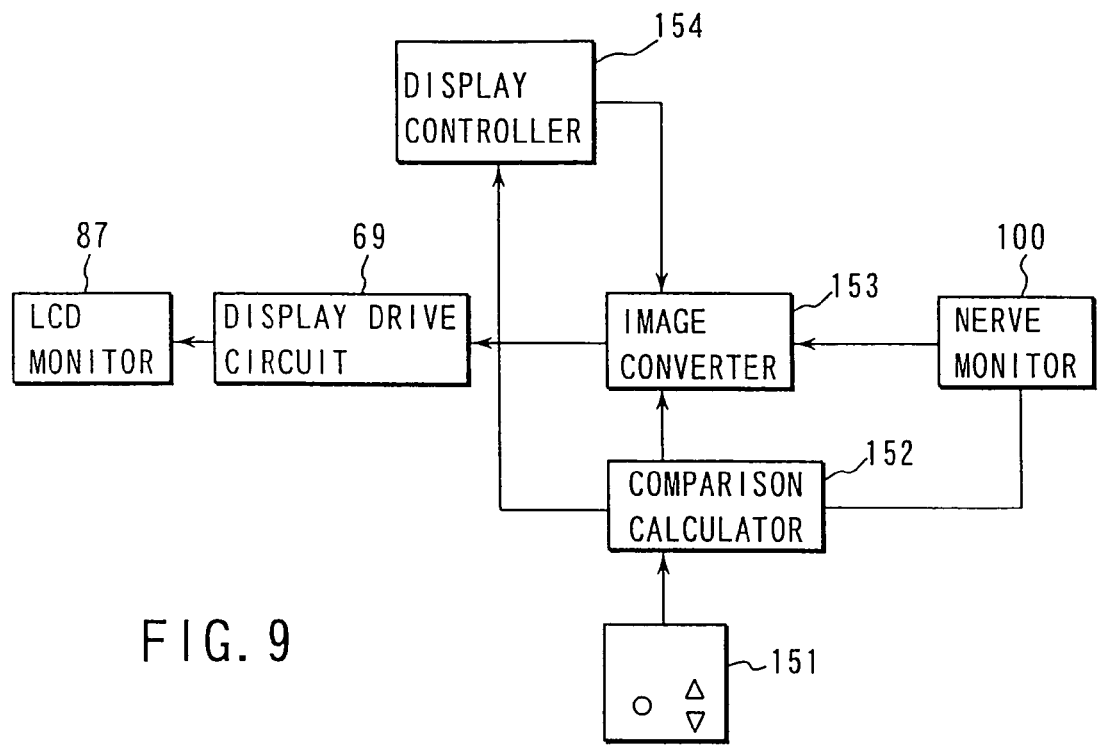
FIG. 9 is a monitor block diagram of a nerve monitor in the operation microscope according to a second embodiment of the present invention.

FIG. 9 is a block diagram for monitoring the nerve monitor 100. Here, a setting input section 151 is connected to an image converter 153 via a comparison calculator 152. The nerve monitor 100 is connected to the comparison calculator 152 and image converter 153. Furthermore, the comparison calculator 152 is connected to a display controller 154 connected to the image converter 153.

Figure 10:
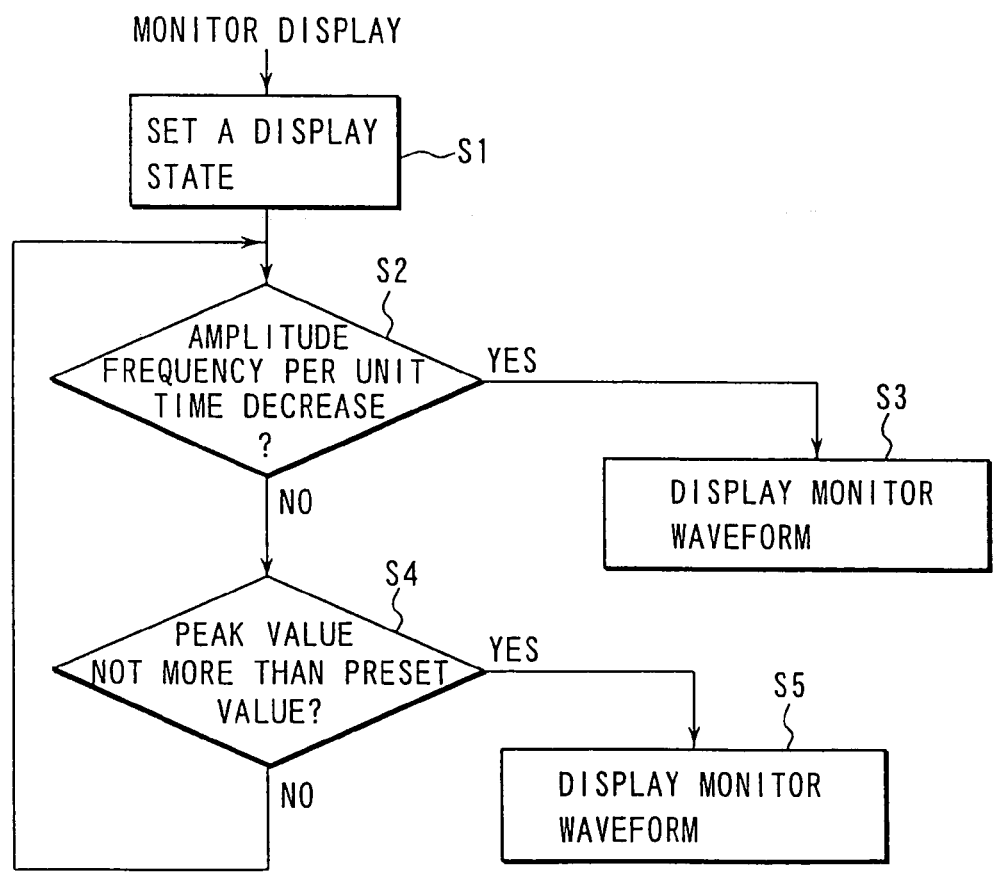
FIG. 10 is a flowchart of a monitor display in the operation microscope of the second embodiment.
Figure 11:
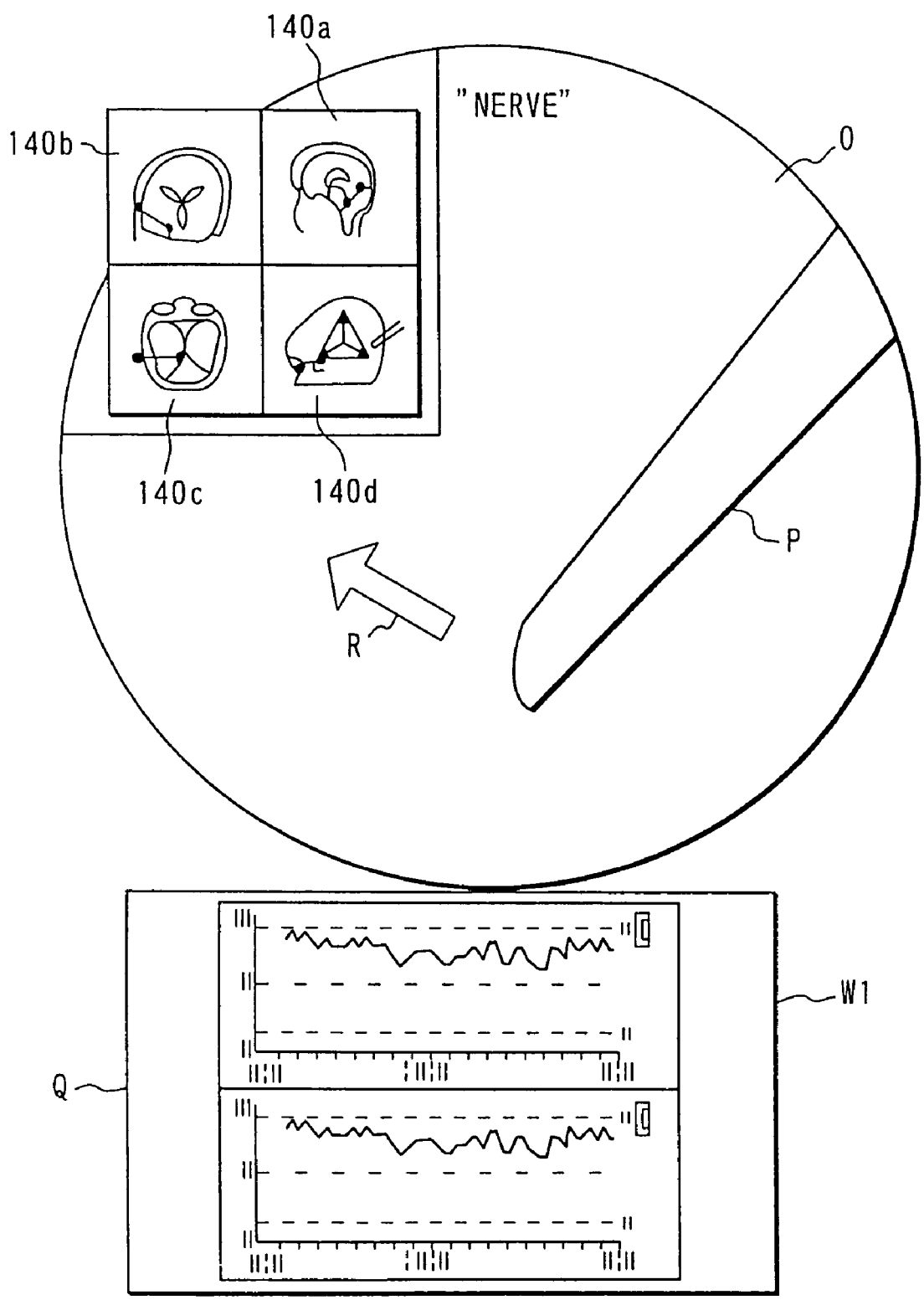
FIG. 11 is a process explanatory view showing the first image display state of the microscope observation field in the operation microscope of the second embodiment.

FIG. 10 is a flowchart of a nerve monitor display. FIG. 11 shows the first image display state of the microscope observation field O. As shown in FIG. 10, in step S1 a display state is set via the setting input section 151, and it is checked in step S2 as to whether or not an amplitude frequency per unit time decreases. If YES in the step S2, a process shifts to step S3 to display a monitored waveform in the displaying monitor 87.

Moreover, if NO in step S3, the process advances to the next step S4. It is checked in step S4 whether a peak value is not more than a preset value. If YES in step S4, the monitored waveform is displayed in the displaying monitor 87 in the next step S5. If NO in step S4, the process returns to step S2.

FIG. 11 shows a state in which characters "NERVE" are superimposed/displayed in the microscope observation field O of the operation microscope 101, and a waveform Q of the nerve monitor 100 is displayed as an electronic image in the display screen W1 of the LCD monitor 31. Therefore, when the operating person looks into the optical eyepiece systems 22a, 22b of the operation microscope 101 in this state, the operating person can observe the three-directional tomographic images 140a to 140c in accordance with the observation position of the operation microscope 101, further the three-dimensionally constructed image 140d and the image P of the endoscope 121 in the microscope observation field O. Furthermore, when the operating person looking into the optical eyepiece systems 22a, 22b casts eyes in the direction of the outgoing light axis O2L from the LCD monitors 31a, 31b of the second optical observation system 1B, the operating person can observe the monitored waveform Q of the electronic image displayed in the display screen W1 of the LCD monitors 31a, 31b.

Therefore, according to the operation microscope 101 of the second embodiment, when the vicinity of the cranial nerve is treated, the image can easily be monitored by the nerve monitor 100, and the operation can be certainty carried out.

FIG. 12 shows the second image display state different from the state of FIG. 11. Here, the image P of the endoscope 121 and the waveform Q of the nerve monitor 100 can be simultaneously displayed in the microscope observation field O, and additionally the endoscope image M by the endoscope 121 is displayed in the field. In this case, the three-directional tomographic images 140a to 140c, and three-dimensionally constructed image 140d are simultaneously displayed in the display screen W1 of the LCD monitors 31a, 31b in accordance with the observation position of the operation microscope.

Moreover, when the operating person looks into the optical eyepiece systems 22a, 22b of the operation microscope 101 in the state of FIG. 12, the operating person can simultaneously observe the image P of the endoscope 121 and waveform Q of the nerve monitor 100 in the microscope observation field O, and can additionally observe the endoscope image M in the field. Furthermore, when the operating person looking into the optical eyepiece systems 22a, 22b casts eyes in the outgoing light axis O2L direction from the LCD monitors 31a, 31b of the second optical observation system 1B, the operating person can observe the three-directional tomographic images 140a to 140c in accordance with the observation position of the operation microscope 101, and further, the three-dimensionally constructed image 140d in the display screen W1 of the LCD monitors 31a, 31b.

Therefore, also in this case, when the vicinity of the cranial nerve is treated, the image can easily be monitored by the nerve monitor 100, and the operation can be certainty carried out.

Moreover, FIG. 13 and FIG. 14 show a third embodiment. The third embodiment is constituted by adding the following function of the constitution of the operation microscope 101 of the first embodiment (see FIG. 1 to FIG. 8).

That is, the third embodiment additionally includes a function of transmitting a microscope observation image O photographed in an operating theater to a conference room outside the operating room, so that input image information can be displayed in an image display of the microscope 101 in the operating theater by pen touch input in an external conference room. Thereby, an instruction can directly be given to the operating person who is carrying out the operation from an external conference room.

In FIG. 13, numeral 155 denotes an operating theater, and 156 denotes a conference room. The rooms are partitioned by a wall 157. The microscope observation image of the operation microscope 101 photographed in the operating theater 155 is transmitted to a monitor 160 via an image synthesis apparatus 159 of the conference room 156 from an interface 158. Thereby, as shown in FIG. 14, the microscope observation image O of the operation microscope 101 is displayed in the monitor 160 of the conference room 156.

Moreover, the image synthesis apparatus 159 is provided with a pen type input tool 161. Moreover, when an instruction image 162 is inputted into the monitor 160 by pen touch from the pen type input tool 161, the instruction image 162 is displayed in the LCD monitors 31a, 31b of the second optical observation system 1B in the operation microscope 101. Thereby, an operator in the conference room 156 can give an instruction to the operating person in the operating theater 155.

Therefore, in the third embodiment, when the operating person looking into the optical eyepiece systems 22a, 22b of the operation microscope 101 casts eyes in the outgoing light axis O2L direction from the LCD monitors 31a, 31b of the second optical observation system 1B, the person can easily and precisely receive the instruction image 162 from an experienced doctor displayed in the display screen W1 of the LCD monitors 31a, 31b and can take the necessary steps depending on the circumstances.

Figure 15:
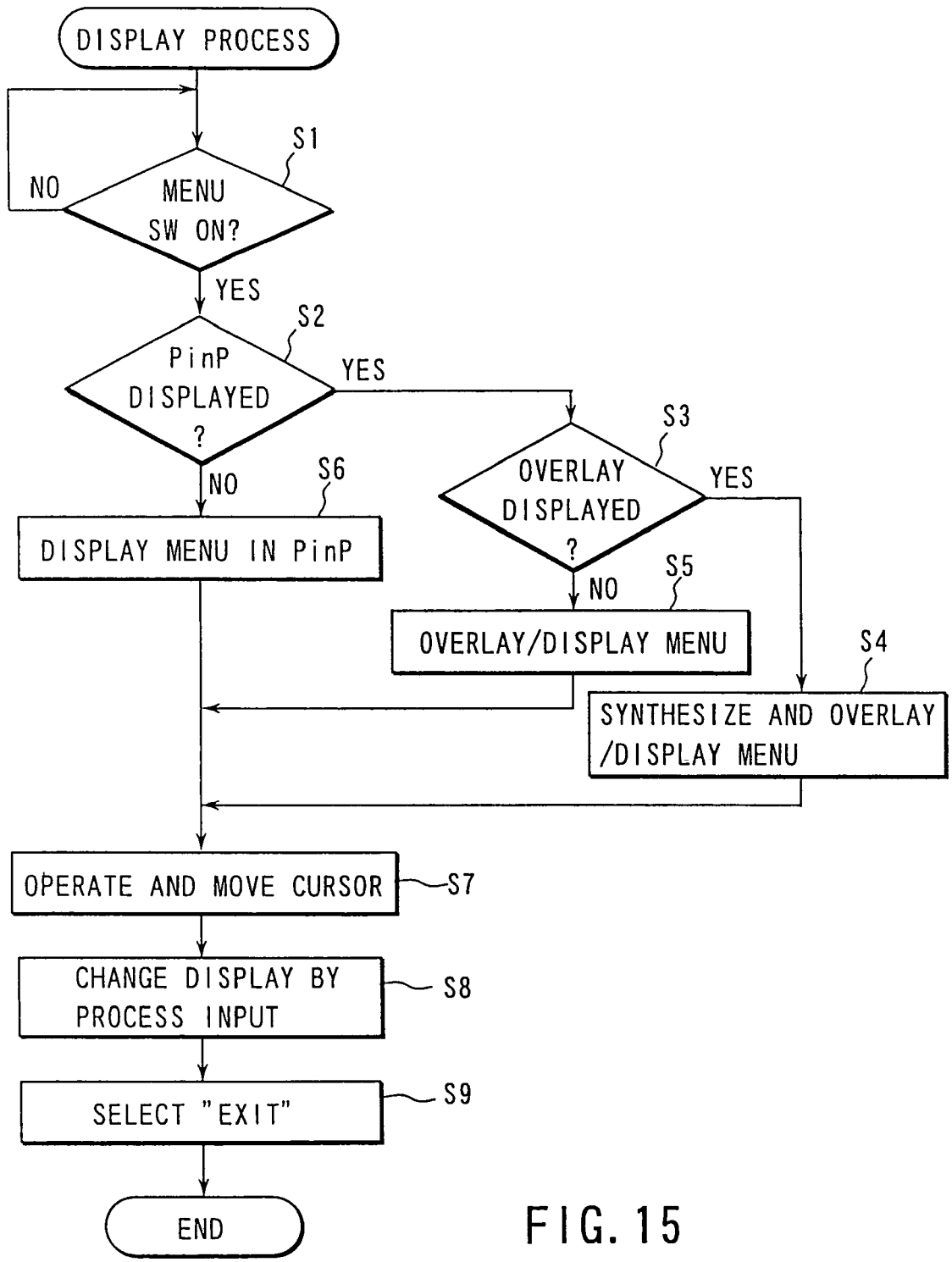
FIG. 15 is a flowchart showing the image display state of the microscope observation field in the operation microscope according to a fourth embodiment of the present invention.
Figure 16:
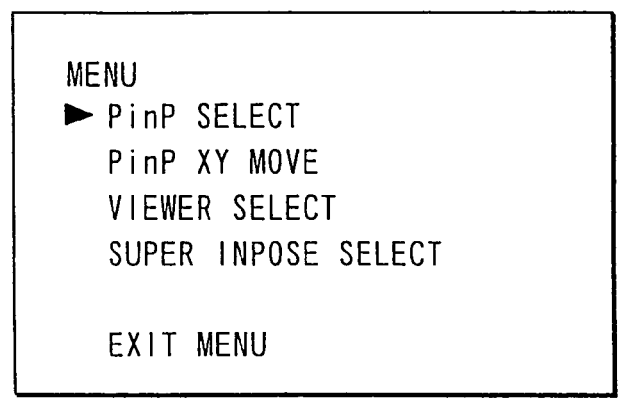
FIG. 16 is a diagram showing a menu display in the operation microscope of the fourth embodiment.
Figure 17:
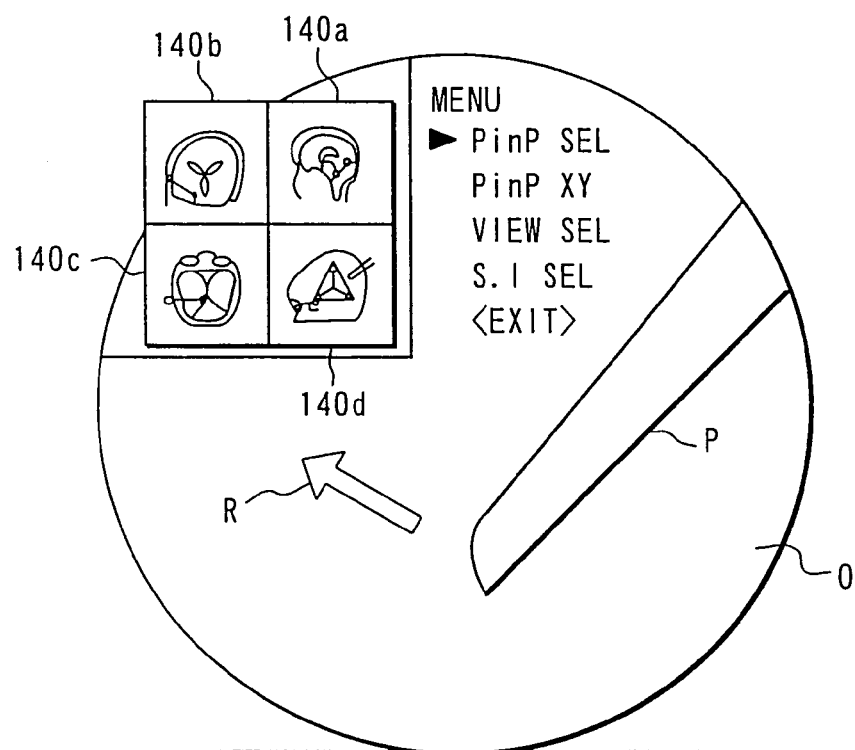
FIG. 17 is a process explanatory view showing an image display state of the microscope observation field in the operation microscope of the fourth embodiment.

FIG. 15 to FIG. 17 show a fourth embodiment. The fourth embodiment is constituted by changing the constitution of the operation microscope 101 of the first embodiment (see FIG. 1 to FIG. 8) as follows.

That is, in the fourth embodiment, as shown in FIG. 17, an operation inputting menu screen is overlaid/displayed in the microscope observation field O of the operation microscope 101 of the first embodiment, and the display image can selectively be operated.

FIG. 15 is a menu process flowchart, FIG. 16 is a menu display state into PinP, and FIG. 17 is a menu superimposed display state.

In the fourth embodiment, during a process of overlaying/displaying the menu screen for inputting the process into the microscope observation field O of the operation microscope 101, the process shown in the flowchart of FIG. 15 is performed. First, it is judged in step S1 whether or not a menu SW is turned ON by the foot switch or the like. If YES in step S1, the process advances to step S2. If NO in step S1, the process returns to a start.

It is judged in step S2 whether or not PinP is displayed. If YES, the process advances to step S3 to judge whether or not overlay display is being displayed. If YES in step S3, the process advances to step S4 to synthesize a menu and overlay/display an operation inputting menu screen in the microscope observation field O. If NO in step S3, the process advances to step S5 to overlay/display the menu.

If NO in step S2, the process advances to step S6 to display the menu in PinP. Subsequently, the process advances to step S7, and the controller 51 is operated to move a cursor. Furthermore, after the menu display is changed by inputting the process in the next step S8, EXIT is selected in step S9 to end the process.

Therefore, as shown in FIG. 17, characters "MENU" and a menu content are overlaid/displayed in the microscope observation field O. Additionally, the three-directional tomographic images 140a to 140c, corresponding to the observation position of the operation microscope 101, and the three-dimensionally constructed image 140d are displayed in the field. Furthermore, the endoscope image M from the endoscope 121 is simultaneously displayed in the LCD monitors 31a, 31b of the second optical observation system 1B. Therefore, when the operating person looking into the optical eyepiece systems 22a, 22b of the operation microscope 101 casts eyes in the outgoing light axis O2L direction from the LCD monitors 31a, 31b of the second optical observation system 1B, the person can observe the endoscope image M displayed in the display screen W1 of the LCD monitors 31a, 31b.

The operating person can select the display of PinP, overlaid/displayed image, and image observation in the microscope observation field O. Therefore, the operation can be carried out, while efficiently selecting, displaying and observing the necessary image information.

Figure 18:
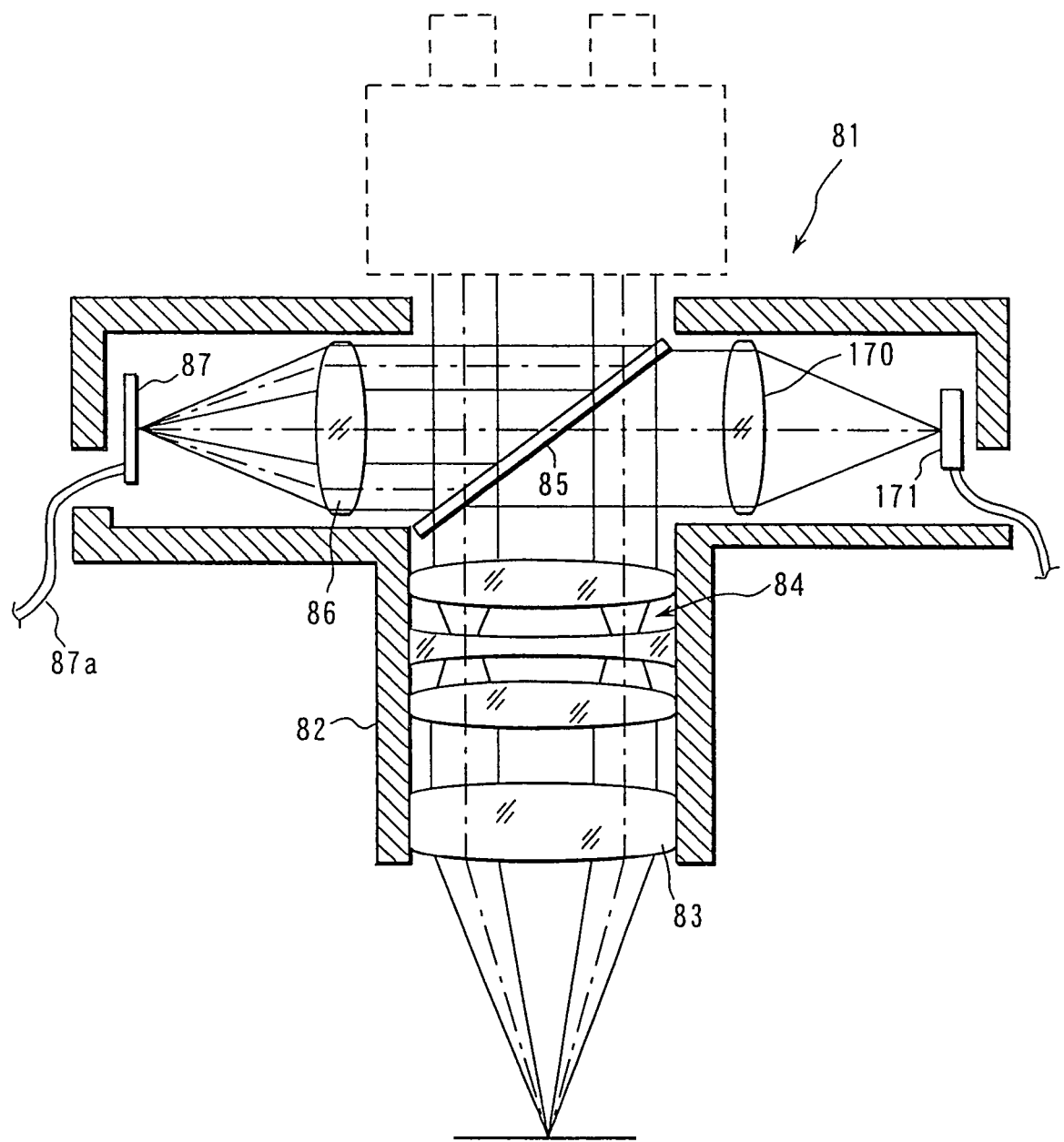
FIG. 18 is a longitudinal sectional view of an overlay display unit in the operation microscope of a fifth embodiment of the present invention.
Figure 19:
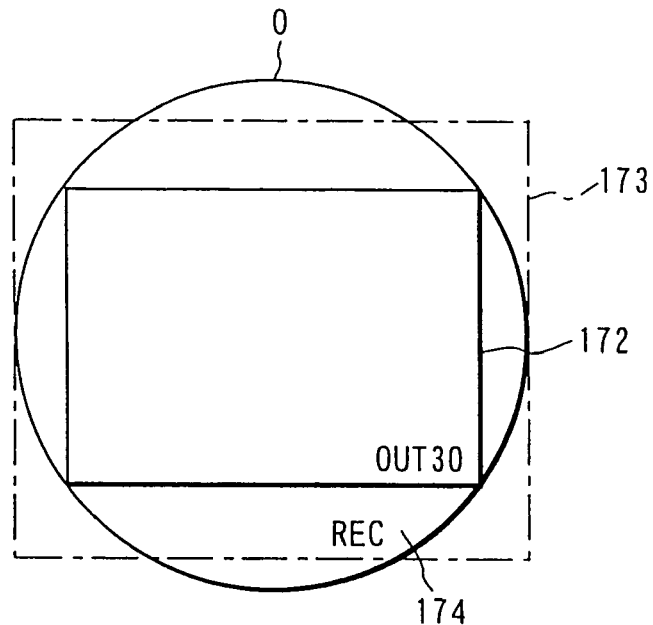
FIG. 19 is a process explanatory view showing an image display state of the microscope observation field in the operation microscope of the fifth embodiment.
Figure 20:
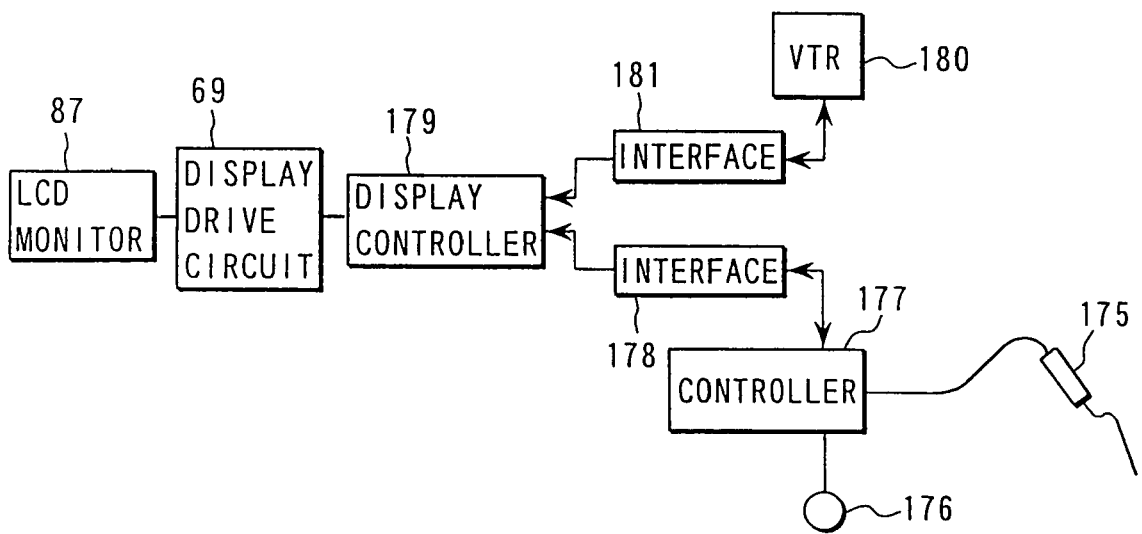
FIG. 20 is a block diagram showing a main constitution of a bipolar treatment apparatus in the operation microscope of the fifth embodiment.

FIG. 18 to FIG. 20 show a fifth embodiment. The fifth embodiment is constituted by changing the constitution of the operation microscope 101 of the first embodiment (see FIG. 1 to FIG. 8) as follows. FIG. 18 is a sectional view showing a modification example of the overlay display unit 81 shown in FIG. 3, FIG. 19 is a view showing the microscope observation field, and FIG. 20 is a block diagram of a bipolar treatment apparatus.

That is, in the fifth embodiment, as shown in FIG. 18, a TV camera image pickup device 171 is disposed on an opposite side of the LCD monitor 87 via the half mirror 85 and an image forming lens 170 in the microscope body 82 of the overlay display unit 81.

In the fifth embodiment, as shown in FIG. 19, a TV camera image pickup range 172 by the TV camera image pickup device 171 is set to be different from an image superimposing range 173 in which the image is superimposed, and the image superimposing range 173 is set to be larger than the TV camera image pickup range 172. Moreover, a VTR recording situation is confirmed/displayed, and a treatment apparatus information is displayed in an information display range 174 which is not photographed by a TV camera.

As the treatment apparatus, for example, a bipolar treatment tool 175 for warm/hot treatment is used as shown in FIG. 20. The bipolar treatment tool 175 is connected to a controller 177 including a foot switch 176. The controller 177 is connected to a display controller 179 via an interface 178. Moreover, VTR 180 is also connected to the display controller 179 via an interface 181.

In this constitution, during image recording by the VTR 180, information only required during the operation, such as characters "REC", is displayed in the information display range 174, and information also required after the operation, such as an output state of the bipolar treatment tool 175, can be displayed in the TV camera image pickup range 172.

Therefore, in the fifth embodiment, when the operating person looks into the optical eyepiece systems 22a, 22b of the operation microscope 101, the person can confirm a recording state in the VTR, a state of the treatment apparatus, and the like in the microscope observation field O.

Figure 21:
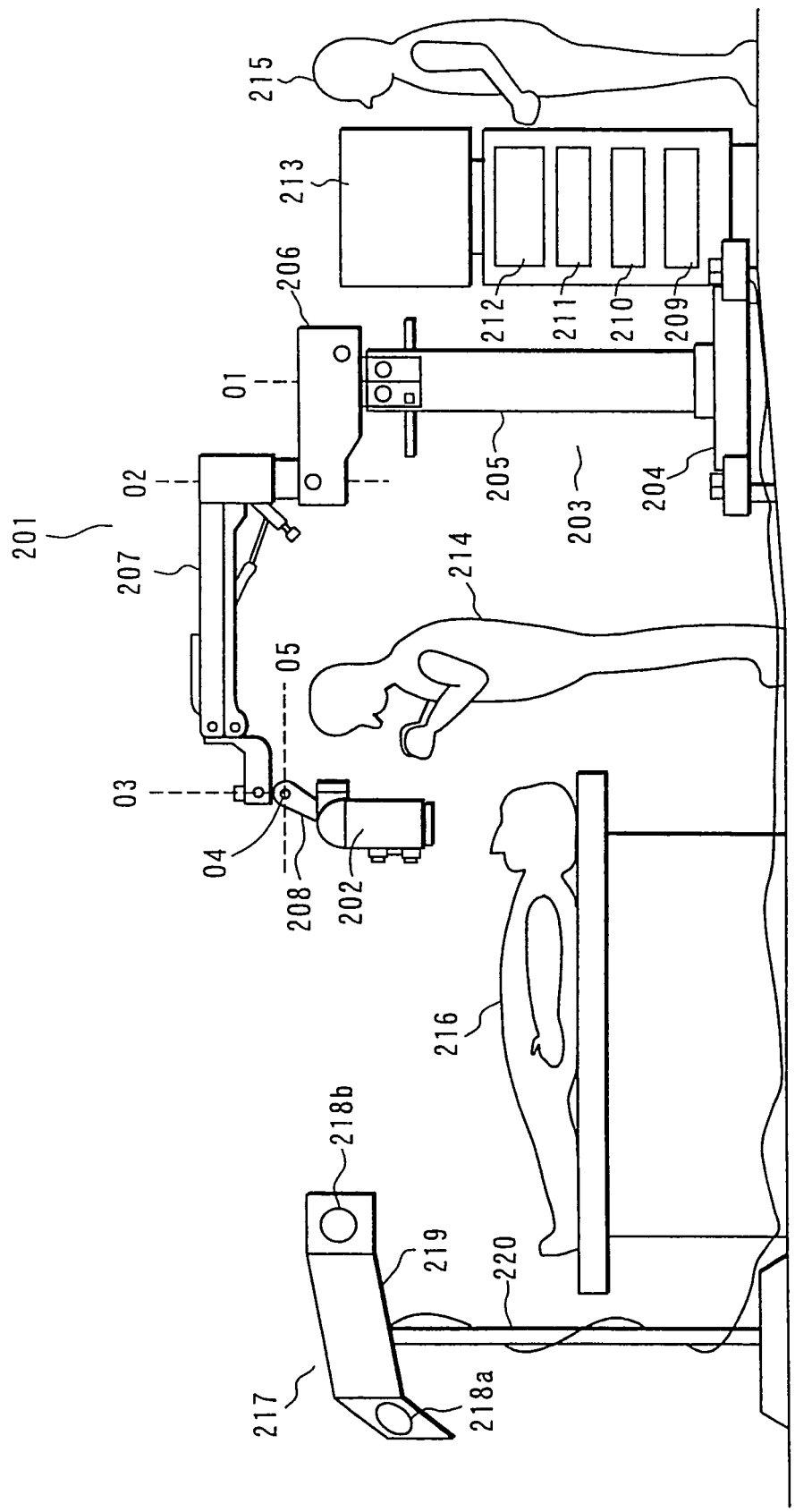
FIG. 21 is a schematic constitution diagram showing the entire system of an operation microscope apparatus according to a sixth embodiment of the present invention.

FIG. 21 to FIG. 28 show a sixth embodiment. FIG. 21 is a schematic constitution diagram of the entire system of the operation microscope apparatus. In an operation microscope 201, a base 204 movable on a floor surface, and a support 205 vertically disposed on the base 204 form a stand 203. Furthermore, one end of a first arm 206 including a light source (not shown) is attached to an upper part of the support 205 so as to be rotatable centering on an axis O1.

Furthermore, the other end of the first arm 206 is attached to one end of a second arm 207 rotatably centering on an axis O2. The second arm 207 is a pantograph arm constituted of a link mechanism and balance adjusting spring member, and vertically moves. The other end of the second arm 207 is attached to one end of a third arm 208 rotatably centering on an axis O3. The other end of the third arm 208 is connected to a microscope body 202. Here, the third arm 208 can support the microscope body 202 so that the microscope body 202 can move back and forth centering on an axis O4 with respect to an operating person's observation direction, and can move in an operating person's horizontal direction centering on an axis O5.

Furthermore, rotating members (joints) in the rotation axes O1 to O5 are provided with electromagnetic brakes (not shown) in order to arbitrarily adjust and fix a spatial position of the microscope body 202. The electromagnetic brake is connected to an electromagnetic brake power source circuit (not shown) incorporated in the support 205.

Additionally, an LED control apparatus 209 is disposed in the operating theater. The LED control apparatus 209 is connected to a measurement apparatus 210. The measurement apparatus 210 is connected to a workstation 212 via an A/D converter 211. The workstation 212 is connected to a monitor 213. Moreover, pre-operative tomographic image data prepared by image diagnosis apparatuses (not shown) such as CT and MRI, and three-dimensional data constructed again by processing the tomographic image data are recorded in the workstation 212. Furthermore, numeral 214 denotes an operating person, 215 denotes an assistant, and 216 denotes a patient.

Numeral 217 denotes a digitizer (optical position detection apparatus) for detecting a position of the sensor arm disposed in the microscope body 202 in a three-dimensional coordinate. The digitizer 217 is constituted as a receiving member by a camera support member 219 and stand 220 for fixing two CCD cameras 218a, 218b, and installed in the operating theater. Moreover, a reference position sensor is disposed on the patient 216.

Figure 22:
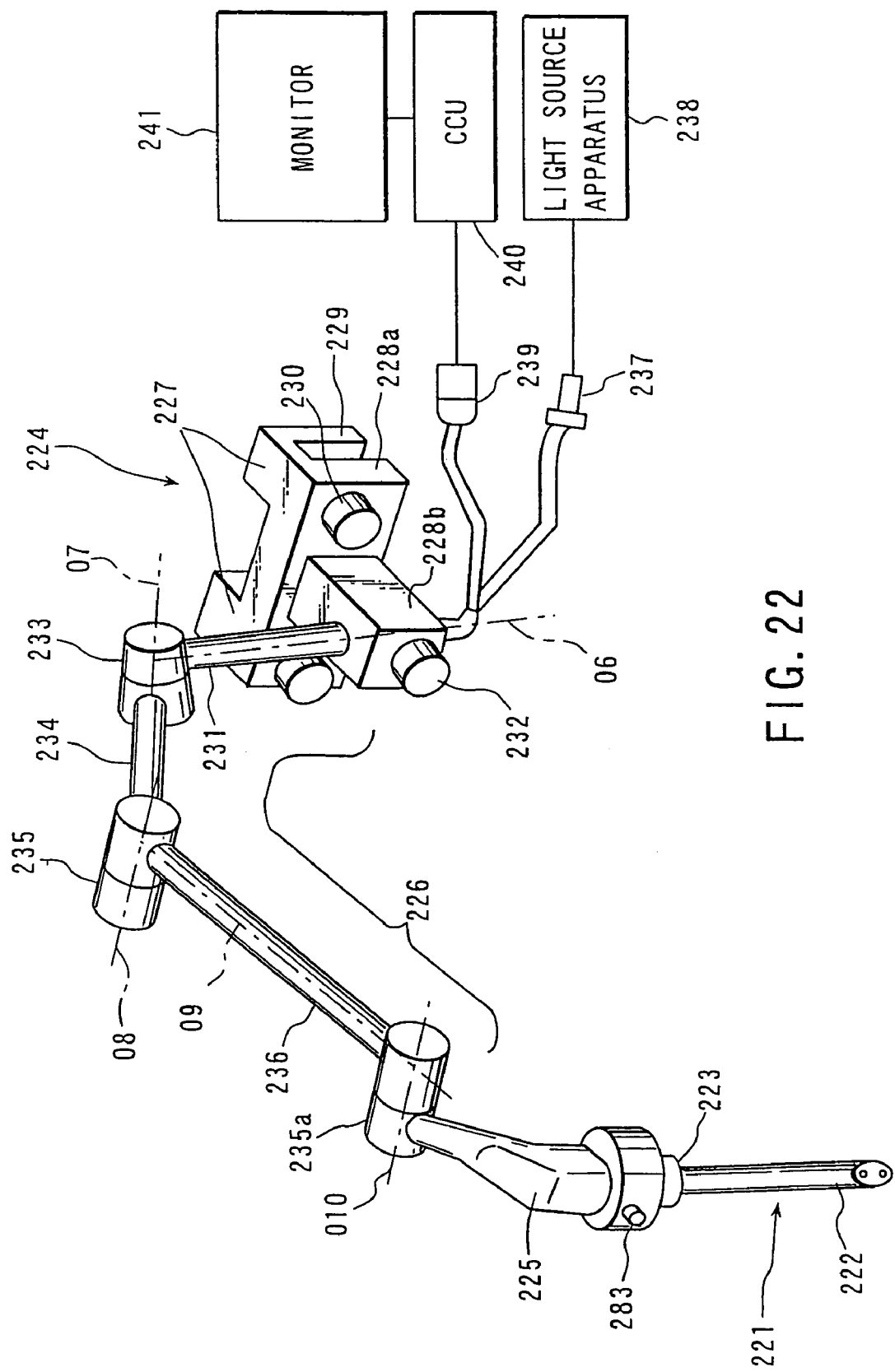
FIG. 22 is a perspective view showing a scope holder in the operation microscope apparatus of the sixth embodiment.

FIG. 22 shows a scope holder apparatus. The apparatus is provided with an endoscope 221 formed of a rigid endoscope, and a scope holder 224 for holding the endoscope 221. The endoscope 221 is provided with an insertion member 222 to be inserted into a body cavity. A base end of the insertion member 222 is provided with a connection member 223 connected to the scope holder 224.

Moreover, the scope holder 224 is disconnectably connected to the connection member 223 of the endoscope 221. The scope holder 224 is constituted by an image pickup unit 225 for picking up the observation image obtained by the endoscope 221, a holding arm 226 for holding the endoscope 221 via the image pickup unit 225, and an attachment member 227 detachably attached to a side rail of an operating bed, for example, shown in FIG. 21.

The attachment member 227 of the scope holder 224 is formed by an attachment member main body 228a, and a base 228b extended from the attachment member main body 228a. A hook-shaped engagement member 229 to be hooked/attached to the operating bed side rail is attached to the attachment member main body 228a.

A fixing knob 230 is attached to the attachment member main body 228a. This fixing knob 230 is screwed and attached to the attachment member main body 228a, and includes a screw member extending toward the engagement member 229. Therefore, when the engagement member 229 is hooked on the side rail and the fixing knob 230 is fastened, the attachment member main body 228a can be fixed to the side rail.

A vertical arm 231 constituting the holding arm 226 is rotatably attached to the base 228b of the attachment member 227. This vertical arm 231 vertically extends upward from the base 228b, and can rotate centering on a first vertical axis O6 corresponding to a longitudinal direction axis.

Moreover, an adjustment knob 232 for adjusting a rotating force amount of the vertical arm 231 centering on the first axis O6 is screwed and attached to the base 228b. One end of a first link arm 234 constituting the holding arm 226 is rotatably attached to an upper end of the vertical arm 231 via a joint 233. In this case, the first link arm 234 can rotate centering on a second axis O7 crossing at right angles to the first axis O6.

One end of a second link arm 236 is rotatably attached to the other end of the first link arm 234 via a joint 235. In this case, the second link arm 236 can rotate centering on a third axis O8 parallel to the second axis O7, and can rotate centering on a fourth axis O9 crossing at right angles to the third axis O8. Moreover, the image pickup unit 225 can be rotatably attached to the other end of the second link arm 236 via a joint 235a. In this case, the image pickup unit 225 can rotate centering on a fifth axis O10 crossing at right angles to the fourth axis O9.

An optical lighting system of the endoscope 221 is connected to a light guide cable 237 passed through the scope holder 224. The light guide cable 237 is connected to a light source apparatus 238. Moreover, an optical observation system of the endoscope 221 is connected to a TV cable 239 passed through the scope holder 224. The TV cable 239 is connected to a monitor 241 via a camera control unit 240.

Figure 23:
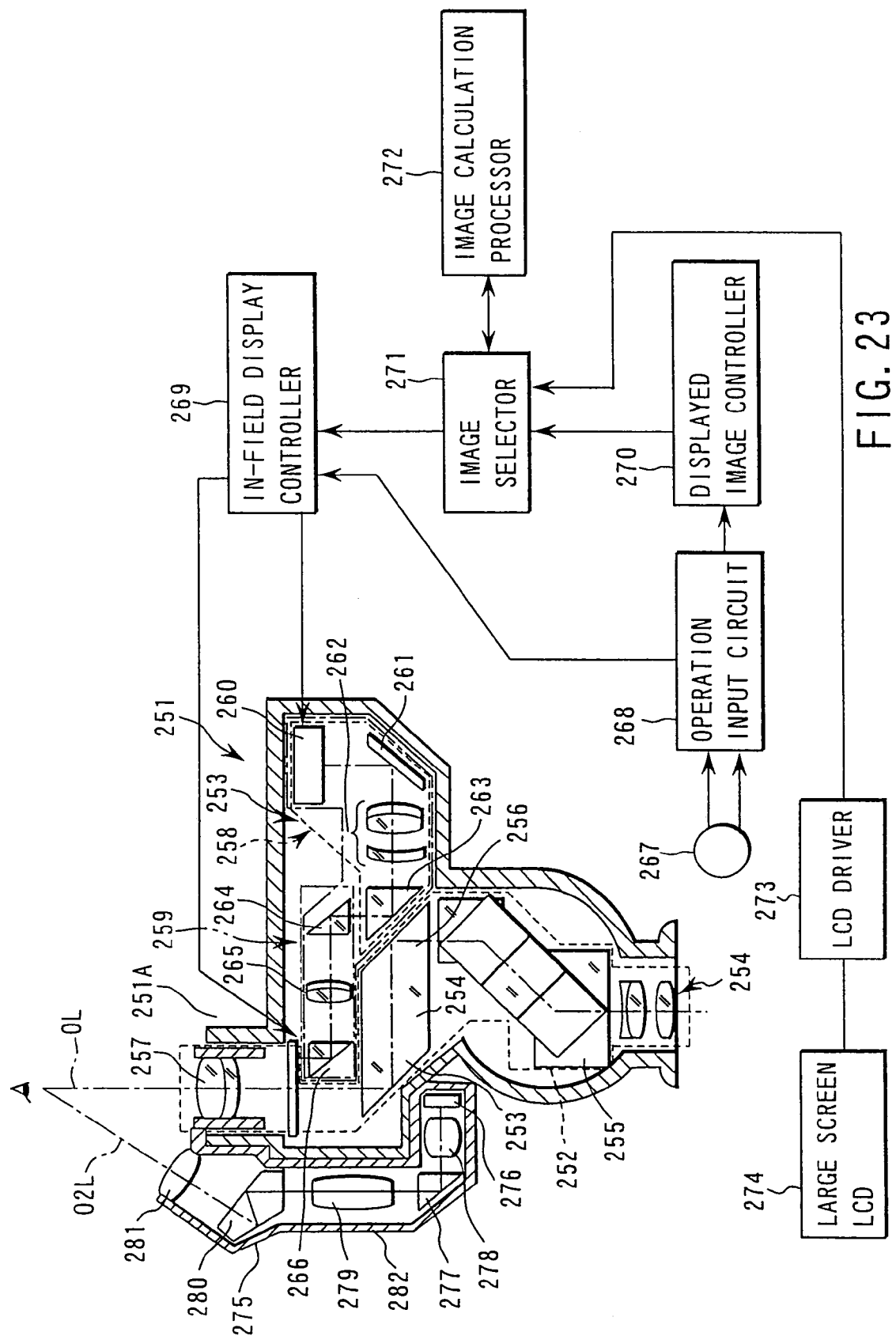
FIG. 23 is a schematic constitution diagram of a microscope body in the operation microscope apparatus of the sixth embodiment.

FIG. 23 shows a binocular lens tube 251 incorporated in the microscope body 202 of the operation microscope 201. Left and right observation light paths for stereoscopic observation are constituted in the binocular lens tube 251. Moreover, an objective lens (not shown) and variable power optical system (not shown) are disposed as the left and right observation light paths in the microscope body 202.

A right-eye optical observation system. 251A and a left-eye optical observation system (not shown) are disposed in the binocular lens tube 251. Additionally, FIG. 23 shows a constitution of a part of the right-eye observation optical system 251A seen from the side surface of the binocular lens tube 251. The left-eye optical observation system of the binocular lens tube 251 is constituted similarly to the right-eye optical observation system 251A, and a description thereof is omitted.

Moreover, a binocular lens tube optical system 252 for guiding the observation image of the operation microscope 201, and an optical image projection system 253 for observing arbitrary image information different from the observation image are disposed in the right-eye optical observation system 251A of the present embodiment. Here, an optical image forming system 254, image rotator 255, parallelogram prism 256, and optical eyepiece system 257 are disposed in the optical binocular lens tube system 252. The observation image of the operation microscope 201 incident upon the optical binocular lens tube system 252 is guided to the optical eyepiece system 257 via the image rotator 255 and parallelogram prism 256 in order from the optical image forming system 254.

Furthermore, the optical image projection system 253 is constituted of a fixed member 258 which is immobile with respect to eye distance adjustment of the binocular lens tube 251, and a movable member 259 moving integrally with an eyepiece image surface which moves during the eye distance adjustment of the binocular lens tube 251. Here, the fixed member 258 is constituted of an LCD display 260, mirror 261, optical collimating system 262, and prism 263. Furthermore, the movable member 259 is constituted of a fixed prism 264, optical image forming system 265, and movable prism 266. The movable prism 266 is disposed on the light path so that the prism can be inserted or detached by a mechanism moving motor (not shown). Moreover, the arbitrary image information displayed in the LCD display 260 is guided to the optical eyepiece system 257 via the mirror 261, optical collimating system 262, prism 263, fixed prism 264, optical image forming system 265, and movable prism 266 in order.

Furthermore, the observation image of the operation microscope 201 transmitted via the binocular optical lens tube system 252, and arbitrary image information transmitted via the optical image projection system 253 can simultaneously be observed in the eyepiece optical system 257.

Additionally, an in-field display operating switch 267 is disposed in a grip (not shown) of the operation microscope 201. This switch 267 is connected to an operation input circuit 268 constituted by a logic circuit.

This operation input circuit 268 is connected to an in-field display controller 269, and to an image selector 271 as image signal selection means via a display image controller 270. Here, the in-field display controller 269 is constituted of a drive control circuit of a motor (not shown) for controlling insertion/detachment of the movable prism 266 incorporated in the binocular lens tube 251, and a display control circuit of the LCD display 260. Furthermore, an output signal from the switch 267 is inputted into the operation input circuit 268, and a selecting operation signal outputted from the operation input circuit 268 is inputted to the in-field display controller 269 and image selector 271.

Moreover, the image selector 271 is connected to an image calculation processor 272, and a large screen LCD 274 via an LCD driver 273. Furthermore, a position detection display image signal outputted from the image calculation processor 272 and an image signal outputted from the LCD driver 273 are inputted to the image selector 271. Additionally, the image signal selected by the image selector 271 is sent to the in-field display controller 269.

Furthermore, a second image display unit 275 with a second optical observation system contained therein is disposed adjacent to the optical eyepiece system 257 in the binocular lens tube 251 of the sixth embodiment. The second optical observation system is constituted as follows. FIG. 23 shows only a left light path of the second optical observation system. Numeral 276 denotes a small-sized LCD monitor, controlled by a controller (not shown), for displaying the image of the endoscope or the like as the electronic image.

Furthermore, a prism 277 for reflecting the light axis O2L substantially by 90°, and a plurality of relay lenses 278, 279 are disposed on the outgoing light axis O2L from the LCD monitor 276.

Additionally, numeral 280 denotes a prism for deflecting the light axis reflected by the prism 277 in the direction of the observation light axis OL. A second optical eyepiece system 281 is optically disposed/connected on the outgoing light axis O2L of the prism 280. Moreover, the observation light axes OL and O2L intersect each other in the vicinity of an emission pupil position. Additionally, numeral 282 denotes an eyepiece housing in which the second optical observation system of the second image display unit 275 including the second optical eyepiece system 281 is integrally contained.

Figure 24:
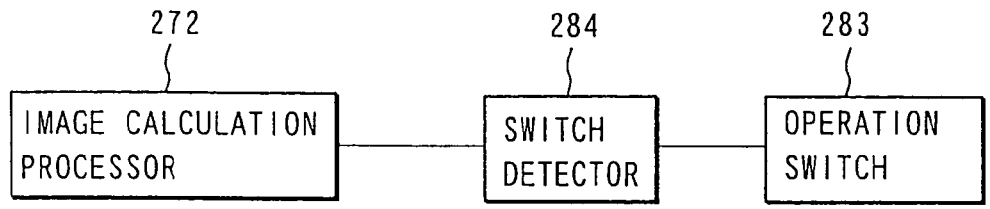
FIG. 24 is a block diagram showing a control system in the operation microscope apparatus of the sixth embodiment.

Furthermore, as shown in FIG. 24, the image calculation processor 272 is connected to an operation switch 283 disposed in the connection member 223 of the endoscope 221 via a switch detector 284.

Figure 25:
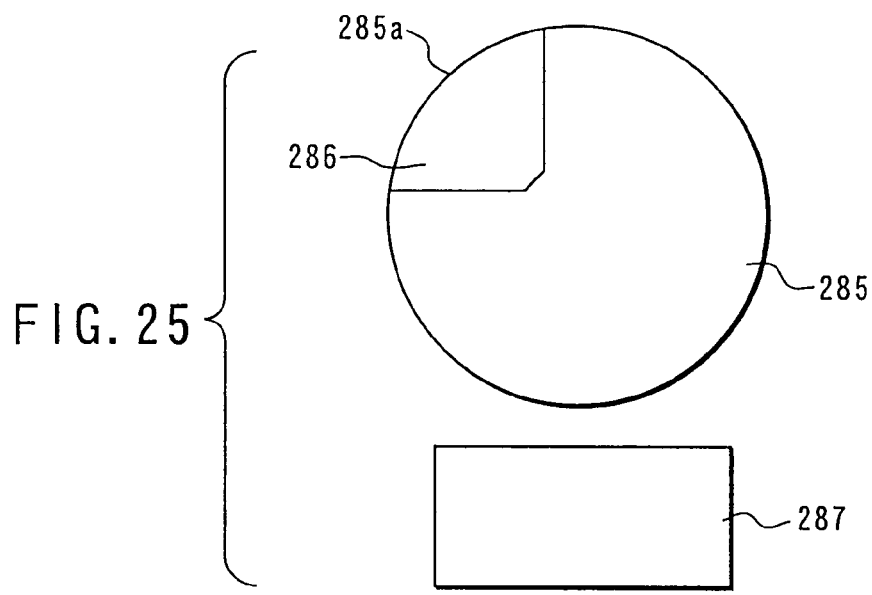
FIG. 25 is a diagram showing the microscope observation field in the operation microscope apparatus of the sixth embodiment.

As shown in FIG. 25, a small screen 285a, as an in-field display screen, is superimposed onto a part of a microscope observation field 285 displayed in the optical eyepiece system 257 of the binocular lens tube 251. Furthermore, a large screen 287 displayed in the second image display unit 275 is disposed in the vicinity of the microscope observation field 285. Additionally, an endoscope observation image 286 is displayed in the small screen 285a of the microscope observation field 285, and the electronic image by the LCD monitor 276 is displayed in the large screen 287.

Figure 26A:
FIG. 26A is an explanatory view showing a first image selection state by a switch detector in the operation microscope apparatus of the sixth embodiment.
Figure 26B:
FIG. 26B is an explanatory view showing a second image selection state by a switch detector in the operation microscope apparatus of the sixth embodiment.

Moreover, the operation switch 283 locks and unlocks the arm of the scope holder 224, and selects the images displayed in the large screen 287 and small screen 285a in accordance with the state of the switch detector 284 as shown in FIG. 26A or FIG. 26B.

Furthermore, when the operation switch 283 of the scope holder 224 is on (during movement), as shown in FIG. 28, the endoscope image P is displayed in the microscope observation field 285, and the endoscope observation image 286 is displayed in the small screen 285a. In this case, a state in which nothing is displayed is held in the large screen 287. Additionally, when the operation switch 283 of the scope holder 224 is off (during fixing), as shown in FIG. 27, the endoscope image P is displayed in the microscope observation field 285, and the endoscope observation image 286 is displayed in the large screen 286. In this case, the state in which nothing is displayed is held in the small screen 285a.

Additionally, the following effect is achieved in the aforementioned constitution. That is, in the sixth embodiment, a fixed/released state of the scope holder 224 is detected by the switch detector 284, and display modes of a plurality of display images can be changed for in-field display of the microscope observation field 285 in accordance with the fixed/released state of the scope holder 224. Therefore, since the in-field display screen of the microscope observation field 285 can be automatically changed in accordance with a usage state of the scope holder 224 without troubling the operating person, an operating time can be shortened, and fatigue of the operating person can be reduced. When the scope holder 224 moves, the endoscope image P is displayed in the microscope observation field 285, and the endoscope observation image 286 is displayed in the small screen 285a. Therefore, the operating person can simultaneously see the endoscope image and microscope observation image without moving the line of sight. In this case, nothing is displayed in the large screen 287. Therefore, no display image of the large screen 287 is possibly emitted into the eyes of the operating person who observes a moving state of the scope holder 224 in the microscope observation field 285, and the scope holder 224 can smoothly be moved.

Furthermore, when the scope holder 224 is fixed, the microscope observation image is not interrupted by the small screen 285a, and therefore the microscope observation image can be clearly and easily observed.

FIG. 29 to FIG. 32 show a seventh embodiment. The seventh embodiment is based on the system constitution of the operation microscope apparatus of the sixth embodiment, and is constituted by adding an image linked with navigation to the display mode. Additionally, the same constituting components as those of the sixth embodiment (see FIG. 21 to FIG. 28) are denoted by the same reference numerals, and description thereof is omitted.

FIG. 29 is a block diagram of the control system. As shown in FIG. 29, a camera control unit 288 is connected to the image calculation controller 272, and a digitizer 289 and microscope body controller 290 are connected to the image calculation controller 272 via a workstation 291.

Figure 30A:
FIG. 30A is an explanatory view showing the first image selection state by the switch detector in the operation microscope apparatus of the seventh embodiment.
Figure 30B:
FIG. 30B is an explanatory view showing the second image selection state by the switch detector in the operation microscope apparatus of the seventh embodiment.

Moreover, in the seventh embodiment, during locking/unlocking of the arm of the scope holder 224 by the operation switch 283, the image to be displayed in the large and small screens 287 and 285a is selectively changed in accordance with the state of the switch detector 284. The image is set to be selected as shown in FIG. 30A when the scope holder 224 is fixed, and as shown in FIG. 30B when the scope holder 224 moves.

Figure 32:
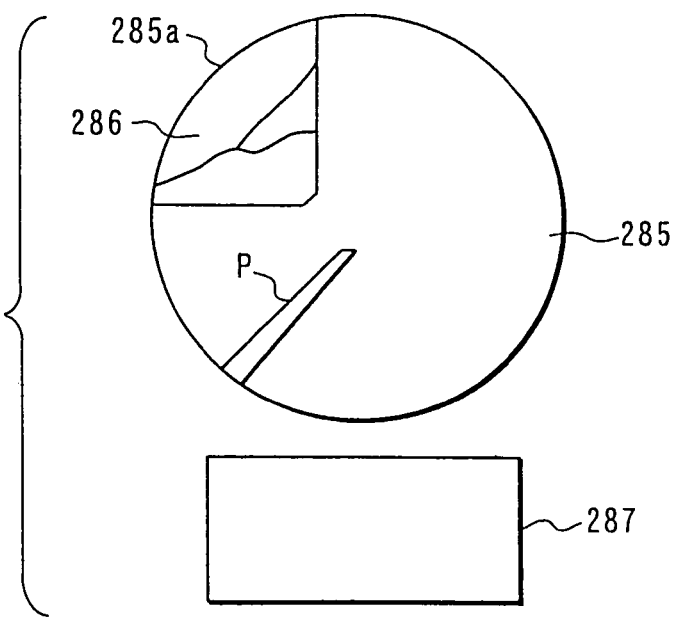
FIG. 32 is a diagram showing the microscope observation field during moving of the scope holder in the operation microscope apparatus of the seventh embodiment.

Moreover, in the seventh embodiment, when the operation switch 283 of the scope holder 224 is turned on, and the state of movement of the scope holder 224 is detected by the switch detector 284, as shown in FIG. 32, the endoscope image P is displayed in the microscope observation field 285 of the operation microscope 201, and the endoscope observation image 286 is displayed in the small screen 285*a*. In this case, nothing is displayed in the large screen 287. Additionally, the observation position of the scope holder 224 can be displayed in the large screen 287 during operation of the scope holder 224 (FIG. 32).

Figure 31:
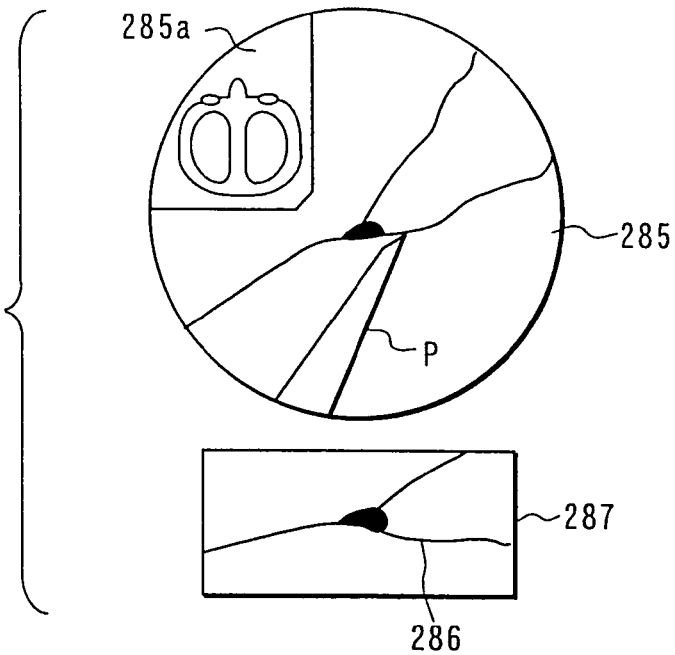
FIG. 31 is a diagram showing the microscope observation field during fixing of the scope holder in the operation microscope apparatus of the seventh embodiment.

Furthermore, when the operation switch 283 of the scope holder 224 is off (during fixing), as shown in FIG. 31, the endoscope image P is observed in the microscope observation field 285, a pre-operative image and scope holder observation position are displayed in the small screen 285*a*, and the endoscope observation image 286 is displayed in the large screen 287.

Additionally, the following effect is achieved in the aforementioned constitution. That is, in the seventh embodiment, since the screen can automatically be changed in accordance with the usage state of the scope holder 224 without troubling the operating person, the operating time can be shortened, and the fatigue of the operating person can be reduced.

When the scope holder 224 moves, as shown in FIG. 32, the endoscope image P is displayed in the microscope observation field 285 of the operation microscope 201, and the endoscope observation image 286 is displayed in the small screen 285*a*. Therefore, the operating person can simultaneously see the endoscope image and microscope image without moving the line of sight. In this case, nothing is displayed in the large screen 287. Therefore, no display image of the large screen 287 is possibly emitted into the eyes of the operating person who observes the moving state of the scope holder 224 in the microscope observation field 285, and the scope holder 224 can be smoothly moved.

Furthermore, when the scope holder 224 is fixed, as shown in FIG. 31, the endoscope image P is observed in the microscope observation field 285, the preoperative image and scope holder observation position are displayed in the small screen 285*a*, and the endoscope observation image 286 is displayed in the large screen 287. Therefore, the preoperative image and the endoscope image can be observed at the same time without interrupting the microscope observation.

FIG. 33 to FIG. 37 show an eighth embodiment. The eighth embodiment is constituted by adding an ultrasonic observation apparatus 300 to the system constitution of the operation microscope apparatus of the sixth embodiment (see FIG. 21 to FIG. 28) and seventh embodiment (see FIG. 29 to FIG. 32). In the present constitution, an observation/non-observation state of the ultrasonic observation apparatus 300 is detected, and the display modes of a plurality of display images for the display in the microscope observation field 285 are changed in accordance with the detected state. Additionally, in FIG. 33 to FIG. 37, the same constituting components as those of the sixth and seventh embodiments are denoted by the same reference numerals and description thereof is omitted.

Figure 33:
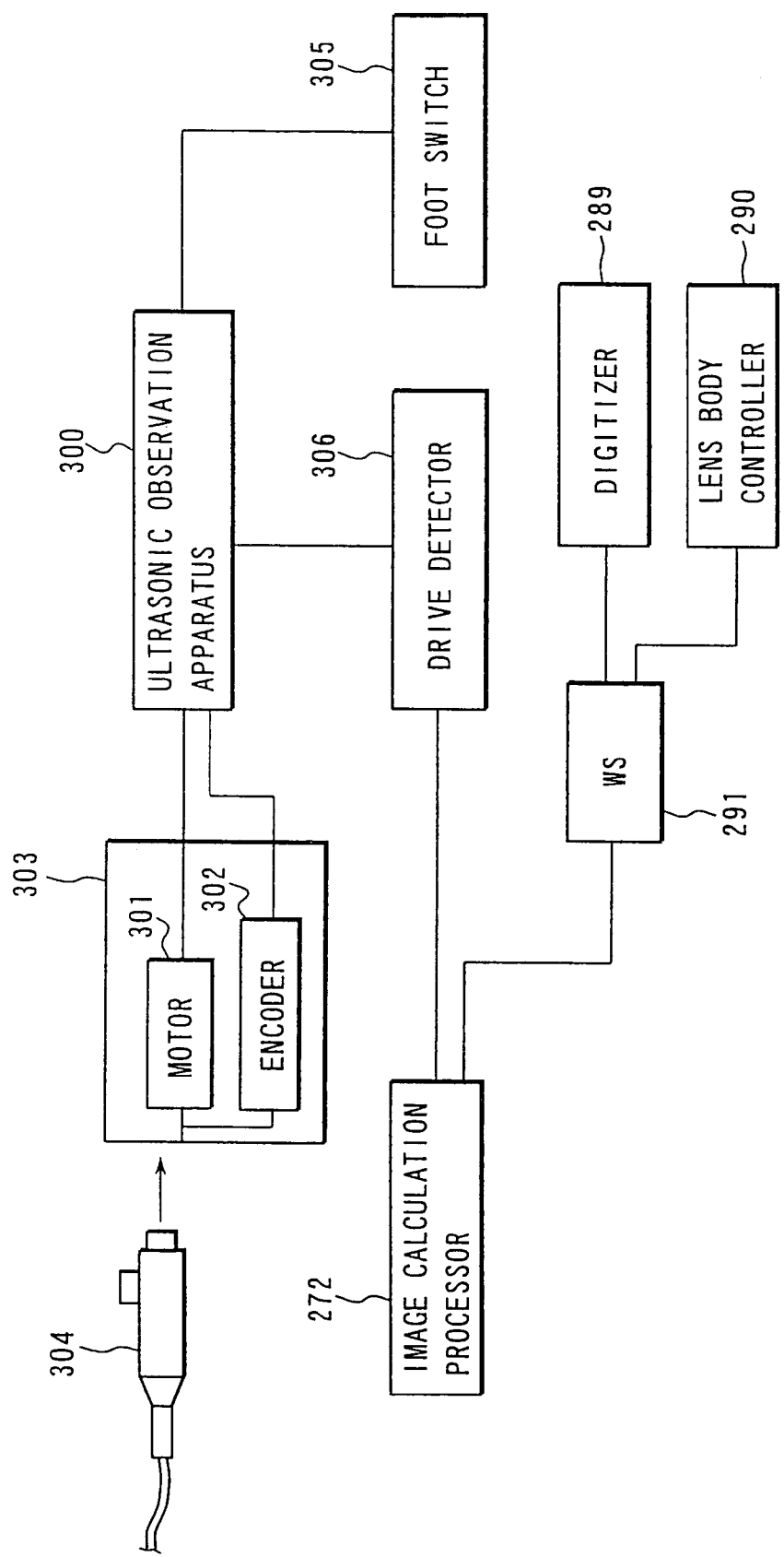
FIG. 33 is a block diagram of the control system in the operation microscope apparatus according to an eighth embodiment of the present invention.

FIG. 33 is a block diagram of an ultrasonic observation control system. The ultrasonic observation apparatus 300 is connected to ultrasonic drive means 303 including a motor 301 and encoder 302. An ultrasonic probe 304 is disconnectably connected to the ultrasonic drive means 303. The ultrasonic observation apparatus 300 includes a foot switch 305. The ultrasonic observation apparatus 300 is connected to the image calculation processor 272 via a drive detector 306. Moreover, the image to be displayed in in-field display means is selected and displayed based on a detection result of a drive state of the ultrasonic observation apparatus 300 detected by the drive detector 306.

Figures 34, 35A, 35B:
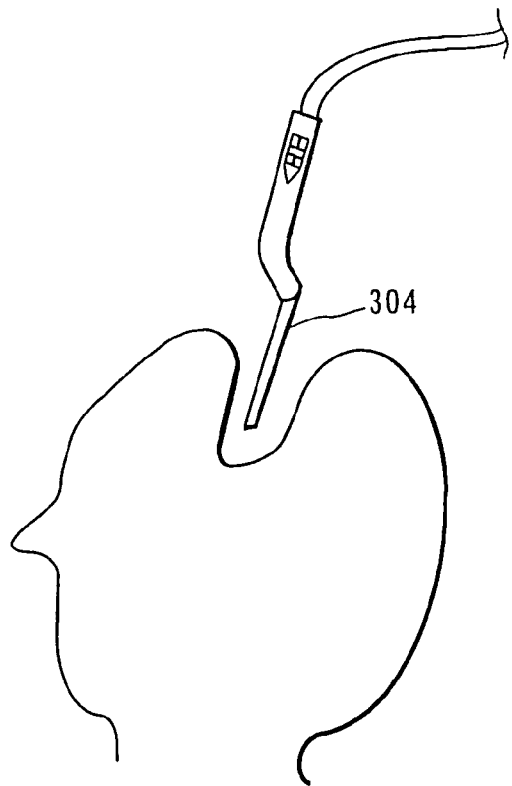
FIG. 34 is a schematic constitution diagram showing a usage state of an ultrasonic probe in the operation microscope apparatus of the eighth embodiment.
FIG. 35A is an explanatory view showing the image selection state during ultrasonic observation in the operation microscope apparatus of the eighth embodiment.
FIG. 35B is an explanatory view showing the image selection state during discontinuation of ultrasonic observation in the operation microscope apparatus of the eighth embodiment.

FIG. 34 shows a state in which the ultrasonic probe 304 is inserted into a patient's operating field, and an affected portion in the operating field is observed by the ultrasonic probe 304.

Moreover, during the use of the ultrasonic probe 304 of the eighth embodiment, the drive detector 306 detects the drive state of the ultrasonic observation apparatus 300. Moreover, when the foot switch 305 is turned on and the ultrasonic observation apparatus 300 is driven, that is, when an ultrasonic observation state is detected by the drive detector 306, the state of the apparatus is changed as shown in FIG. 35A. That is, the preoperative image (ultrasonic observer plane image) is displayed in the small screen 285*a* in the microscope observation field 285, and an ultrasonic observation image N is displayed in the large screen 287. Furthermore, when the foot switch 305 is turned off and the ultrasonic observation apparatus 300 is stopped, that is, when an ultrasonic observation discontinued state is detected by the drive detector 306, the state of the apparatus is changed as shown in FIG. 35B. That is, the preoperative image (the entire head image) is displayed in the small screen 285*a* in the microscope observation field 285, and the ultrasonic observation image N is displayed in the large screen 287.

Figure 37:
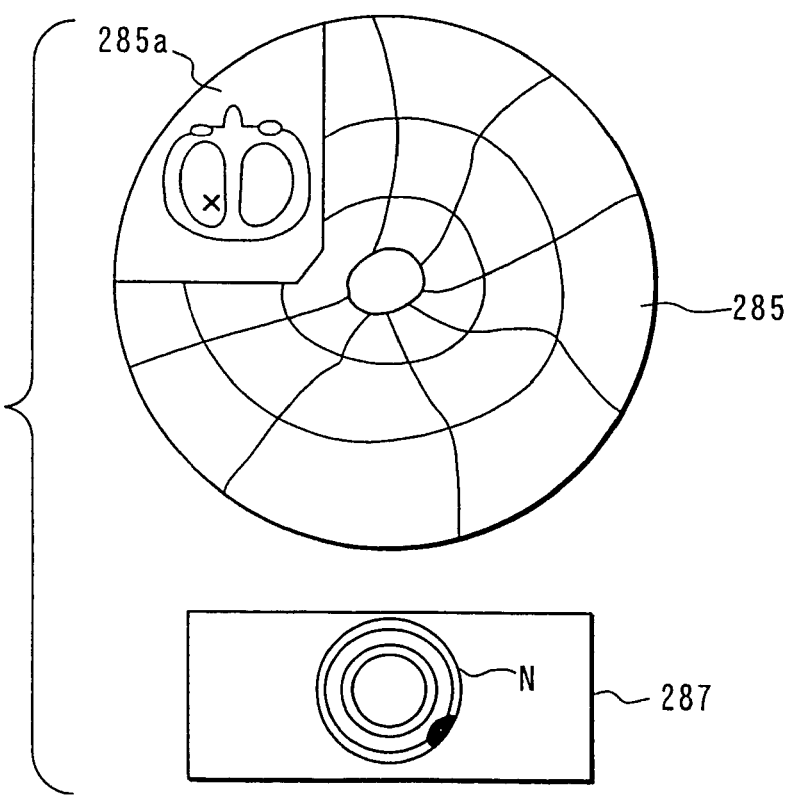
FIG. 37 is a diagram showing the microscope observation field during ultrasonic observation in the operation microscope apparatus of the eighth embodiment.

Moreover, in the eighth embodiment, when the ultrasonic observation state is detected by the drive detector 306, as shown in FIG. 37, the preoperative image (ultrasonic observer plane image) is displayed in the small screen 285*a* in the microscope observation field 285, and the ultrasonic observation image N is displayed in the large screen 287.

Figure 36:
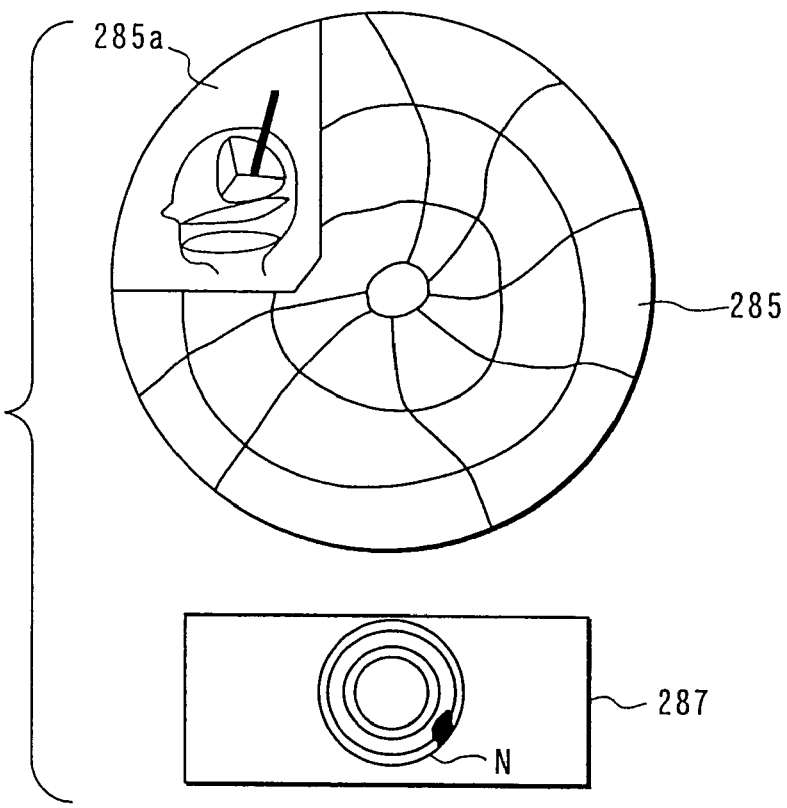
FIG. 36 is a diagram showing the microscope observation field during discontinuation of ultrasonic observation in the operation microscope apparatus of the eighth embodiment.

Furthermore, when the ultrasonic observation discontinued state is detected by the drive detector 306, as shown in FIG. 36, the preoperative image (the entire head image) is displayed in the small screen 285*a* in the microscope observation field 285, and the ultrasonic observation image N is displayed in the large screen 287. Additionally, the position of an ultrasonic probe or a tomographic image direction is displayed in the preoperative image.

Therefore, in the eighth embodiment, since the screen displayed in the small screen 285*a* and large screen 287 in the microscope observation field 285 can be automatically changed in accordance with the usage state of the ultrasonic probe 304 without troubling the operating person during use of the ultrasonic probe 304, the operating time can be shortened, and the fatigue of the operating person can be reduced during use of the ultrasonic probe 304. Moreover, during ultrasonic observation, the microscope observation image can be compared with the ultrasonic observation image N without discontinuing the microscope observation. Furthermore, in a case other than ultrasonic observation, the position of the ultrasonic probe 304 is confirmed, and the ultrasonic probe 304 can be positioned in a position desired by the operating person.

FIG. 38 to FIG. 43 show a ninth embodiment. The ninth embodiment is constituted by changing the system constitution of the operation microscope apparatus of the eighth embodiment (see FIG. 33 to FIG. 37) as follows. Additionally, in FIG. 38 to FIG. 43, the same constituting components as those of the eight embodiment are denoted by the same reference numerals, and description thereof is omitted.

In the constitution of the ninth embodiment, a function of a foot switch 310 is allotted to control the image source, in accordance with the image source (endoscope, ultrasonic wave, and the like) selected for the in-field display of the microscope observation field 285. That is, when a plurality of apparatuses, for example, the endoscope and ultrasonic probe are used together, the image source is changed by the foot switch 310 of the operation microscope without selecting the image source displayed in the in-field display means.

Figure 38:
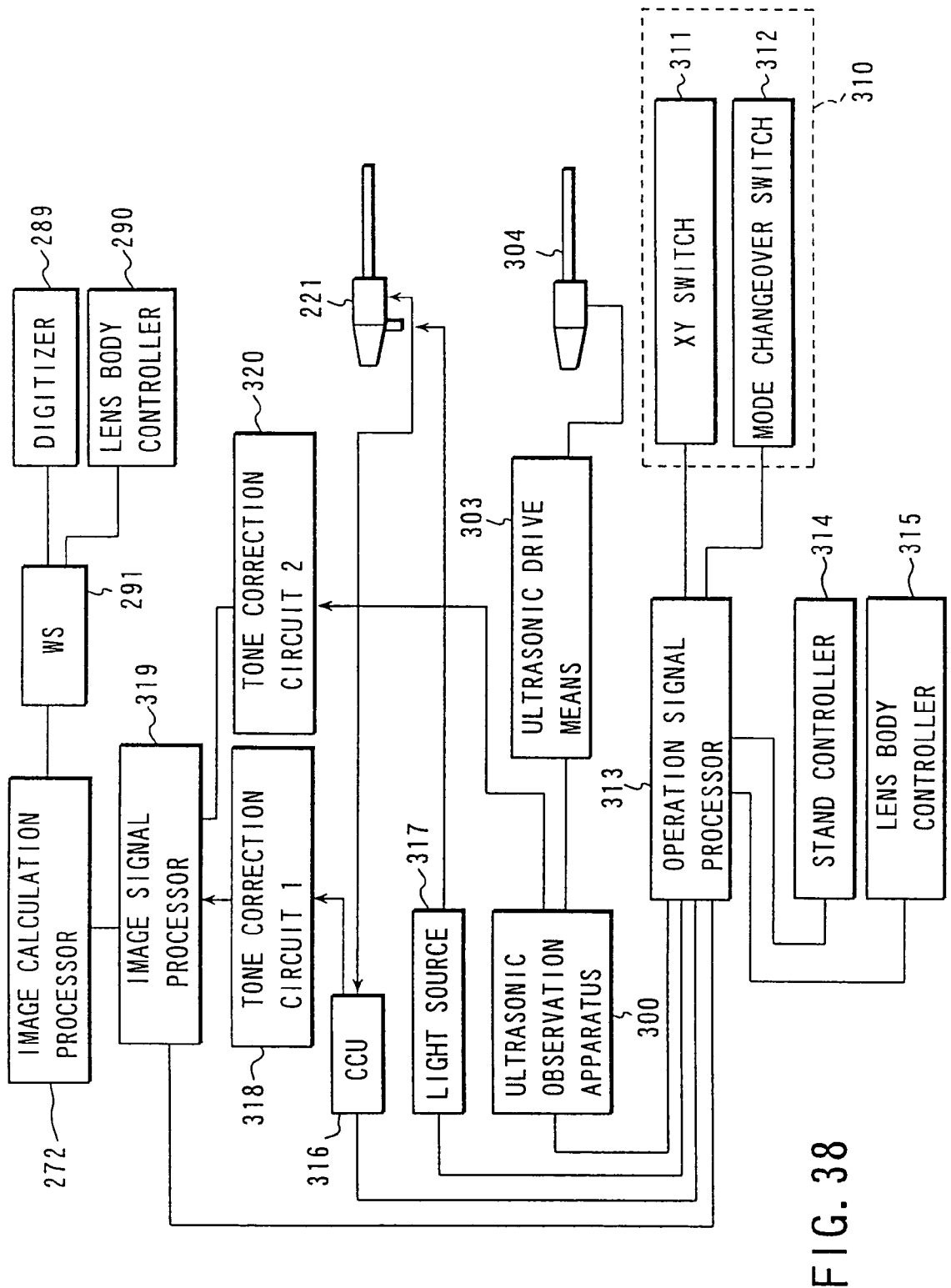
FIG. 38 is a block diagram of the control system in the operation microscope apparatus according to a ninth embodiment of the present invention.

As shown in FIG. 38, the foot switch 310 of the operation microscope according to the ninth embodiment includes an XY switch 311 and a mode changeover switch 312. The foot switch 310 is connected to an operation signal processor 313, and the operation signal processor 313 is connected to a stand controller 314 and microscope body controller 315 of the operation microscope.

The operation signal processor 313 is connected to the endoscope 221 via a camera control unit 316 and light source apparatus 317. Furthermore, the operation signal processor 313 is connected to the ultrasonic probe 304 via the ultrasonic observation apparatus 300 and ultrasonic drive means 303.

Moreover, the camera control unit 316 is connected to an image signal processor 319 via a first tone correction circuit 318. The ultrasonic observation apparatus 300 is connected to the image signal processor 319 via a second tone correction circuit 320. The image signal processor 319 is connected to the image calculation processor 272, and the operation signal processor 313.

Furthermore, when the endoscope 221 is used, the image is displayed in the in-field display means via the first tone correction circuit 318, and the image signal processor 319 detects that the endoscope image is displayed in the in-field display means.

In this state, when the operating person turns on the mode changeover switch 312 of the foot switch 310, the operation signal processor 313 changes to endoscope control from operation microscope control. Moreover, when the XY switch 311 of the foot switch 310 is turned on, zoom, focus, and light source of the endoscope 221 can be adjusted. This also applies to ultrasonic observation. When the operating person turns on the mode changeover switch 312 of the foot switch 310, the operation signal processor 313 changes to ultrasonic probe control from the operation microscope control.

Therefore, since the observation apparatus can be operated without selecting the image source, the operating person is not troubled. Moreover, even when the endoscope 221 and ultrasonic probe 304 are used as the observation apparatus, color reproduction is performed in accordance with the observation apparatus and in-field display means. Therefore, as it is unnecessary to change the setting for the display, the operating time can be shortened, and the operating person's fatigue can be reduced.

FIG. 39 and FIG. 40 show the microscope observation field 285. When the endoscope 221 is used, as shown in FIG. 39, the endoscope image P is observed in the field 285, and the endoscope observation image M is superimposed/displayed in the small screen 285a.

Moreover, when the ultrasonic probe 304 is used, as shown in FIG. 40, an ultrasonic probe image R is observed in the field 285, and the ultrasonic probe observation image N is displayed in the small screen 285a.

FIG. 41 shows the foot switch 310, FIG. 42 shows a process content when the endoscope observation image M is displayed in the microscope observation field 285, and FIG. 43 shows a content when the ultrasonic probe observation image N is displayed in the microscope observation field 285.

Figure 46:
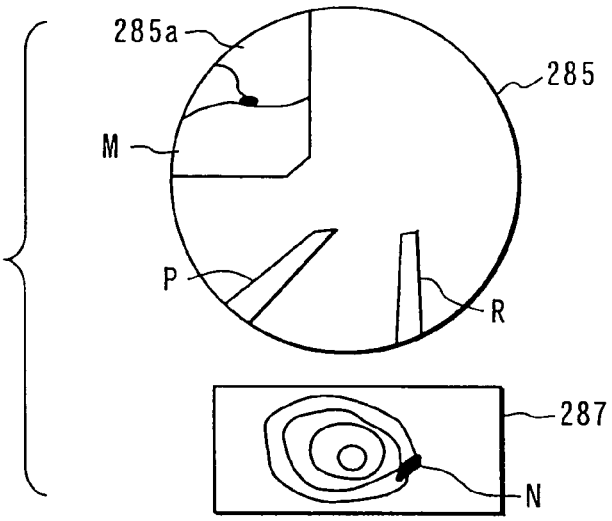
FIG. 46 is a diagram showing another example of the superimposed display state of the microscope observation field in the operation microscope apparatus of the tenth embodiment.

Here, when the endoscope observation image M is displayed in the microscope observation field 285, the XY switch 311 of the foot switch 310 is operated as shown in FIG. 42.
X+: endoscope zoom-up
X−: endoscope zoom-down
Y+: endoscope light amount up
Y−: endoscope light amount down Moreover, when the ultrasonic probe observation image N is displayed in the microscope observation field 285, the XY switch 311 of the foot switch 310 is operated as shown in FIG. 43.
X+: scan start
X−: scan stop
Y+: display image right rotation
Y−: display image left rotation FIG. 44 to FIG. 46 show a tenth embodiment. The tenth embodiment is constituted by adding the LCD driver 273 for display in the large screen and LCD 274 for the large screen to the system constitution of the operation microscope apparatus of the ninth embodiment (see FIG. 38 to FIG. 43) as shown in FIG. 44. Furthermore, a tone setting table 321 for performing color reproduction of the large screen of the in-field display means in accordance with the small screen is added.

In the tenth embodiment, as shown in FIG. 45, the endoscope image P is observed in the microscope observation field 285, and the endoscope observation image M is superimposed/displayed in the small screen 285a as a part of the field 285. In this case, nothing is displayed in the large screen 287.

Furthermore, in FIG. 46, both the endoscope image P and the ultrasonic probe image R are observed in the microscope observation field 285, the endoscope observation image M is superimposed/displayed in the small screen 285a as a part of the field, and the ultrasonic image N is displayed in the large screen 287. In this case, color reproduction of the large screen 287 is performed in accordance with the small screen 285a by the tone setting table 321.

Figure 47:
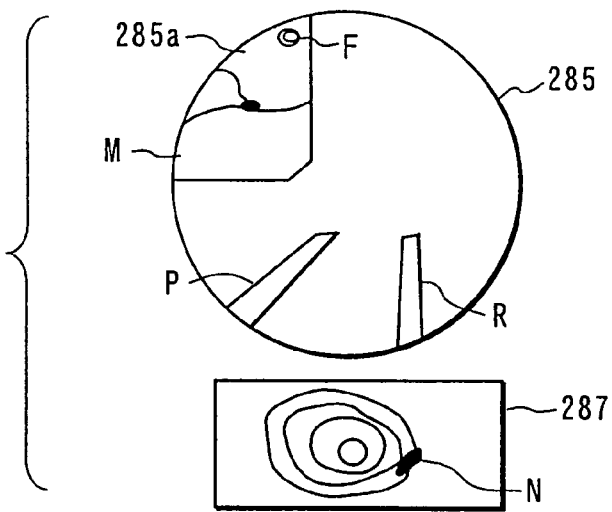
FIG. 47 is a diagram showing one example of the microscope observation field in the operation microscope apparatus according to an eleventh embodiment of the present invention.
Figure 48:
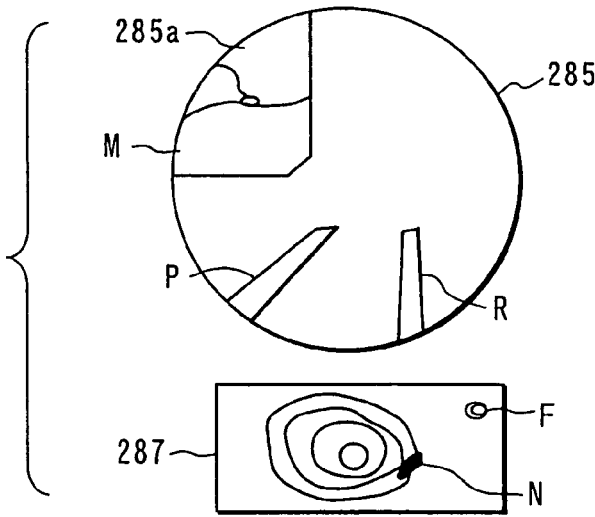
FIG. 48 is a diagram showing another example of the microscope observation field in the operation microscope apparatus of the eleventh embodiment.
Figure 49:
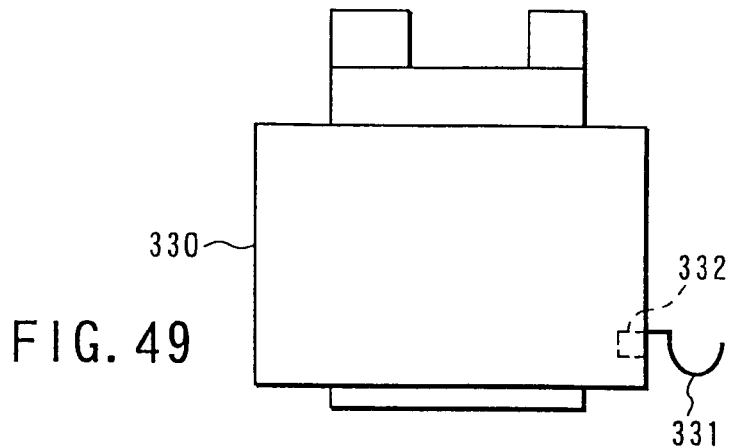
FIG. 49 is a front view showing the microscope body of the operation microscope apparatus according to a twelfth embodiment of the present invention.

Moreover, FIG. 47 and to FIG. 48 show an eleventh embodiment. In addition to the system constitution of the operation microscope apparatus of the ninth embodiment (see FIG. 38 to FIG. 43), in the constitution of the eleventh embodiment, an identification mark is displayed in an image to which a function of the foot switch 310 (see FIG. 41) is allotted. Furthermore, in the eleventh embodiment, every time the mode changeover switch 312 of the foot switch 310 is pressed, an endoscope operation, ultrasonic observation apparatus operation, and operation microscope operation are changed thereamong.

Moreover, in the eleventh embodiment, as shown in FIG. 47, both the endoscope image P and the ultrasonic probe image R are observed in the microscope observation field 285, the endoscope observation image M is superimposed/displayed in the small screen 285a, and the ultrasonic image N is displayed in the large screen 287. In this state, a mark F is displayed in a part of the endoscope observation image M to indicate that the image is controlled by the foot switch 310.

Furthermore, in FIG. 48, both the endoscope image P and the ultrasonic probe image R are observed in the microscope observation field 285, the endoscope observation image M is superimposed/displayed in the small screen 285a, and the ultrasonic image N is displayed in the large screen 287. Here, the mark F is displayed in a part of the ultrasonic image N of the large screen 287 to indicate that the image is controlled by the foot switch 310.

FIG. 49 to FIG. 52 show a twelfth embodiment. In the constitution of the twelfth embodiment, an endoscope holding hook 331 for hooking and holding the endoscope 221 is disposed in a microscope body 330 of the operation microscope shown in FIG. 49, it is detected whether or not the endoscope 221 is held by the holding hook 331, and the operation microscope and in-field display apparatus are controlled. Here, a holding switch 332 is disposed in a fixed portion of the endoscope holding hook 331. Moreover, when the endoscope 221 is hooked and held onto the hook 331 of the microscope body 330, the holding switch 332 is turned on.

Figure 50:
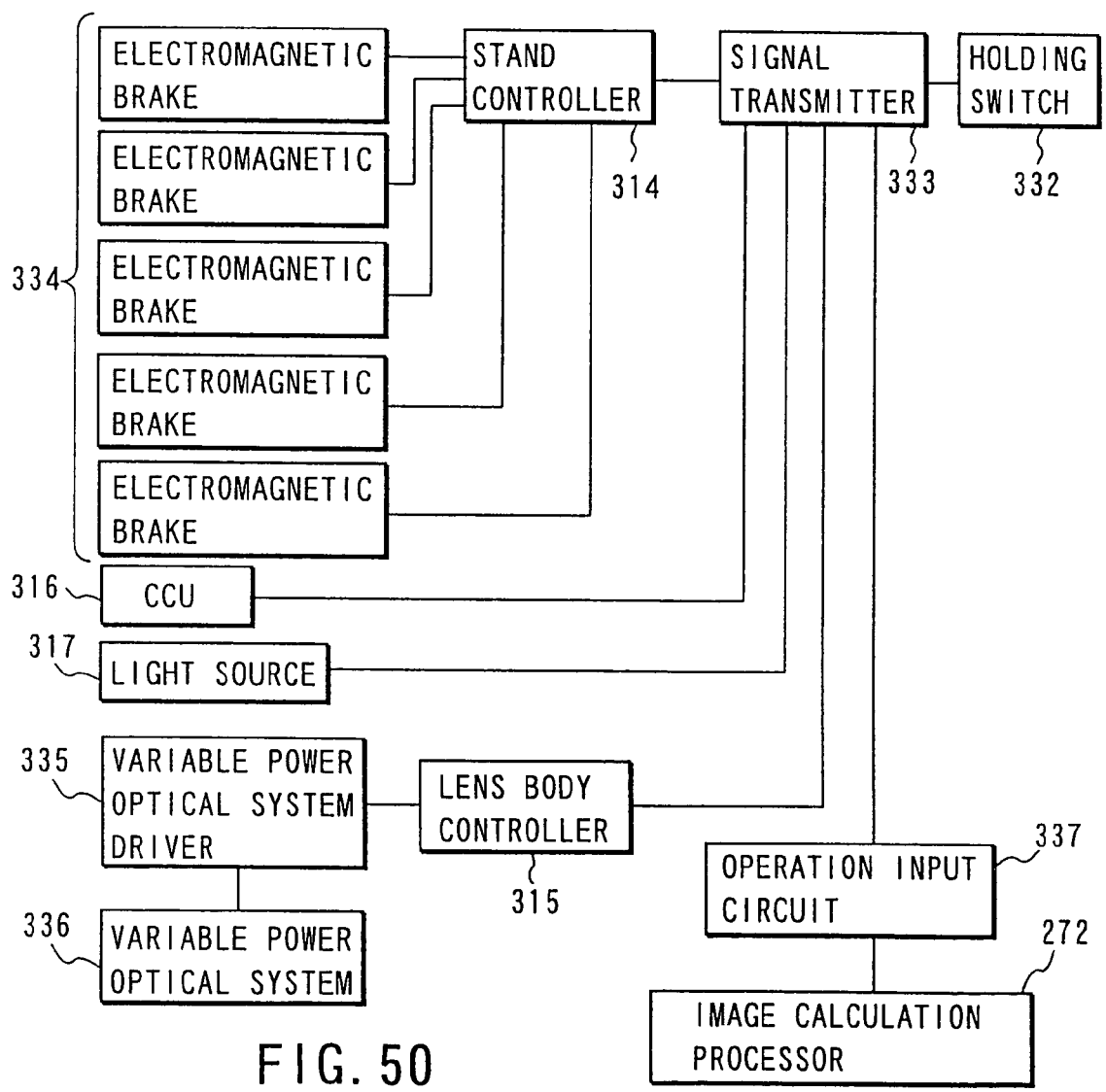
FIG. 50 is a block diagram of the control system of the operation microscope apparatus of the twelfth embodiment.

Moreover, FIG. 50 is a block diagram of the control system of the operation microscope. Here, the holding switch 332 is connected to the stand controller 314 and microscope body controller 315 via a signal transmitter 333. The stand controller 314 is connected to respective electromagnetic brakes 334 disposed in arm joints. The microscope body controller 315 is connected to a variable power optical system driver 335 of a variable power optical system 336. Furthermore, the signal transmitter 333 is connected to the camera control unit 316 and light source apparatus 317, and to the image calculation processor 272 via an operation input circuit 337.

Furthermore, when the operating person removes the endoscope 221 from the hook 331, the holding switch 332 is turned on, and a signal flows to the stand controller 314 via the signal transmitter 333. Thereby, the respective electromagnetic brakes 334 operate to lock the respective arms. Additionally, the variable power optical system driver 335 operates via the microscope body controller 315 so that a magnification of the variable power optical system 336 is minimized. The light source apparatus 317 and camera control unit 316 of the endoscope 221 are started up to obtain a state in which endoscope observation is possible.

Therefore, when the endoscope 221 is unused, that is, when the endoscope 221 is held by the hook 331, and even when the operation microscope stand is moved, the endoscope 221 is prevented from contacting or breaking the operation microscope. Moreover, since the endoscope 221 can be set without troubling the operating person, the operating person's fatigue can be reduced, and the operating time can also be shortened.

Figure 51:
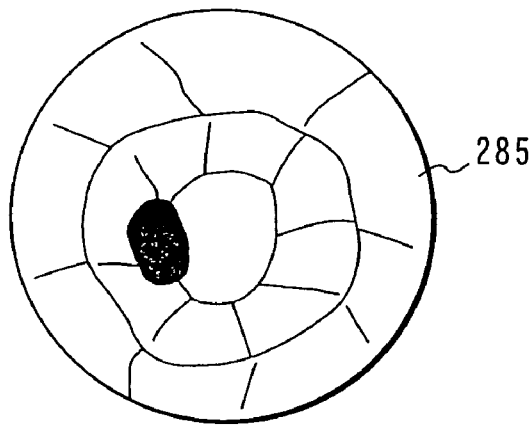
FIG. 51 is a diagram showing one example of the microscope observation field in the operation microscope apparatus of the twelfth embodiment.
Figure 52:
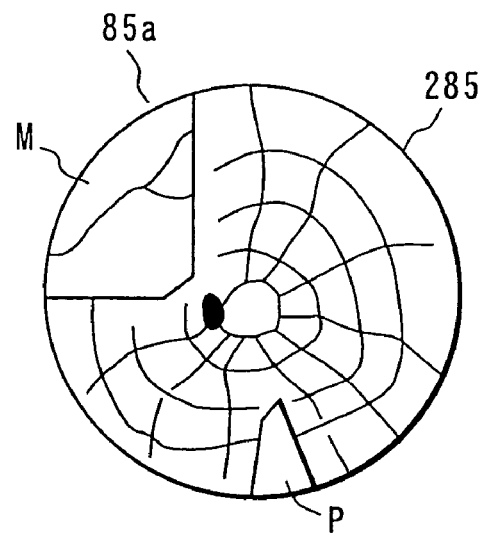
FIG. 52 is a diagram showing another example of the microscope observation field in the operation microscope apparatus of the twelfth embodiment.

Additionally, FIG. 51 shows the microscope observation field 285 of a state in which the endoscope 221 is caught by the hook 331, the endoscope 221 is unused and the variable power optical system 336 has a maximum magnification. Moreover, FIG. 52 shows the microscope observation field 285 of a state in which the endoscope 221 is used and the variable power optical system 336 has a minimum magnification. Here, the endoscope image P is displayed in the microscope observation field 285, and the endoscope observation image M is superimposed/displayed in the small screen 285a.

Figure 54:
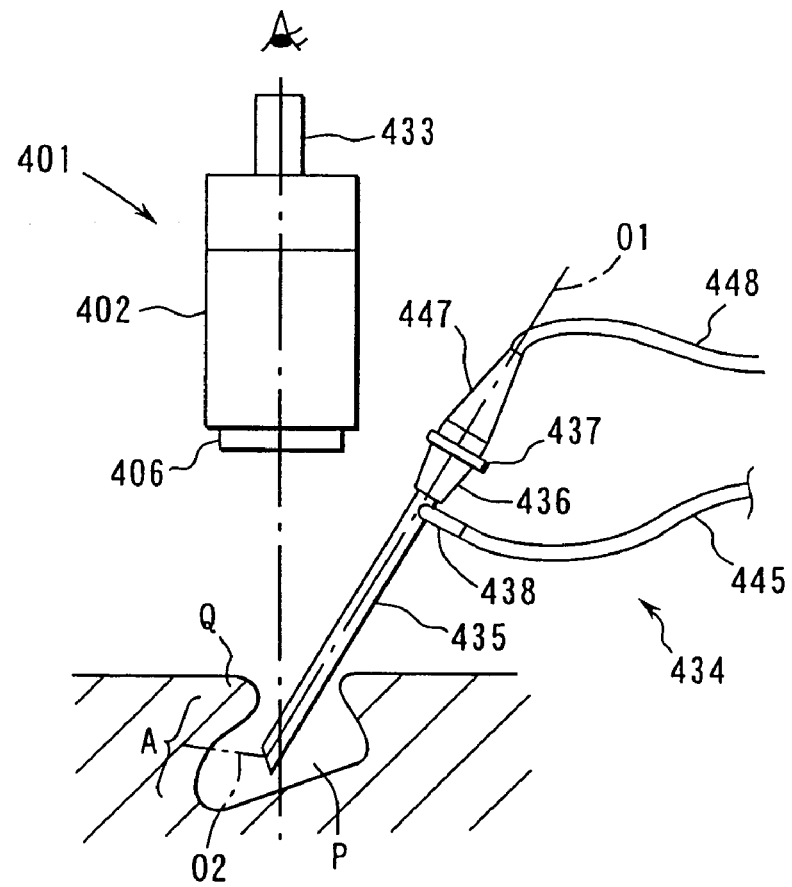
FIG. 54 is a schematic constitution diagram of the main part showing a state in which an insertion member tip end of the rigid endoscope used together with the operation microscope of the thirteenth embodiment is inserted into a pore of the portion subjected to the operation.
Figure 53A:
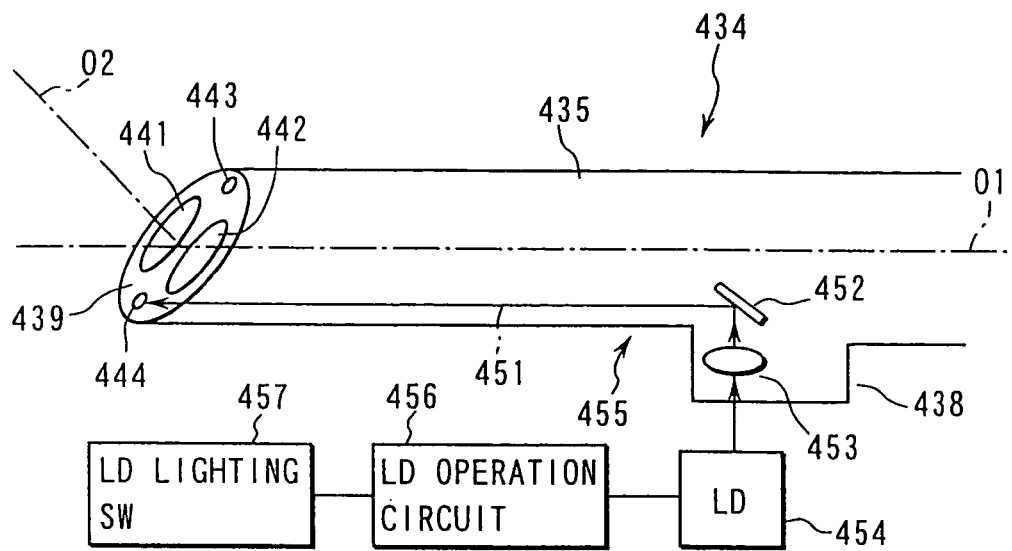
FIG. 53A is a schematic constitution diagram of a main part of a rigid endoscope used together with the operation microscope according to a thirteenth embodiment of the present invention.

Moreover, FIG. 53A to FIG. 60 show a thirteenth embodiment of the present invention. In the thirteenth embodiment, a rigid endoscope 434 used together with an operation microscope 401 as shown in FIG. 54 is constituted as shown in FIG. 53A. A tip end slope 439 obliquely intersecting an insertion axis (center line) O1 of an insertion member 435 is formed in a tip end of the insertion member 435 of the rigid endoscope 434. Here, an intersection angle between a center line O2 of the tip end slope 439 and the insertion axis O1 of the insertion member 435 is set to a constant angle α.

Furthermore, an objective lens 441, a lighting lens 442, and two projection windows (projection means) 443, 444 are disposed in the tip end slope 439. Thereby, the observation light axis O2 of the objective lens 441 is set to intersect the insertion axis O1 of the insertion member 435 at the constant intersection angle α.

Moreover, a relay lens (not shown) is disposed in the insertion member 435. Furthermore, the objective lens 441, relay lens, and eyepiece member 437 are optically connected to one another.

Furthermore, a tip end of a light guide cable (not shown) is disposed opposite to a lens surface inside the lighting lens 442. A base end of the light guide cable is connected to a light guide base 438 disposed at a base end of the insertion member 435 as shown in FIG. 54.

One end of a light guide 445 is connected to the light guide base 438. The other end of the light guide 445 is connected to a light source apparatus (not shown). Moreover, a lighting light emitted from the light source apparatus is guided to the light guide cable of the light guide base 438 from the light guide 445, and an operative portion P is irradiated with the lighting light guided by the light guide cable from the lighting lens 442.

Moreover, a TV camera 447 for photographing the observation image of the rigid endoscope 434 is connected to the eyepiece member 437 of the rigid endoscope 434. One end of a camera cable 448 is connected to the TV camera 447. The other end of the camera cable 448 is connected to an input end of a camera control unit (CCU) 449 (shown in FIG. 53B) for converting an electric signal of the observation image photographed by the rigid endoscope 434 to an image signal.

One projection window 443 of two projection windows 443, 444 of the tip end slope 439 in the insertion member 435 of the rigid endoscope 434 is disposed on a base end of the tip end slope 439, and the other projection window 444 is disposed on a tip end of the tip end slope 439.

Furthermore, one end of a light guide cable 451 for guiding an irradiation light for an index to two projection windows 443, 444 is connected into the insertion member 435. The other end of the light guide cable 451 is disposed in a part which is opposite to a reflective mirror 452 from an axial direction of the insertion member 435.

Additionally, in the light guide base 438, an image forming lens 453 is disposed in a part opposite to the reflective mirror 452 from a direction crossing at right angles to an axial direction of the insertion member 435. Furthermore, two laser diodes (light emission means) 454 as a light source for guiding the indexing irradiation light to the projection windows 443, 444 are disposed in the light source apparatus. Additionally, the indexing irradiation light emitted from two laser diodes 454 in the light source apparatus is guided to the image forming lens 453 of the light guide base 438 via the light guide 445. Furthermore, light guide means 455 for guiding the respective indexing irradiation lights to two projection windows 443, 444 via the reflective mirror 452 and light guide cable 451 is constituted. Since respective constitutions of the light guide means 455 for guiding the indexing irradiation light to two projection windows 443, 444 are the same, only the projection window 444 side light guide means 455 is shown in FIG. 53A.

Figure 55:
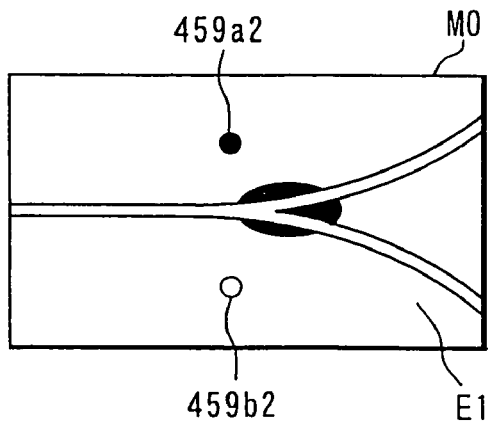
FIG. 55 is a plan view showing image information in which an emission index is displayed in the observation image of the rigid endoscope used together with the operation microscope of the thirteenth embodiment.

Here, laser diodes having different wavelengths are used in two laser diodes 454 in the light source apparatus. Thereby, the indexing irradiation lights having different colors are guided to the respective projection windows 443, 444, the projection windows 443, 444 emit the indexing irradiation lights having different colors, and emission indexes 459a, 459b are projected as shown in FIG. 55.

Moreover, a laser diode operation circuit 456 is connected to the laser diode 454. The laser diode operation circuit 456 is connected to a laser diode lighting switch 457. Furthermore, when two laser diodes 454 in the light source apparatus are turned on, the irradiation light as the index is guided in parallel with the observation light axis O2 of the objective lens 441 from two projection windows 443, 444 of the tip end slope 439 in the insertion member 435 of the rigid endoscope 434, and the emission indexes 459a, 459b are projected to the operative portion P.

Figure 59:
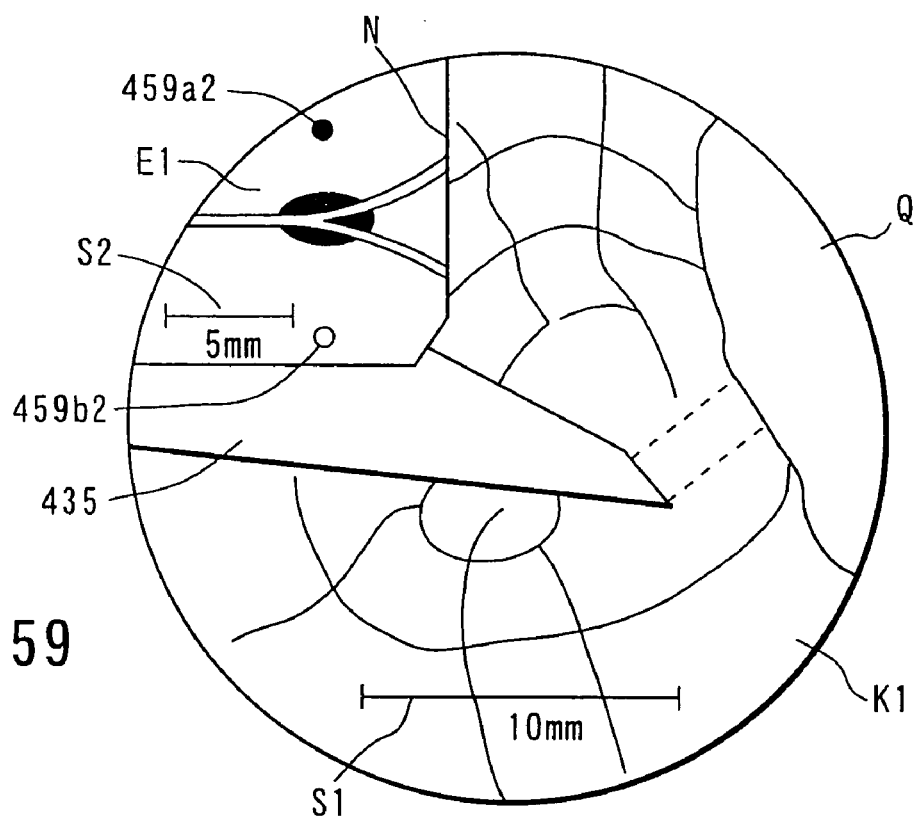
FIG. 59 is a plan view showing the observation image of the operation microscope displayed in a field of view of the operation microscope according to the thirteenth embodiment, and the image in which the scale having an appropriate length with respect to a diameter of microscope field of view and the character are displayed in the observation image of the rigid endoscope displayed in a sub-screen.

Furthermore, in the thirteenth embodiment, a scale generation apparatus 461 is disposed for generating scales S1, S2 having appropriate lengths, and characters indicating the lengths with respect to a field diameter of the microscope field in an observation image K1 of the operation microscope 401 displayed in a field of an eyepiece lens 410 of an eyepiece lens tube 433 of the operation microscope 401, and an observation image E1 (in-field display image) of the rigid endoscope 434 displayed in a sub-screen N inserted into the microscope observation image K1 as shown in FIG. 59.

Figure 53B:
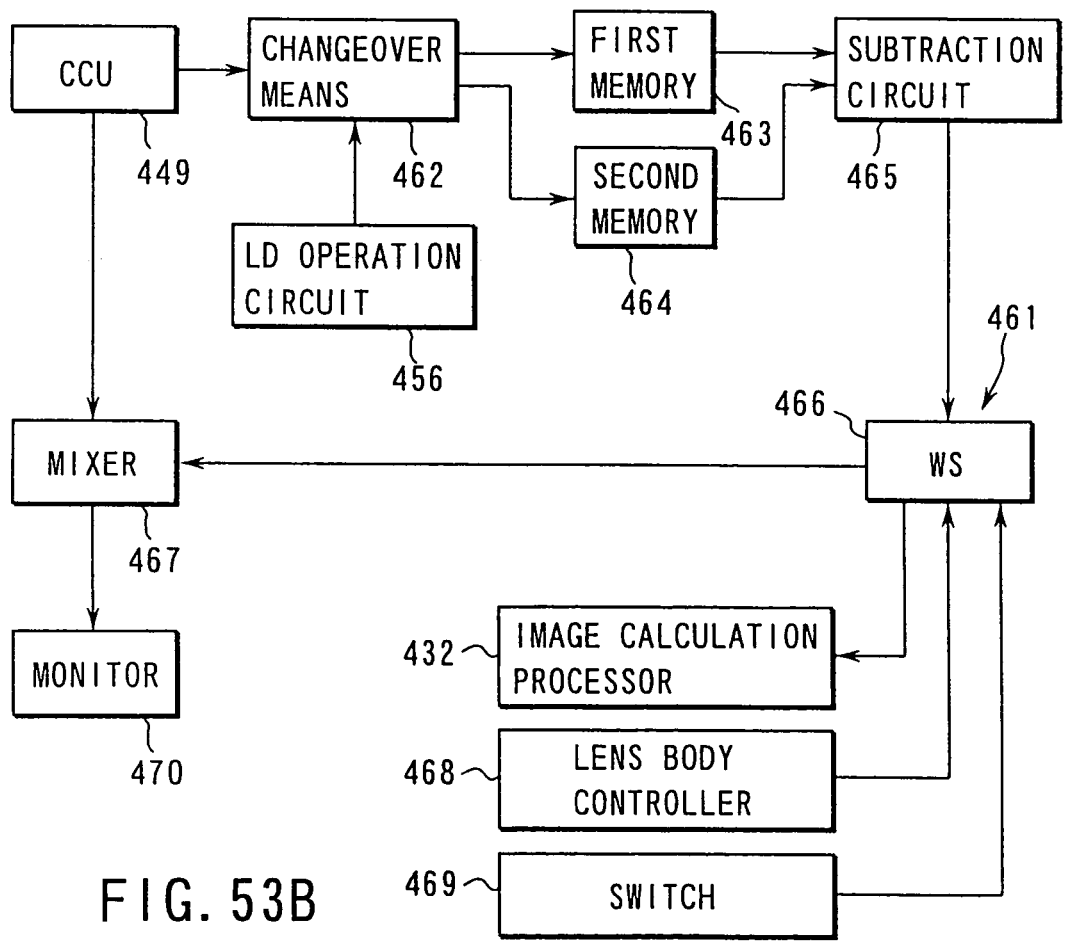
FIG. 53B is a schematic constitution diagram showing a scale generation apparatus in the operation microscope of the thirteenth embodiment.

In the scale generation apparatus 461, a control circuit is connected to the CCU 449 of the operation microscope 401 as shown in FIG. 53B. Changeover means 462 connected to the CCU 449 is disposed in the control circuit. The changeover means 462 is connected to the laser diode operation circuit 456, first memory 463, and second memory 464. Here, the changeover means 462 has a function of detecting an operation state of the laser diode operation circuit 456, and changing an outputting memory to either the first memory 463 or the second memory 464, and a function of transmitting the image signal.

Furthermore, a subtraction circuit 465 for subtracting information of the first and second memories 463 and 464 is connected to the first memory 463 and second memory 464. The subtraction circuit 465 is connected to a workstation 466.

The workstation 466 is connected to: a mixer 467 for synthesizing the image signal; an image calculation processor 432; a microscope body controller 468 for detecting focus and magnification information of a microscope body 402 of the operation microscope 401 and transmitting the detected information to the workstation 466; and a switch 469 for turning off the scale display displayed in the field of the operation microscope 401. Moreover, a monitor 470 is connected to the CCU 449 via the mixer 467.

Operation of the thirteenth embodiment constituted as described above will next be described. In the thirteenth embodiment the operation microscope 401 and rigid endoscope 434 are used together as shown in FIG. 54. Moreover, the rigid endoscope 434 is inserted into the operative portion P, and a tip end of the rigid endoscope 434 is brought to the operative portion P in a desired position.

In this case, the observation image of the operative portion P observed by the rigid endoscope 434 is guided to the eyepiece member 437 via the objective lens 441 and relay lens, formed on the image pickup device in the TV camera 447, and converted to an electric signal. This electric signal is transmitted to the CCU 449 via the camera cable 448, and converted to an image signal by the CCU 449. Moreover, an output signal from the CCU 449 is transmitted to the monitor 470 via the mixer 467, and the observation image of the rigid endoscope 434 photographed by the TV camera 447 is displayed in the monitor 470. In this case, the light emitted from the projection windows 443, 444 of the tip end slope 439 of the insertion member 435 of the rigid endoscope 434 is projected to a wall surface A of the operative portion P. Moreover, an operating person 458 who looks into the eyepiece lens 410 of the eyepiece lens tube 433 of the operation microscope 401 observes an image in accordance with an insertion position of the rigid endoscope 434 inserted in the operative portion P.

Moreover, when the operating person 458 wants to know the length of the rigid endoscope 434 in the field, and the length of the operation microscope 401 in the microscope field, the following operation is performed. First, when the laser diode 454 is not on, the laser diode 454 is lit. In this case, when the laser diode lighting switch 457 is turned on, the output signal from the laser diode operation circuit 456 is inputted to the changeover means 462. Thereby, the changeover means 462 detects that the laser diode operation circuit 456 is in an operation state, and information outputted from the changeover means 462 is stored in the first memory 463.

In this case, image information M0 (observation image of the rigid endoscope 434 photographed by the TV camera 447) in which emission indexes 459$a$2, 459$b$2 are displayed in an observation image E1 of the rigid endoscope 434 as shown in FIG. 55 is transmitted to the CCU 449. Subsequently, the image information M0 of FIG. 55 is inputted to the first memory 463 via the changeover means 462. Thereby, screen information for one screen displayed in the monitor 470 is recorded as a unit in the first memory 463.

Subsequently, the laser diode 454 is turned off by the laser diode lighting switch 457. During the off operation of the laser diode lighting switch 457, the operation of the laser diode operation circuit 456 is stopped. Moreover, when the changeover means 462 detects that the laser diode operation circuit 456 is not operating, an output of the changeover means 462 is switched to a second memory 464 side.

Figure 56:
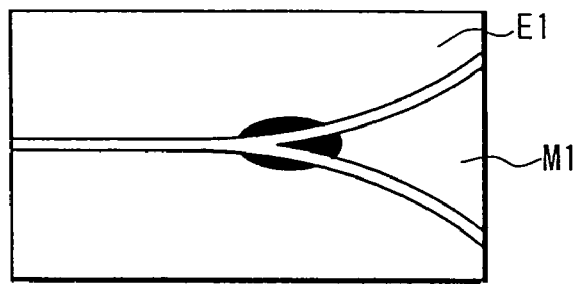
FIG. 56 is a plan view showing the image information in which no emission index is displayed in the operation image of the rigid endoscope of the thirteenth embodiment.
Figure 57:
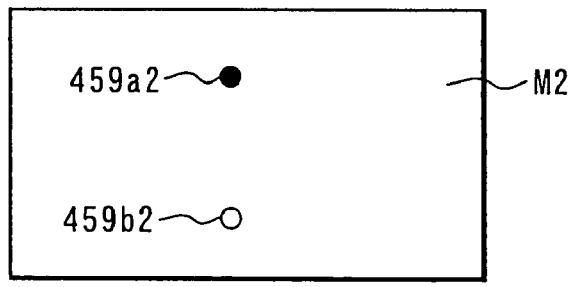
FIG. 57 is a plan view showing the image information only of the emission index in the operation microscope of the thirteenth embodiment.

In this case, image information M1 in which the emission indexes 459$a$2, 459$b$2 are not displayed in the observation image E1 of the rigid endoscope 434 as shown in FIG. 56 is transmitted to the CCU 449. Subsequently, the image information M1 of FIG. 56 is inputted to the second memory 464 via the changeover means 462. Thereby, the screen information for one screen displayed in the monitor 470 is recorded as the unit in the second memory 464, similar to the first memory 463.

Moreover, when the image information M1 for a first screen is stored in the second memory 464, the information is transmitted to the subtraction circuit 465. The subtraction circuit 465, having received the information, takes the image information M0 for the last screen stored in the first memory 463. Therefore, the image information M0 of the operative portion P during LD lighting and the image information M1 during LD non-lighting are inputted to the subtraction circuit 465.

Subsequently, the subtraction circuit 465 performs subtraction processing of the image information M1 and M0. Therefore, image information M2 only of the emission indexes 459$a$2, 459$b$2 can be obtained because of a difference between lighting and non-lighting of the LD 454 on the output side of the subtraction circuit 465. The image information M2 is transmitted to the workstation 466 from the subtraction circuit 465.

Furthermore, field size data of the rigid endoscope 434 by a lighting position of the LD 454 is recorded beforehand in the workstation 466. Subsequently, when the image information M2 from the subtraction circuit 465 is inputted to the workstation 466, a field size of the rigid endoscope 434 is calculated in accordance with the emission indexes 459$a$2, 459$b$2 of the image information M2.

Figure 58:
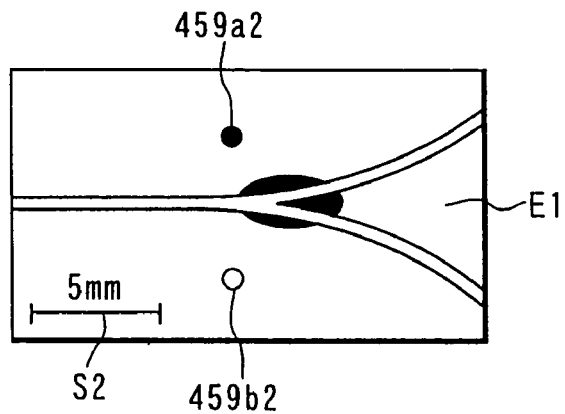
FIG. 58 is a plan view showing the image in which the emission index and a scale character is superposed onto each other in the same screen of the observation image of the rigid endoscope in the operation microscope of the thirteenth embodiment.

Subsequently, a character indicating the shorter scale S2 is prepared from the calculated field diameter in the workstation 466. The character of the scale S2 is transmitted to the image calculation processor 432 and mixer 467. In this case, the mixer 467 synthesizes the output signals from the CCU 449 and workstation 466. Then, the synthesized image signal is transmitted to the monitor 470 from the mixer 467. Thereby, as shown in FIG. 58, an image in which the emission indexes 459$a$2, 459$b$2 and the character of the scale S2 are superposed/displayed in the same screen is displayed in the observation image E1 of the rigid endoscope 434.

Moreover, the microscope body controller 468 transmits the magnification and focus information of the microscope body 402 of the operation microscope 401 to the workstation 466. Furthermore, the workstation 466 calculates the field diameter of the observation image K1 of the operation microscope 401 based on the output signal of the microscope body controller 468.

Furthermore, the workstation 466 generates the scale S1 having an appropriate length and the character indicating the length with respect to the calculated field diameter of the observation image K1 of the operation microscope 401. Here, the generated scale S1 and character are transmitted as the image signal to the image calculation processor 432. As shown in FIG. 59, images (microscope observation image, and in-field display image) are obtained in which the scales S1, S2 having appropriate lengths, and characters indicating the lengths with respect to the field diameter of the microscope field are displayed in the observation image K1 of the operation microscope 401 displayed in the field of the eyepiece lens 410 of an eyepiece lens tube 433 of the operation microscope 401, and the observation image E1 of the rigid endoscope 434 displayed in the sub-screen N inserted into the microscope observation image K1. Therefore, the operating person can recognize the field size of the observation image K1 of the operation microscope 401 and the field size of the observation image E1 of the rigid endoscope 434 by observing the microscope observation image and in-field display image of FIG. 59. The operating person can move the rigid endoscope 434 or obtain size information of the operative portion P based on the recognized sizes.

Figure 60:
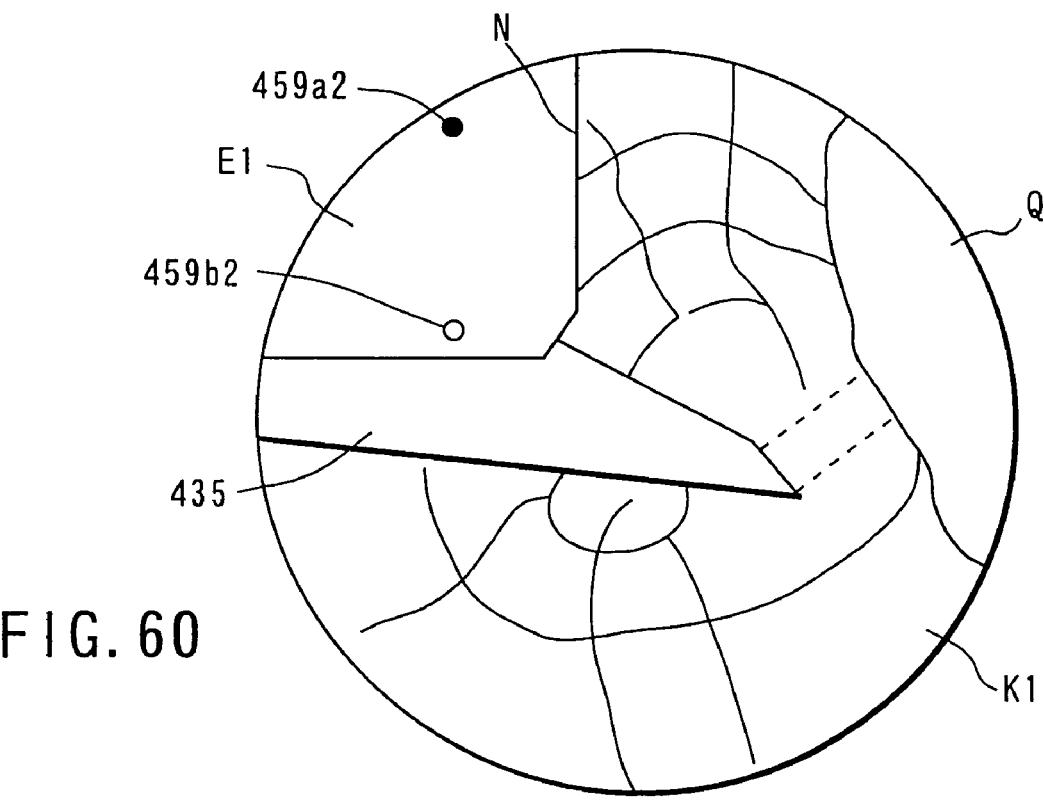
FIG. 60 is a plan view showing a case in which the display of the scale in the operation microscope field of the thirteenth embodiment and the character indicating the length of the scale is deleted.

Moreover, when the switch 469 is pressed, the workstation 466 does not transmit the image observation image of the scales S1, S2 and characters indicating the scale lengths to the image calculation processor 432. As shown in FIG. 60, the usual observation image K1 of the operation microscope 401, and the in-field display image of the observation image E1 of the rigid endoscope 434 displayed in the sub-screen N inserted into the microscope observation image K1 are displayed.

Therefore, the following effect is achieved in the aforementioned constitution. That is, in the thirteenth embodiment, there is provided the scale generation apparatus 461 for generating the scales S1, S2 having appropriate lengths, and characters indicating the lengths with respect to the field diameter of the microscope field in the observation image K1 of the operation microscope 401 displayed in the field of the eyepiece lens 410 of the eyepiece lens tube 433 of the operation microscope 401, and the observation image E1 of the rigid endoscope 434 displayed in the sub-screen N inserted into the microscope observation image K1 as shown in FIG. 59. Therefore, correlation between the field diameter of the observation image K1 of the operation microscope 401 and the field diameter of the in-field display by the observation image E1 of the rigid endoscope 434 can be obtained.

Consequently, the operating person 458 gazes at the field of the observation image K1 of the operation microscope 401 displayed in the field of the eyepiece lens 410 of the eyepiece lens tube 433 of the operation microscope 401, and thereafter observes the observation image E1 of the rigid endoscope 434 as the in-field display image displayed in the sub-screen N. Even in this case, the operating person can easily grasp the size of the operative portion P in the display image, select the appropriate rigid endoscope 434 in accordance with the field, and objectively grasp a movement amount of the rigid endoscope 434 during observation.

Moreover, the size of the affected part of the operative portion P can be accurately known by visually confirming the character of the scale S2 in the observation image E1 of the rigid endoscope 434, and the character of the scale S1 in the observation image K1 of the operation microscope 401. Therefore, information such as the patient's condition and worsening degree can be brought to the attention of the operating person 458. Therefore, the operating time is further shortened, and burdens on the operating person and patient are effectively reduced.

Figure 61:
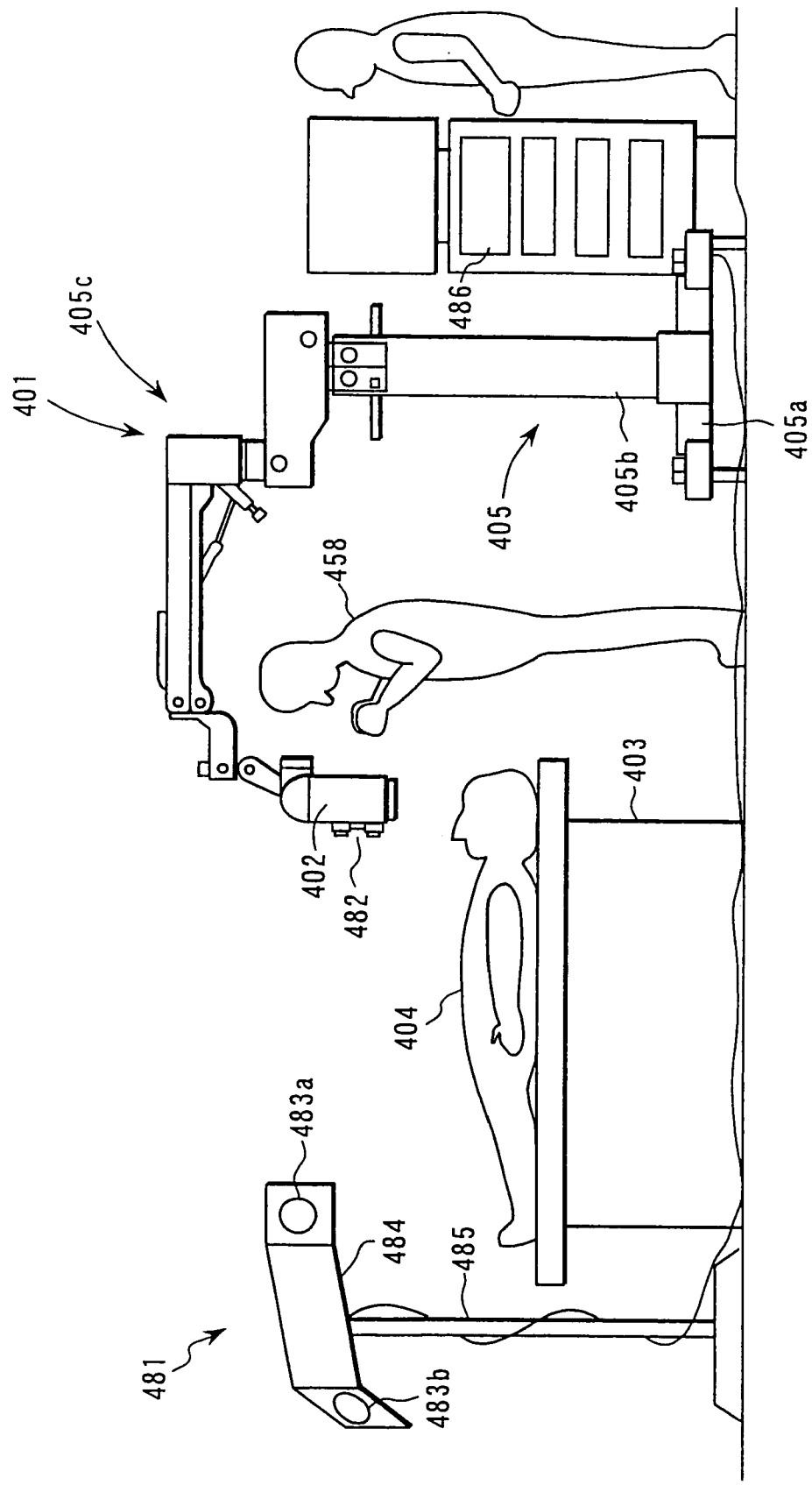
FIG. 61 is a schematic constitution diagram showing the entire system of the operation microscope according to a fourteenth embodiment of the present invention.

Furthermore, FIG. 61 to FIG. 66 show a fourteenth embodiment of the present invention. In the system of the operation microscope 401 of the fourteenth embodiment, as shown in FIG. 61, a digitizer (observation position detection means) 481 for detecting the position of the microscope body 402 is disposed. Moreover, an emission index 482 by which the digitizer 481 detects a three-dimensional coordinate of the microscope body 402 is attached to the microscope body 402. Here, as shown in FIG. 61, the digitizer 481 is disposed on a base side of a bed 403 (e.g., feet side of a patient 404 on the bed 403) in the operating theater.

This digitizer 481 is constituted of two CCD cameras 483a, 483b as receiving members, a camera support member 484 for fixing positions of the respective CCD cameras 483a, 483b, and a stand 485. Moreover, the respective CCD cameras 483a, 483b are connected to a workstation (character preparation means) 486 via a measurement apparatus (not shown) and A/D converter. Preoperative tomographic image data from an image diagnosis apparatus (not shown) such as CT or MRI, and data (preoperative diagnosis image) three-dimensionally re-constructed by processing the tomographic image data are stored in a storage section incorporated in the workstation 486.

Figure 62:
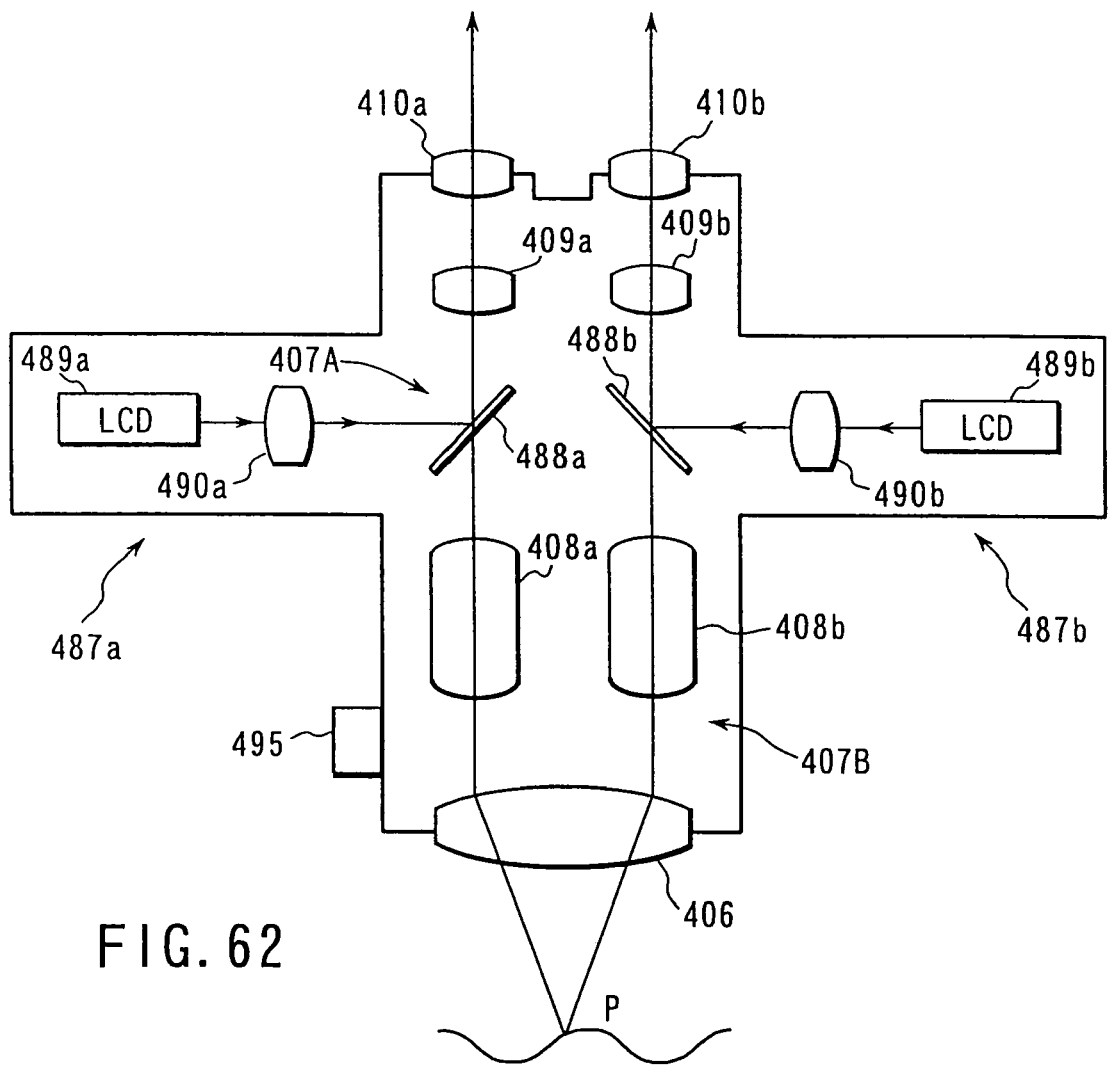
FIG. 62 is a schematic constitution diagram of the optical system in the microscope body in the operation microscope of the fourteenth embodiment.

Moreover, as shown in FIG. 62, the fourteenth embodiment incoporates an in-field image insertion apparatuses 487a, 487b for inserting the image into the field of the operation microscope 401. The apparatuses 487a and 487b are identical in structure. In the in-field image insertion apparatus 487a, as shown in FIG. 62, a half mirror 488a is disposed between an image forming lens 409a and a variable power optical system 408a in the microscope body 402a. Furthermore, an LCD (character display means) 489a for displaying the image signal, and a lens 490a for leading the image to the half mirror 488a are disposed. Additionally, left and right opposite-eye optical observation systems 407A and 407B are similarly constituted (see FIG. 62).

Figure 63:
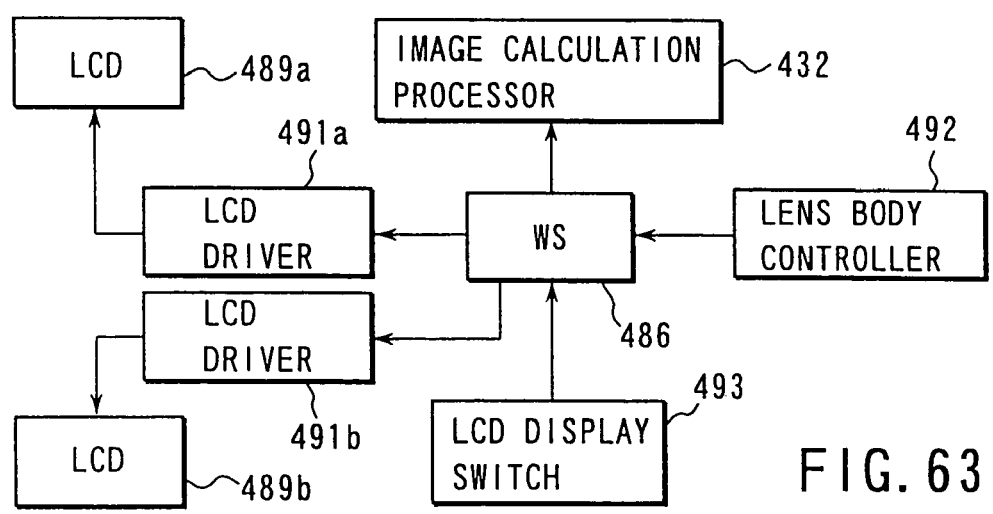
FIG. 63 is a schematic constitution diagram showing a connection state of a workstation in the operation microscope of the fourteenth embodiment.

Furthermore, as shown in FIG. 63, the LCDs 489a, 498b are connected to the workstation 486 via an LCD drivers 491a, 491b for driving the LCDs 489a, 489b. The workstation 486 is connected to a microscope body controller (observation position detection means) 492 for detecting magnification and focus information of the microscope body 402, a foot switch (not shown) to which an LCD display switch 493 for turning ON/OFF image signal display in the LCDs 489a, 489b are attached, and the image calculation processor 432. Here, the microscope body controller 492 is disposed in the microscope body 402. Additionally, as shown in FIG. 62, a focus knob 495 is disposed in the microscope body 402.

Operation of the fourteenth embodiment constituted as described above will next be described. In the fourteenth embodiment, when the operation microscope 401 is used, the operating person 458 moves the microscope body 402, adjusts the focus and magnification of the left and right opposite-eye optical observation systems 407A, 407B, and observes the operative portion P.

Moreover, when an operating person 458 turns on a foot switch 427 during observation by the operation microscope 401, in-field display of the operation microscope 401 starts. At the start of the in-field display, an image selector (not shown) selects a preoperative image corresponding to a focus position of the microscope body 402 from the workstation 486. Thereby, the in-field image insertion apparatus 487 displays a preoperative image R1 corresponding to the focus position of the microscope body 402 of the operation microscope 401 in the sub-screen N in the observation image K1 of the operation microscope 401 displayed in the field of the eyepiece lens 410 of the operation microscope 401 as shown in FIG. 64.

Furthermore, the magnification and focus information of the left and right opposite-eye optical observation systems 407A, 407B detected by the microscope body controller 492, and position information of the microscope body 402 detected by the digitizer 481 are transmitted to the workstation 486 during observation by the operation microscope 401. A substantially conical character 496 is generated based on the information as shown in FIG. 65. Additionally, upper and lower ends of the character 496 indicate a focus depth range.

In the character 496, a focus position display ring 497 indicating the focus position of the left and right opposite-eye optical observation systems 407A, 407B is displayed in the entire outer peripheral surface of a cone. Furthermore, graduations 498 are displayed at constant intervals on front and back parts of the focus position display ring 497.

Subsequently, when the operating person 458 turns on the LCD display switch 493 of the foot switch to start the display of the LCDs 489a, 489b, the workstation 486 sends operation signals for starting the operation of the LCD drivers 491a, 491b and the image signal of the generated character 496 to the LCDs driver 491a, 491b.

In this case, the LCDs driver 491a, 491b transmits the operation signal to the LCDs 489a, 489b, starts the operation of the LCDs 489a, 489b, and transmits the image signals of the character 496 to the LCDs 489a, 489b. Thereby, the character 496 is displayed in the LCDs 489a, 489b.

Furthermore, the character 496 displayed in the LCDs 489a, 489b is reflected by the half mirrors 488a, 488b via the lenses 490a, 490b, and transmitted to the eyepiece lenses 410a, 410b side through the image forming lenses 409a, 409b. Thereby, as shown in FIG. 66, the character 496 is superposed onto the observation image K1 of the operation microscope 401 displayed in the field of the eyepiece lenses 410a, 410b, and reaches the eyes of the operating person 458. Additionally, in FIG. 66, part X of the character 496 contacts an operative surface, and the focus position display ring 497 is disposed above the operative surface.

In this case, the operating person 458 confirms the position of the character 496, and moves the position of the focus position display ring 497 downward. Moreover, the operating person 458 confirms a deviation of the preoperative image by a navigation technique displayed in the in-field display screen from the operative surface. Additionally, even when the operative surface is above the focus position display ring 497, the same applies.

Moreover, when the operating person 458 changes an observation field, and adjusts the magnification and focus, the microscope body controller 492 transmits the changed position, magnification and focus information to the workstation 486. The conical character 496 including the focus position display ring 497 of the left and right opposite-eye optical observation systems 407A, 407B and graduations 498 on the front and back parts of the ring is newly generated based on the new information. Thereafter, the character 496 is superposed and displayed in the observation image K1 of the operation microscope 401 displayed in the field of the eyepiece lenses 410a, 410b as described above.

Moreover, when the display of the character 496 is unnecessary, the LCD display switch 493 is pressed. Then, the workstation 486 emits the operation signal for ending the operation of the LCD drivers 491a, 491b, and the LCD drivers 491a, 491b having received the signal ends the display operation of the LCDs 489a, 489b. Thereby, the operation of the LCD drivers 491a, 491b ends.

In this case, the following effect is achieved in the aforementioned constitution. That is, in the fourteenth embodiment, the operating person 458 checks a deviation size of the focus position display ring 497 of the character 496 displayed in the observation image K1 of the operation microscope 401 displayed in the field of the eyepiece lenses 410a, 410b from the graduations 498 by which the character 496 seems to overlap the operative surface. Thereby, a deviation amount between the focus position of the left and right opposite-eyes optical observation systems 407A, 407B and the operative surface can be confirmed. Therefore, focus can easily be adjusted to an object surface without depending on an eye adjustment function of the operating person 458, and the focus position can effectively be adjusted.

The process of moving the microscope body 402, changing the magnification of the left and right opposite-eye optical observation systems 407A, 407B and adjusting the focus many times is troublesome for the operating person 458. Therefore, when the operative surface is in the focus depth of the left and right opposite-eye optical observation systems 407A, 407B, the operation is supposedly continued. In this case, since the preoperative image of the navigation technique deviates from the operative surface, the deviation can effectively be confirmed by visually observing the character 496.

The character 496 may be composed of two images that have parallax to each other. If so, the LDC monitors 489a and 489b will cooperate to display a three-dimensional image.

FIG. 67A to FIG. 72 show a fifteenth embodiment of the present invention. The fifteenth embodiment is constituted by changing the system constitution of the operation microscope 401 of the fourteenth embodiment (see FIG. 61 to FIG. 66) as follows.

Figure 67B:
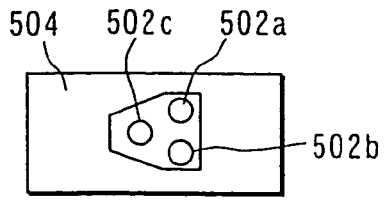
FIG. 67B is a plan view showing three emission indexes attached to the rigid endoscope.
Figure 67A:
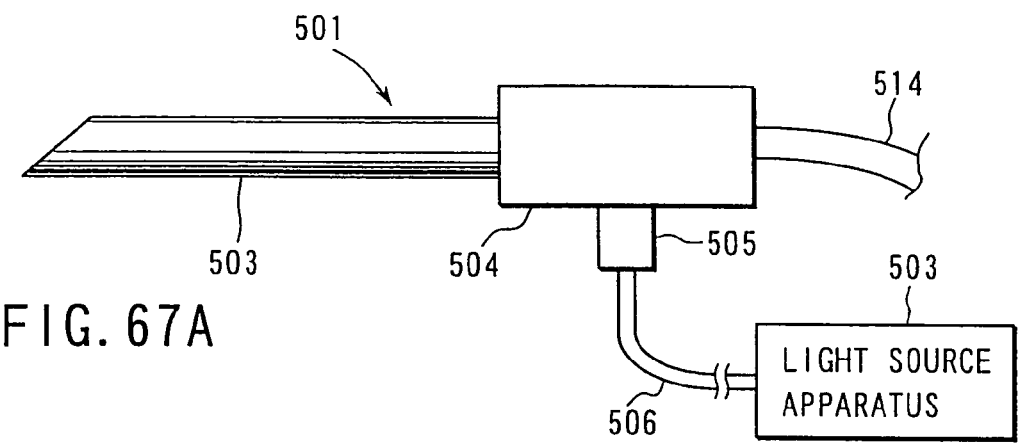
FIG. 67A is a schematic constitution diagram showing a main part of the rigid endoscope used together with the operation microscope according to a fifteenth embodiment of the present invention.

That is, in the system of the operation microscope 401 according to the fifteenth embodiment, a rigid endoscope 501 shown in FIG. 67A is used together. Additionally, a peripheral constitution of the operation microscope 401 is substantially similar to that of FIG. 61. Additionally, in the constitution of the digitizer 481, the emission index 482 attached to the microscope body 402 of the operation microscope 401, and three emission indexes 502a to 502c attached to the rigid endoscope 501 can be distinguished and detected as shown in FIG. 67B.

Moreover, the rigid endoscope 501 includes a thin longitudinal straight tubular insertion member 503 to be inserted into a body cavity as shown in FIG. 67A. A grip member 504 and light guide base 505 are disposed on a base end of the insertion member 503.

Furthermore, as shown in FIG. 67B, three emission indexes 502a, 502b, 502c are disposed on the upper surface of the grip member 504 of the rigid endoscope 501. Furthermore, one end of a light guide 506 is connected to the light guide base member 505. The other end of the light guide 506 is connected to a light source apparatus 507.

Figure 68:
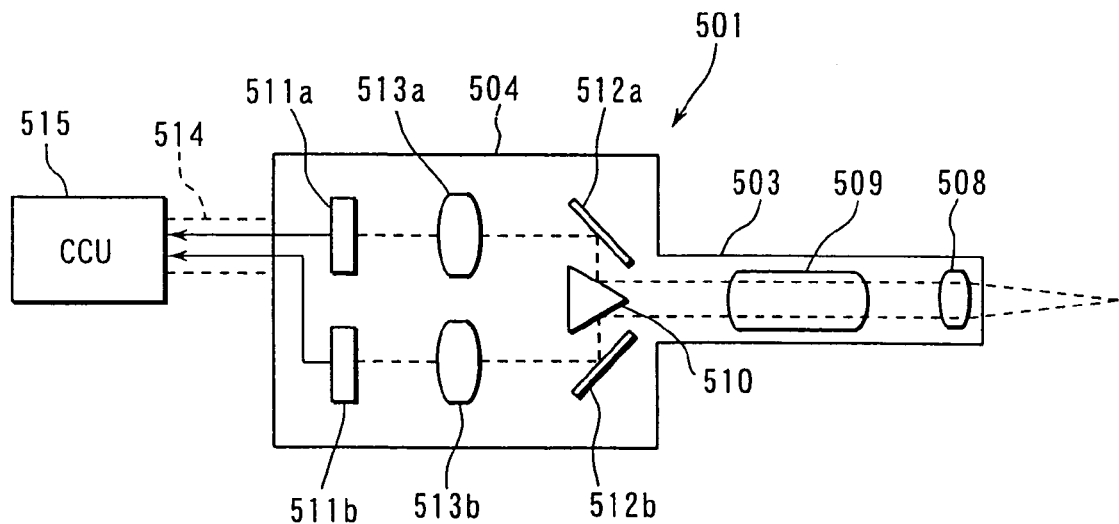
FIG. 68 is a schematic constitution diagram showing the inside of the rigid endoscope in the operation microscope of the fifteenth embodiment.

Moreover, as shown in FIG. 68, an objective lens 508 is disposed in the tip end of the insertion member 503 inside the rigid endoscope 501. Furthermore, a relay lens 509 is disposed inside the insertion member 503.

Furthermore, in the grip member 504, a prism 510 is disposed opposite to the relay lens 509 on a connection member side with the insertion member 503, and a pair of left and right CCDs 511a, 511b are disposed in the other end of the grip member. Additionally, a reflective mirror 512a and image forming lens 513a are successively disposed between the prism 510 and the left CCD 511a, and a reflective mirror 512b and image forming lens 513b are also successively disposed between the prism 510 and the right CCD 511b. Here, the left and right reflective mirrors 512a, 512b are disposed on opposite sides of the prism 510.

Additionally, the observation image incident from the objective lens 508 on the tip end of the insertion member 503 is transmitted toward the grip member 504 through the relay lens 509. The transmitted observation image is reflected and branched to two light paths by the prism 510. One light reflected by the prism 510 is formed into the image by the CCD 511a via the image forming lens 513a from the reflective mirror 512a, and the other light reflected by the prism 510 is formed into the image by the CCD 51b via the image forming lens 513b from the reflective mirror 512b. Moreover, the observation images observed via the rigid endoscope 501 are converted and outputted as the electric signals via these CCDs 511a, 511b.

Moreover, one end of a cable 514 is connected to the grip member 504. The other end of the cable 514 is connected to a camera control unit (CCU) 515. Output signals from the CCDs 511a, 511b are transmitted to the CCU 515 via the cable 514.

Figure 69:
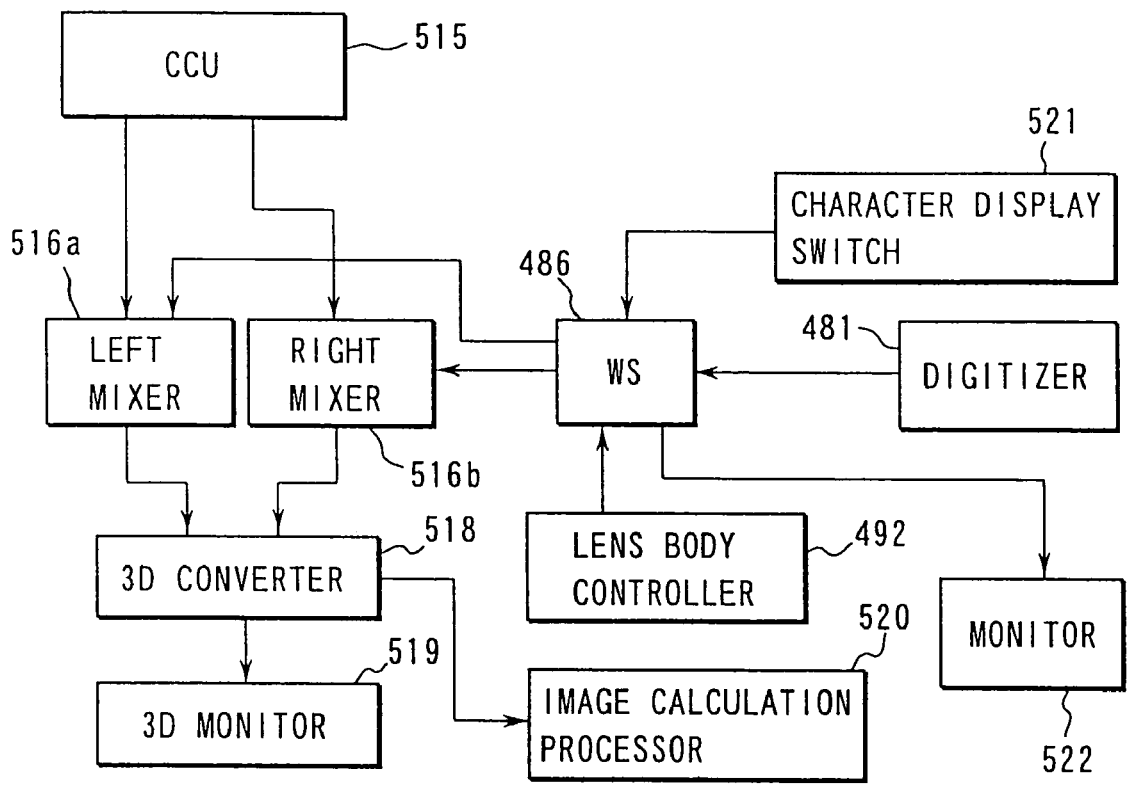
FIG. 69 is a schematic constitution diagram showing peripherals of the rigid endoscope in the operation microscope of the fifteenth embodiment.

Furthermore, as shown in FIG. 69, one input end of a left mixer 516a for superposing the image signal, and one input end of a right mixer 516b are connected to the CCU 515. Each of the left and right mixers 516a and 516b is provided with two input ends and one output end. Additionally, the workstation 486 is connected to the other input end of the left mixer 516a and the other input end of the right mixer 516b.

Moreover, the output ends of the left and right mixers 516a and 516b are connected to input ends of a 3D converter 518 for calculating/processing a flat image signal and preparing a three-dimensional image. Output ends of the 3D converter 518 are connected to a 3D monitor 519 for displaying the three-dimensional image and an image calculation processor 520.

Furthermore, the digitizer 481 for specifying the position of the rigid endoscope 501 is connected to the workstation 486. Additionally, a character display switch 521, the microscope body controller 492 for detecting the magnification and focus information of the microscope body 402 of the operation microscope 401, and a monitor 522 are connected to the workstation 486.

Figure 70:
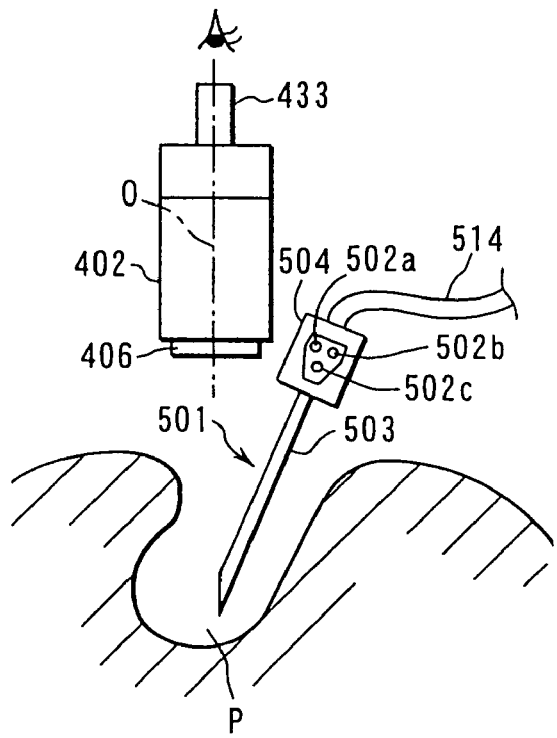
FIG. 70 is a schematic constitution diagram of the main part showing a state in which the insertion member tip end of the rigid endoscope used together with the operation microscope of the fifteenth embodiment is inserted into the pore of the portion subjected to the operation.

Operation of the fifteenth embodiment constituted as described above will next be described. In the fifteenth embodiment, when the operation microscope 401 and rigid endoscope 501 are used together as shown in FIG. 70, the operating person 458 moves the microscope body 402 of the operation microscope 401 to a desired position, sets the microscope body in the observation position of the operative portion P, and fixes the rigid endoscope 501 in a position desired by the operating person.

In this case, the observation image by the rigid endoscope 501 is passed through the relay lens 509 from the tip-end objective lens 508, and divided into two light paths by the prism 510. Moreover, some of the light reflected by the prism 510 is formed into the image by the CCD 511a via the image forming lens 513a from the reflective mirror 512a, and some of the light reflected by the prism 510 is formed into the image by the CCD 511b via the image forming lens 513b from the reflective mirror 512b. Furthermore, the observation image formed on the CCDs 511a, 511b is converted into an electric signal.

Moreover, the electric signals outputted from the CCDs 511a, 511b are inputted to the CCU 515, and the image signals outputted from two CCDs 511a, 511b are separated from each other. Furthermore, the two image signals are separately inputted to the left and right mixers 516a and 516b, three-dimensionally converted by the 3D converter 518 to form stereoscopic endoscope observation images, and inputted to the image calculation processor 520 and 3D monitor 519, so that the endoscope image can be observed.

Figure 71:
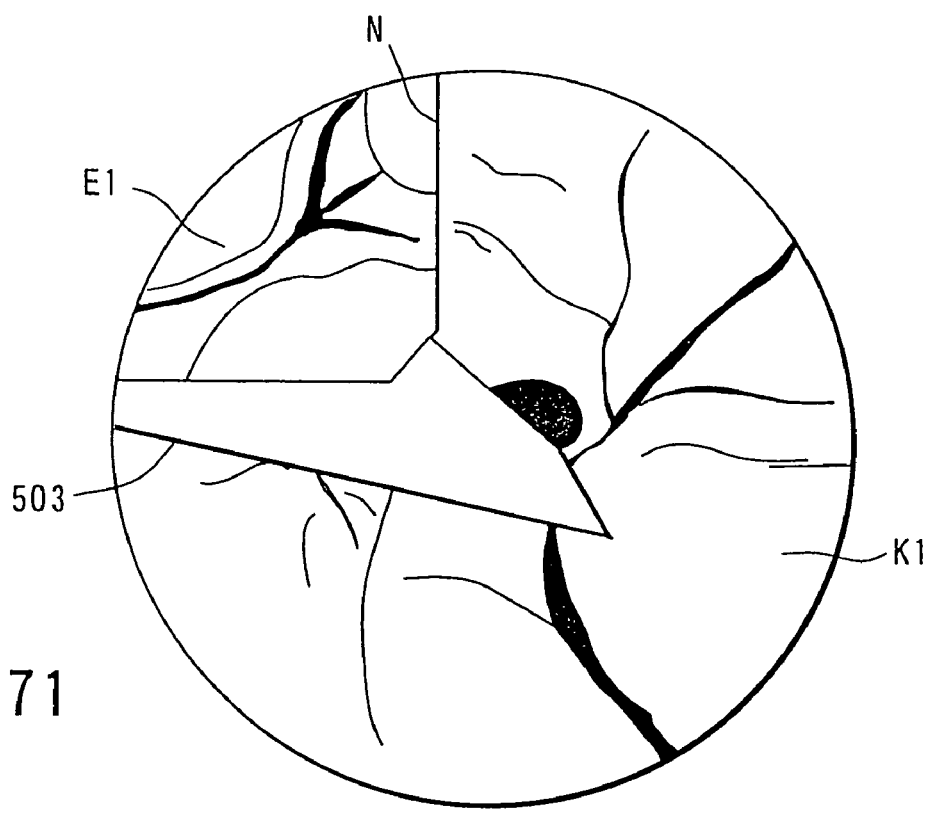
FIG. 71 is a plan view showing an image in which the observation image of the rigid endoscope is displayed in the sub-screen of the observation image of the operation microscope according to the fifteenth embodiment.

Furthermore, when the operating person presses an in-field display operation switch (not shown), disposed on the foot switch, for starting in-field display, the image selector selects the endoscope observation image inputted from the 3D converter 518 via the image calculation processor 520. As shown in FIG. 71, the sub-screen N is inserted into the microscope field (observation image K1 of the operation microscope 401), and the observation image E1 of the rigid endoscope 501 is displayed in the sub-screen N.

Furthermore, when the rigid endoscope 501 is used, the digitizer 481 detects the emission indexes 502a, 502b, 502c of the rigid endoscope 501, and a position detection signal is transmitted to the workstation 486. Here, the workstation 486 performs a calculation processing based on the position detection signal, and defines the position of the rigid endoscope 501.

Additionally, the magnification and focus information from the microscope body controller 492, and the position information of the microscope body 402 from the digitizer 481 are transmitted to the workstation 486. The workstation 486 calculates the observation position of the microscope 401 based on the information. Furthermore, the workstation 486 selects the preoperative image corresponding to the calculated observation position of the microscope 401, and the monitor 522 displays the preoperative image.

Moreover, when the operating person 458 presses the character display switch 521, the workstation 486 generates the character 496 indicating the focus of the left and right optical observation systems 407A, 407B of the microscope 401 and the length scale of the microscope 401 before and after focus with respect to the direction of the observation light axis O based on the calculated observation position of the microscope 401.

Furthermore, in the workstation 486, arithmetic operation is performed so that the focus position of the left and right optical observation systems 407A, 407B of the microscope 401 can be displayed in the observation field of the rigid endoscope 501. The image signal provided with horizontal parallax is constructed in order to display the character 496 in the position.

Figure 72:
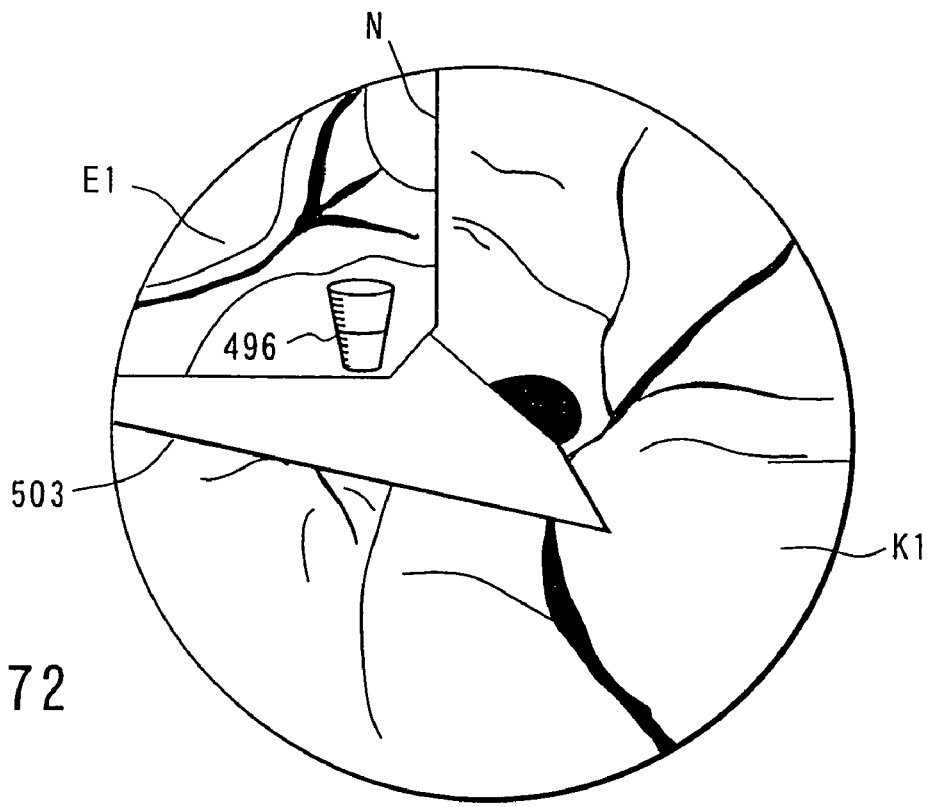
FIG. 72 is a plan view showing an image in which the character is superposed in the observation image of the rigid endoscope in the operation microscope of the fifteenth embodiment.

The image signal provided with the horizontal parallax is inputted to the left and right mixers 516a, 516b, and superimposed onto the observation image E1 of the rigid endoscope 501. Here, the superimposed left and right signals are further superimposed by the 3D converter 518, and the superimposed image signal is transmitted to the image calculation processor 520 and displayed in the 3D monitor 519 as shown in FIG. 72. Thereby, the character 496 indicating the focus position of the respective optical observation systems 407A, 407B of the microscope 401 is displayed in the field of the rigid endoscope 501 used together with the operation microscope 401.

Then, an effect similar to that of the fourteenth embodiment is obtained in the aforementioned constitution. Additionally, in the fifteenth embodiment, the character 496 indicating the focus position of the left and right optical observation systems 407A, 407B of the microscope 401 is displayed in the field of the rigid endoscope 501 used together with the operation microscope 401. Therefore, while the operating person 458 observes the observation image of the rigid endoscope 501, the person can effectively confirm the position of the image selected by the navigation technique in the observation image of the rigid endoscope 501.

Figure 73:
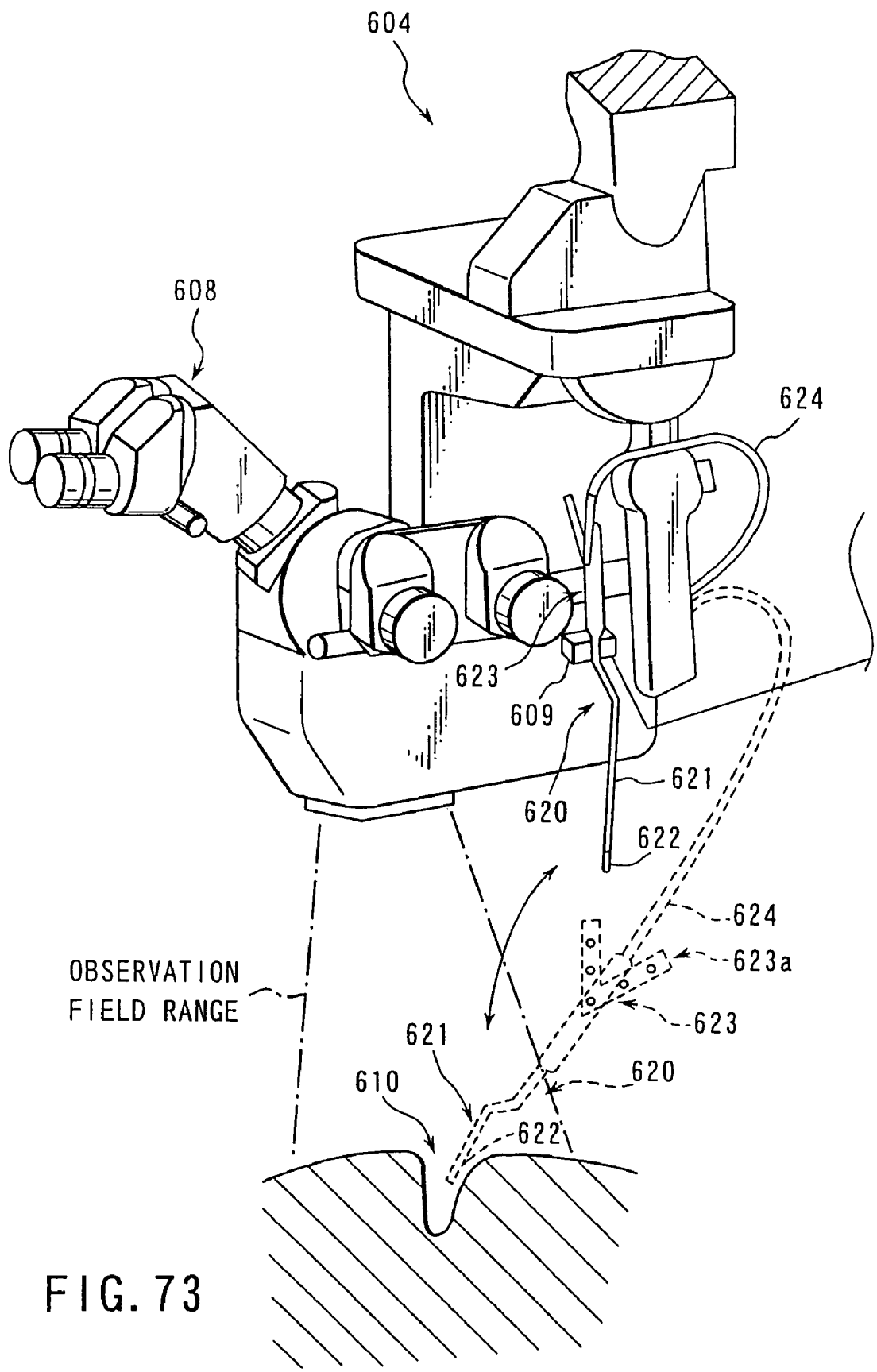
FIG. 73 is a perspective view of the microscope body in the operation microscope according to a sixteenth embodiment of the present invention.
Figure 74:
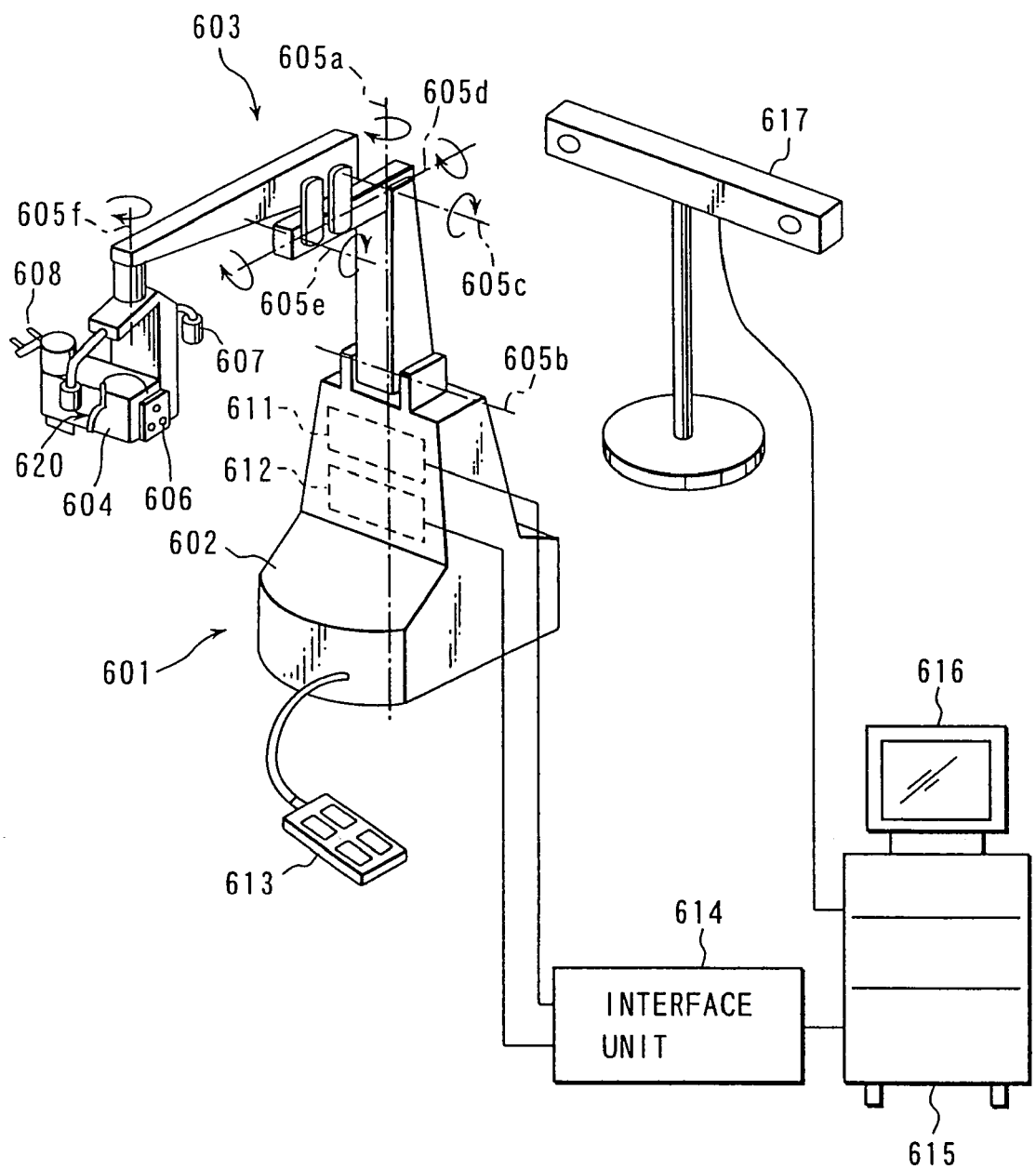
FIG. 74 is a perspective view of the entire operation microscope apparatus of the sixteenth embodiment.

Moreover, FIG. 73 to FIG. 78 show a sixteenth embodiment. FIG. 73 is a perspective view of a microscope body 604 of an operation microscope 601, and FIG. 74 is a constitution diagram of the entire system of the operation microscope apparatus. As shown in FIG. 74, the operation microscope apparatus includes the operation microscope 601 provided with a solid microscope.

The operation microscope 601 includes a stand 602, a balance arm 603 disposed on an upper part of the stand 602, and the microscope, body 604 supported by the balance arm 603. Here, the balance arm 603 includes a plurality of movable arms, and six rotation axes 605a to 605f. Furthermore, the respective rotation axes 605a to 605f are provided with electromagnetic locks (not shown) for switching a locked state in which the rotation positions of the respective rotation arms of the balance arm 603 are fixed and an unlocked state in which the locked rotation positions are released. Moreover, the microscope body 604 is supported in such a manner that the microscope body 604 can move in the spatial position centering on the respective six rotation axes 605a to 605f of the respective rotation arms of the balance arm 603 with the switching operation for locking/unlocking the electromagnetic locks.

Moreover, as shown in FIG. 74, the microscope body 604 includes a center arm 606 and a grip 607 for controlling the position of the microscope body 604. The grip 607 is provided with respective operation switches for focus adjustment, variable power operation, and arm operation.

Furthermore, the operation microscope 601 incorporates a microscope body controller 611 and arm controller 612. The respective switches of the grip 607 are connected to the microscope body controller 611 and arm controller 612. Additionally, the microscope body controller 611 and arm controller 612 are connected to a foot switch 613 including respective switches for focus adjustment and variable power operation similarly as the respective switches of the grip 607.

Moreover, the microscope body controller 611 and arm controller 612 are connected to a navigation apparatus 615 via an interface unit 614. A monitor 616 for navigation is disposed on the navigation apparatus 615.

The navigation apparatus 615 is connected to a digitizer 617. Furthermore, the image information from the digitizer 617 is inputted to the navigation apparatus 615, and the navigation apparatus 615 calculates a correlation with a reference index attached to a patient's head.

Figure 75:
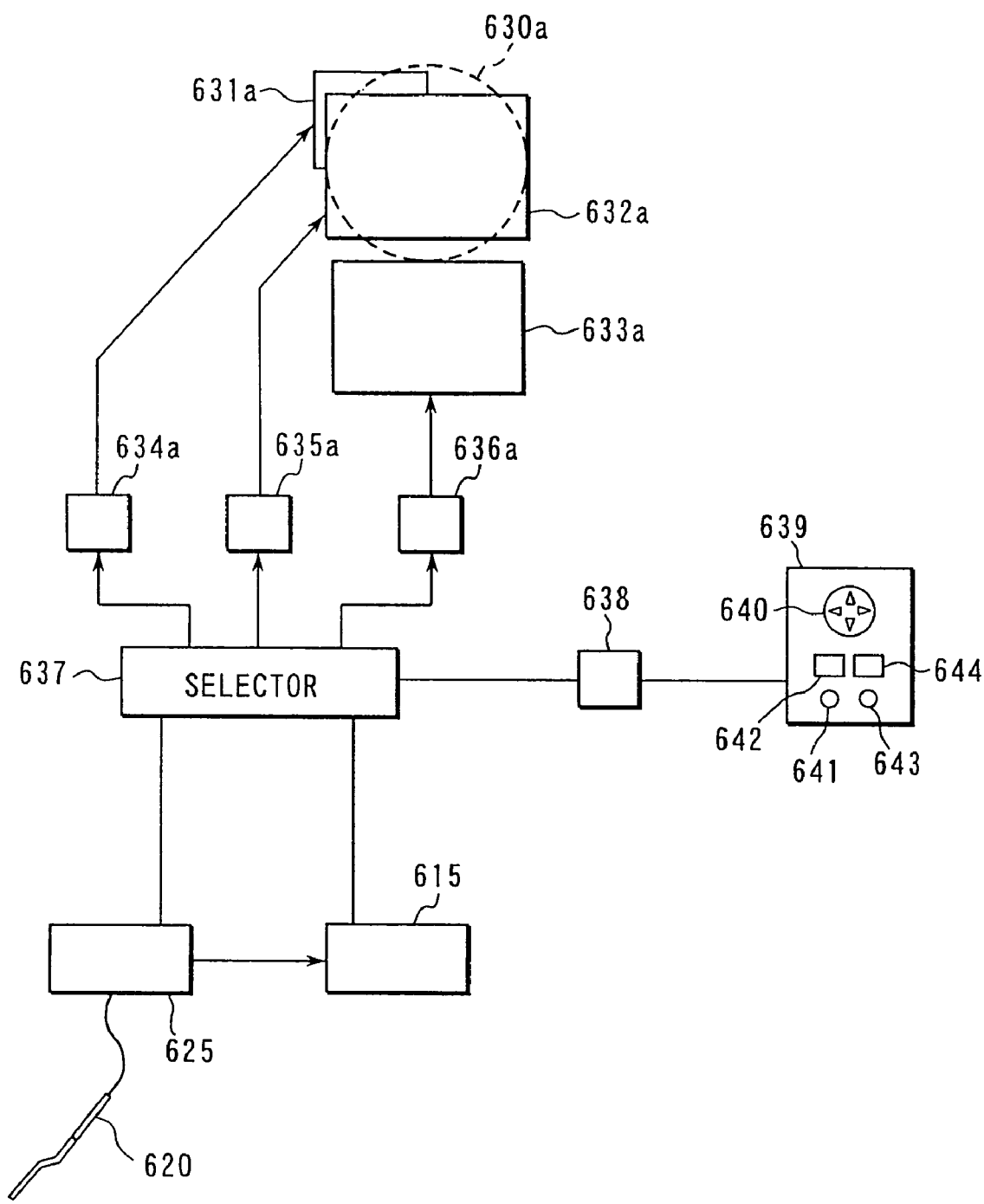
FIG. 75 is a control block diagram of the operation microscope apparatus of the sixteenth embodiment.

As shown in FIG. 73, an eyepiece lens tube 608 and a probe holder 609 are disposed in the microscope body 604. In the eyepiece lens tube 608, an in-field image displaying monitor and optical projection system for displaying the image in the microscope observation field are disposed (FIG. 75 shows a small screen display 631a of a left eye monitor). Moreover, a monitor and an optical overlay system for overlaying/displaying the image information in the microscope optical observation image are disposed. Furthermore, a microscope observation field monitor and a second image observing optical eyepiece system different from the microscope optical eyepiece system are disposed.

Furthermore, an ultrasonic probe 620 is disposed in the probe holder 609. The ultrasonic probe 620 is constituted of a straight pipe 621, an ultrasonic transmitting cap 622 disposed on a tip end of the straight pipe 621, and a handle member 623 disposed on a base end of the straight pipe 621. A sensor arm 623a is disposed in the handle member 623.

Moreover, the ultrasonic probe 620 is connected to an ultrasonic observation apparatus 625 shown in FIG. 75 via a flexible tube 624. Additionally, the operating person can hold the handle member 623 and insert a part of the ultrasonic transmitting cap 622 of the ultrasonic probe 620 into an operative portion 610.

FIG. 75 is a control block diagram of the operation microscope 601. In an operation input section 639, a four-direction switch 640, a display switch 641 and first display 642, and a selection switch 643 and second display 644 are disposed. The operation input section 639 is connected to a selector 637 via a display controller 638. The navigation apparatus 615 and ultrasonic observation apparatus 625 are connected to the selector 637.

Here, a left-side (left-eye) eyepiece section in the eyepiece lens tube 608 of the microscope body 604 is displayed/constituted. A right-side (right-eye) eyepiece section is also disposed, but description thereof is omitted.

Numeral 630a of FIG. 75 denotes a left-eye microscope observation field. The selector 637 is connected to a first display drive controller 634a for driving the small screen display 631a as a left-eye field image display, a second display drive controller 635a for driving an overlay display 632a for an image superimposing display and a third display drive controller 636a for driving a large screen display 633a for another image observation.

Figure 76:
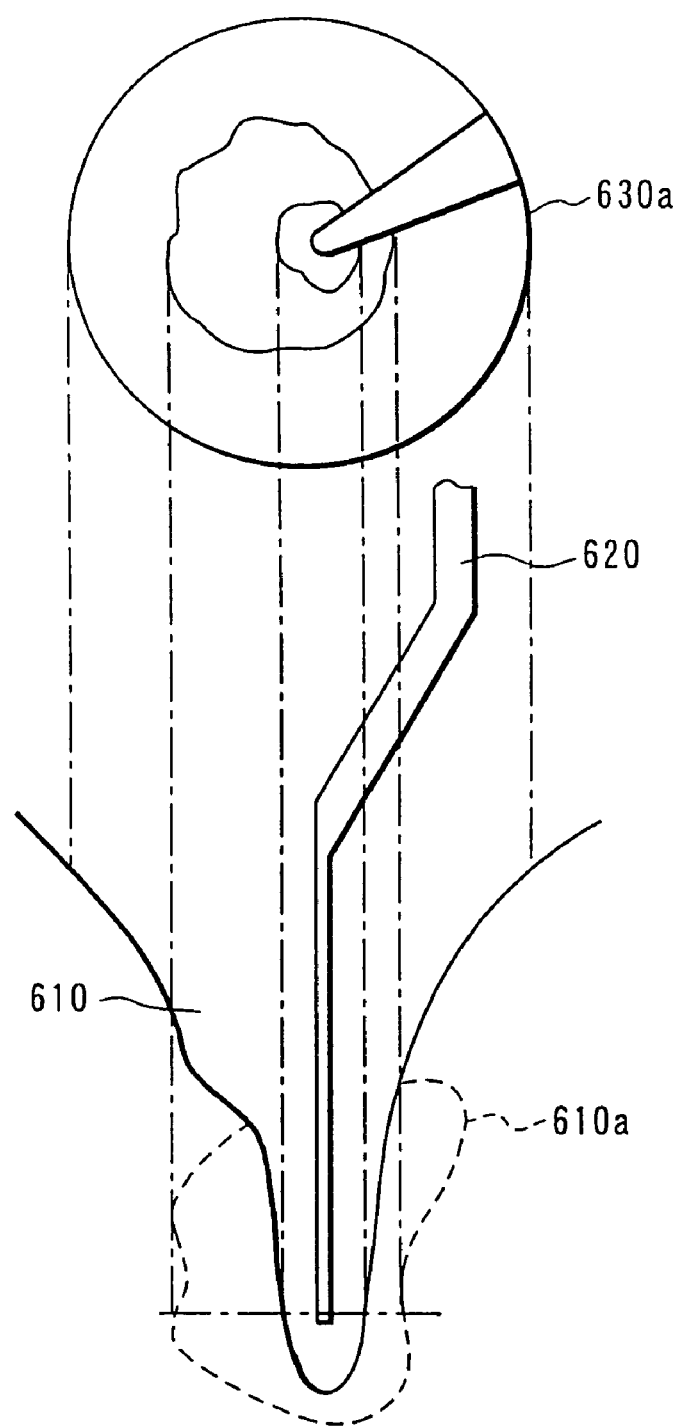
FIG. 76 is an explanatory view showing an ultrasonic observation state in the operation microscope apparatus of the sixteenth embodiment.

Operation of the sixteenth embodiment constituted as described above will next be described. FIG. 76 shows a normal ultrasonic observation state of the ultrasonic probe 620. During ultrasonic observation, the ultrasonic probe 620 is inserted into the operative portion 610, and an ultrasonic wave is radiated to all peripheries by 360 degrees via the tip-end ultrasonic transmitting cap 622. In this case, the ultrasonic wave reflected by a tumor portion 610a of the operative portion 610 is received by a sensor (not shown) of the ultrasonic probe 620 and transmitted to the ultrasonic observation apparatus 625.

The ultrasonic observation apparatus 625 analyzes the signal transmitted from the ultrasonic probe 620, processes the image, and displays a tumor tomographic image in the microscope observation field 630a. Additionally, in this case, a microscope image L of the ultrasonic probe 620 inserted into the microscope observation field 630a is also displayed.

Figure 77:
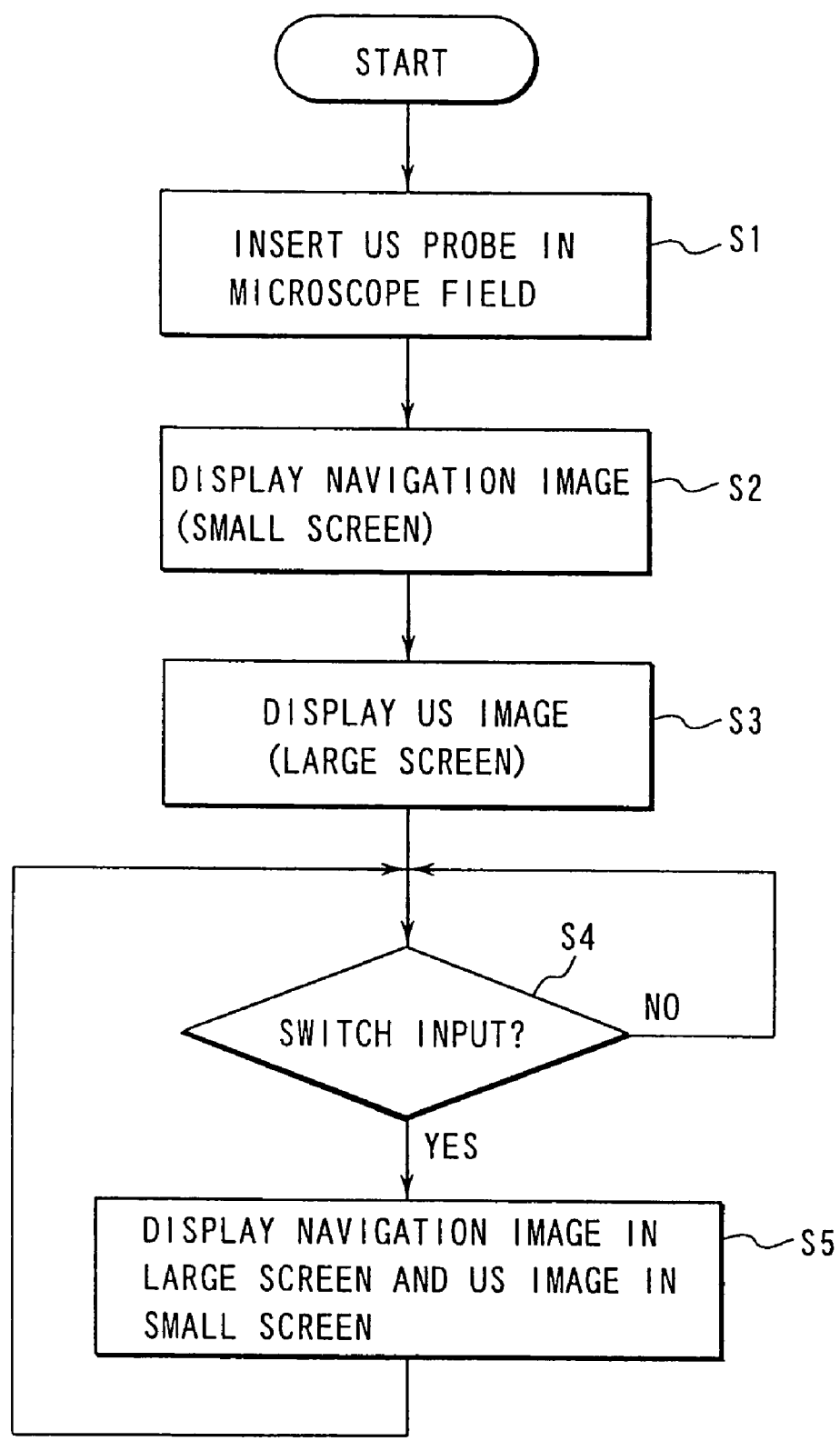
FIG. 77 is a flowchart showing an ultrasonic observation process in the operation microscope apparatus of the sixteenth embodiment.
Figure 78:
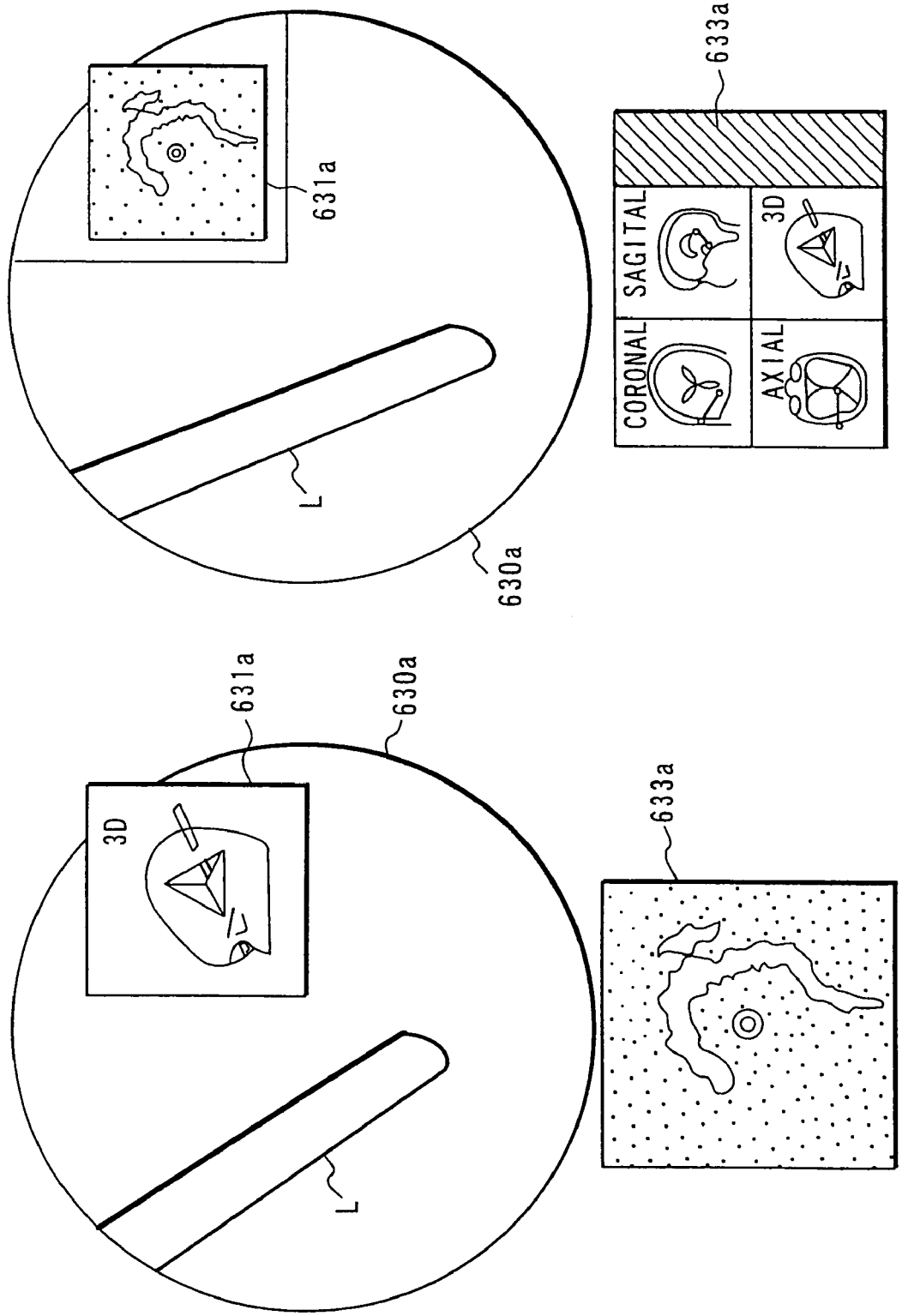
FIG. 78A is a diagram showing one example of the microscope observation field in which the microscope image of the ultrasonic probe in the operation microscope apparatus of the sixteenth embodiment is displayed.
FIG. 78B is a diagram showing another example of the microscope observation field in which the microscope image of the ultrasonic probe in the operation microscope apparatus of the sixteenth embodiment is displayed.

FIG. 77 is a flowchart of an automatic ultrasonic observation by the ultrasonic probe 620. As shown in FIG. 77, in step S1 the ultrasonic probe 620 is inserted into the microscope observation field 630a. Subsequently, in step S2 a navigation image is displayed in the small screen display 631a in the microscope observation field 630a. Thereafter, in the next step S3 the ultrasonic image is displayed in the large screen display 633a.

Therefore, as shown in FIG. 78A, the navigation image (three-dimensionally constructed image 3D) displayed in the small screen display 631a in the microscope observation field 630a, and the ultrasonic image displayed in the large screen display 633a are simultaneously displayed together with the microscope image L of the ultrasonic probe 620 displayed in the microscope observation field 630a.

Moreover, it is judged in the next step S4 whether or not there is an input of the selection switch 643. If YES, the process advances to the next step S5. In the step S5, screens to be displayed in the small screen display 631a in the microscope observation field 630a and in the large screen display 633a are changed in accordance with an input state of the selection switch 643. Here, a state in which the navigation image is displayed in the large screen display 633a and the ultrasonic image is displayed in the small screen display 631a is selected. Then, as shown in FIG. 78B, the ultrasonic image is displayed in the small screen display 631a in the microscope observation field 630a in which the microscope image L of the ultrasonic probe 620 is displayed. The navigation image (three-directional tomographic image, respective sagital, coronal and axial tomographic image information, and three-dimensionally constructed image 3D prepared based on the information) is displayed in the large screen display 633*a*.

Then, the following effect is achieved in the aforementioned constitution. That is, according to the sixteenth embodiment, during use of the ultrasonic probe 620, the ultrasonic image from the ultrasonic probe 620 is displayed in the microscope observation field 630*a* as it is. Additionally, an "outer shape display" in which position correlation in the microscope observation field 630*a* is obtained via the navigation apparatus 615 is superimposed onto an optical image. Then, the navigation image and ultrasonic image can simultaneously be observed in the microscope observation field 630*a*.

Furthermore, the screens to be displayed in the small screen display 631*a* in the microscope observation field 630*a* and in the large screen display 633*a*, and the overlay display can be changed in accordance with the input state of the selection switch 643. Therefore, the image of the ultrasonic probe 620, and the navigation image can be displayed in an optimum state whilst the operation progresses. Therefore, the operating person can obtain high-resolution tomographic image information in accordance with the operational situation, and can efficiently carry out the operation. Additionally, when the ultrasonic probe 620 is inserted, the image may be ON, or the image may be replaced.

FIG. 79 to FIG. 83 show a seventeenth embodiment. The seventeenth embodiment is constituted by changing the constitution of the operation microscope apparatus of the sixteenth embodiment (see FIG. 73 to FIG. 78) as follows. Additionally, the same constituting components as those of the sixteenth embodiment are denoted with the same reference numerals, and description thereof is omitted.

Figure 79:
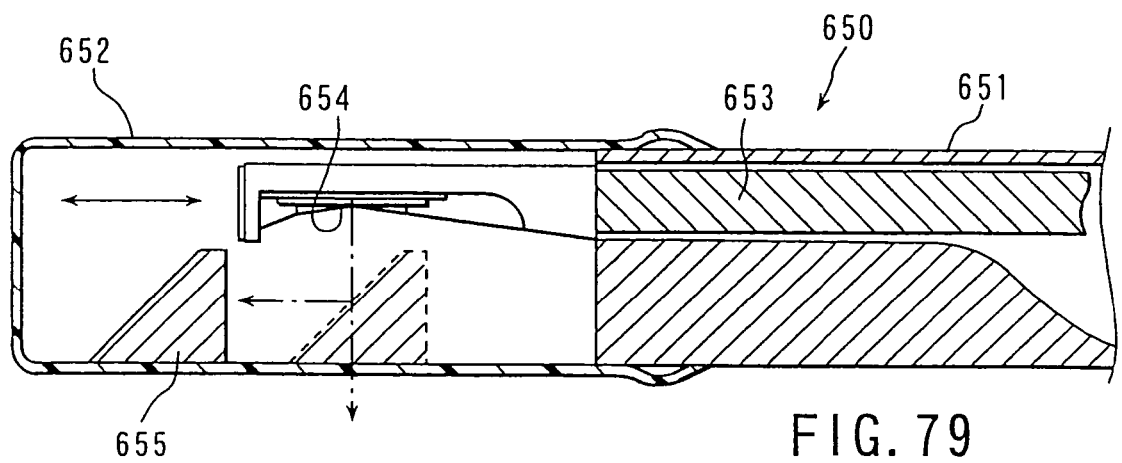
FIG. 79 is a longitudinal sectional view of the tip end of the ultrasonic probe according to a seventeenth embodiment of the present invention.

FIG. 79 is a longitudinal sectional view of a tip end of an ultrasonic probe 650 according to the seventeenth embodiment. In the ultrasonic probe 650 an ultrasonic transmitting cap 652 is disposed on a tip end of a probe pipe 651. A flexible shaft 653 is passed through the probe pipe 651, and the tip end of the shaft extends into the ultrasonic transmitting cap 652.

Moreover, in the ultrasonic transmitting cap 652, an ultrasonic piezoelectric transducer 654 is fixed to the flexible shaft 653. A mirror 655 for reflecting the ultrasonic wave is disposed opposite to the ultrasonic piezoelectric transducer 654 in such a manner that the mirror can advance or retreat. The mirror 655 can be moved forward or backward by operation of a hand operator.

Figure 80:
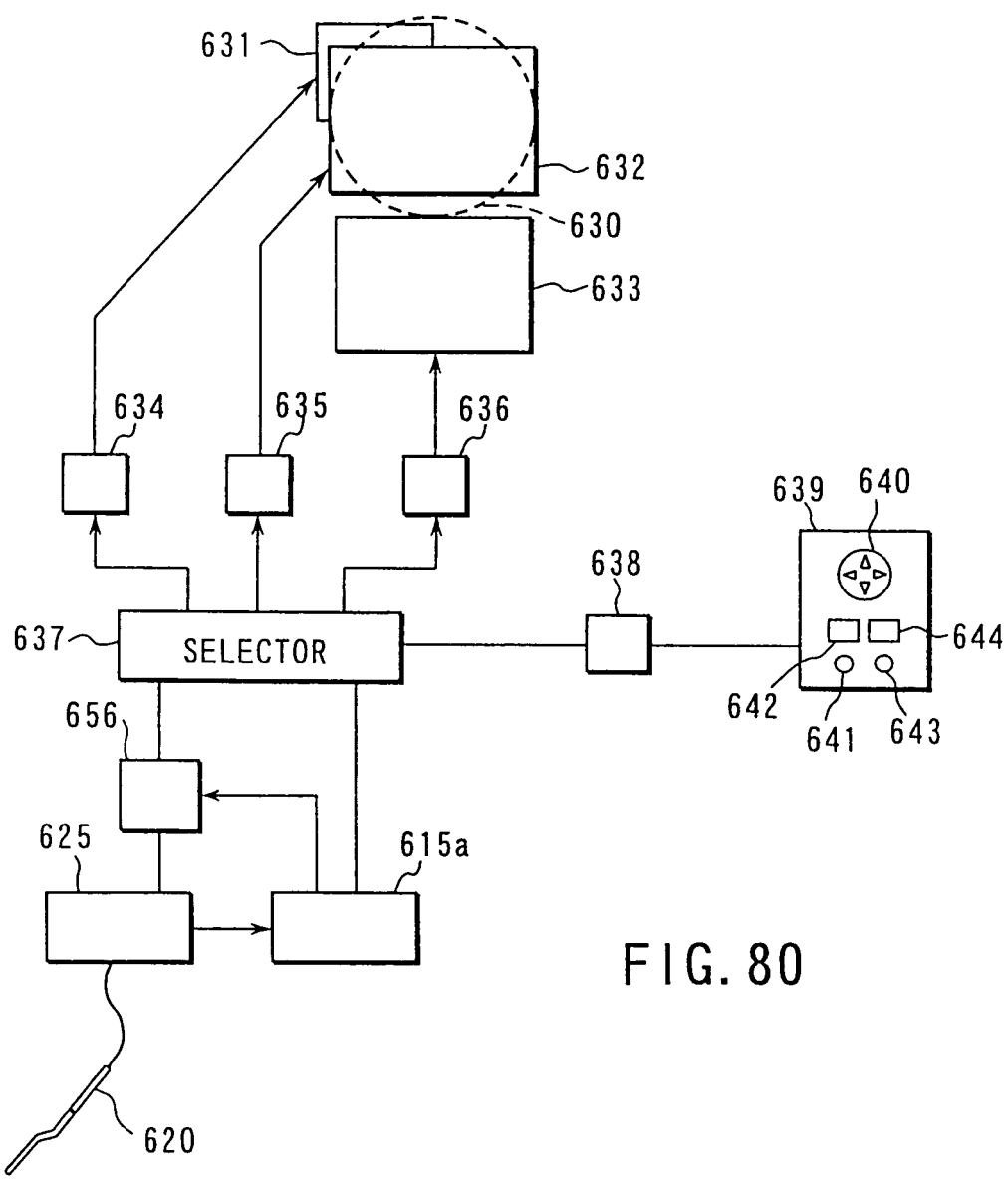
FIG. 80 is a control block diagram of the seventeenth embodiment.

FIG. 80 is a control block diagram of the operation microscope apparatus. An image display direction display 656 is disposed between the ultrasonic observation apparatus 625 and the selector 637. This display is connected to a navigation apparatus 615*a*. Other constitutions are the same as those of the sixteenth embodiment.

Operation of the seventeenth embodiment constituted as described above will next be described. First, when ultrasonic observation is performed by the ultrasonic probe 650, the mirror 655 is moved beforehand in the axial direction in accordance with an ultrasonic observation type. In FIG. 79, a position of the mirror 655 is set to either a solid-line position or a dotted-line position. Here, for example, when the mirror 655 is moved to the solid-line position in FIG. 79, the mirror 655 is set in a position retreating from the ultrasonic piezoelectric transducer 654. In this state, the ultrasonic probe 650 is inserted into the operative portion 610. Subsequently, when the ultrasonic probe 650 reaches a target portion, the probe is driven.

During driving of the ultrasonic probe 650, the ultrasonic wave outputted from the ultrasonic piezoelectric transducer 654 is radiated to all peripheries by 360 degrees via the ultrasonic transmitting cap 652. In this case, the ultrasonic wave reflected by the tumor portion 610*a* of the operative portion 610 is received by the sensor (not shown) of the ultrasonic probe 650 and transmitted to the ultrasonic observation apparatus 625. Thereby, the tomographic image of a horizontal direction in the tip end of the ultrasonic probe 650 is observed.

Here, the ultrasonic observation apparatus 625 analyzes the signal transmitted from the ultrasonic probe 650, processes the image, and displays the ultrasonic observation image. This ultrasonic observation image is displayed as the tumor tomographic image in the large screen display 633*a* of the microscope observation field 630*a* in FIG. 81. Additionally, the navigation image (three-directional tomographic image, respective sagital, coronal and axial tomographic image information, and three-dimensionally constructed image 3D prepared based on the information) is displayed in the small screen display 631*a* together with the microscope image L of the ultrasonic probe 650 in the microscope observation field 630*a*.

Figure 81:
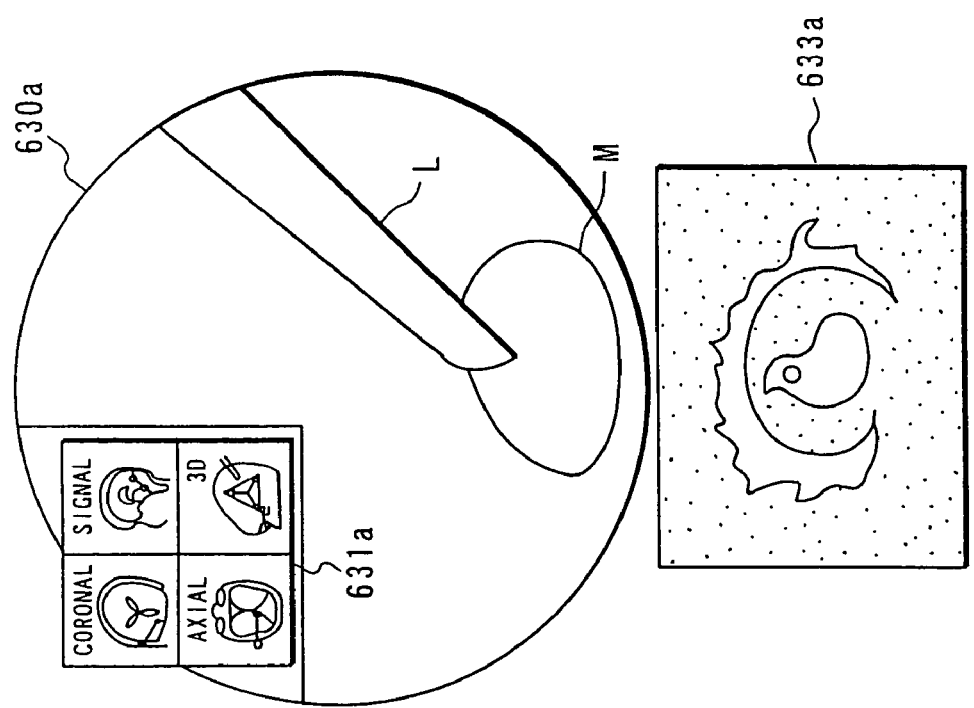
FIG. 81 is a diagram showing a first ultrasonic observation state of the seventeenth embodiment.

In FIG. 81, M denotes image information of a tumor tissue of a pathologically changed portion in the ultrasonic probe 650. An outer shape of the tumor portion is extracted, and superimposed on the microscope observation image. In this case, the tumor tissue can similarly be superimposed/displayed based on the preoperative diagnosis image using the navigation apparatus. On the other hand, the display in the image by the ultrasonic probe 650 includes a tumor tissue position change (brain shift) under operation, and the entire tumor image can be grasped correctly. Additionally, for the image information M of the tumor tissue of the pathologically changed portion, only a color Doppler image may be extracted/displayed in order to see a blood flow state.

Moreover, when the mirror 655 of the ultrasonic probe 650 is moved to the dotted-line position in FIG. 79, the mirror 655 is set in a position opposite to the ultrasonic piezoelectric transducer 654. In this state, the ultrasonic probe 650 is inserted into the operative portion 610. Subsequently, when the ultrasonic probe 650 reaches the target portion, the probe is driven.

Figure 82:
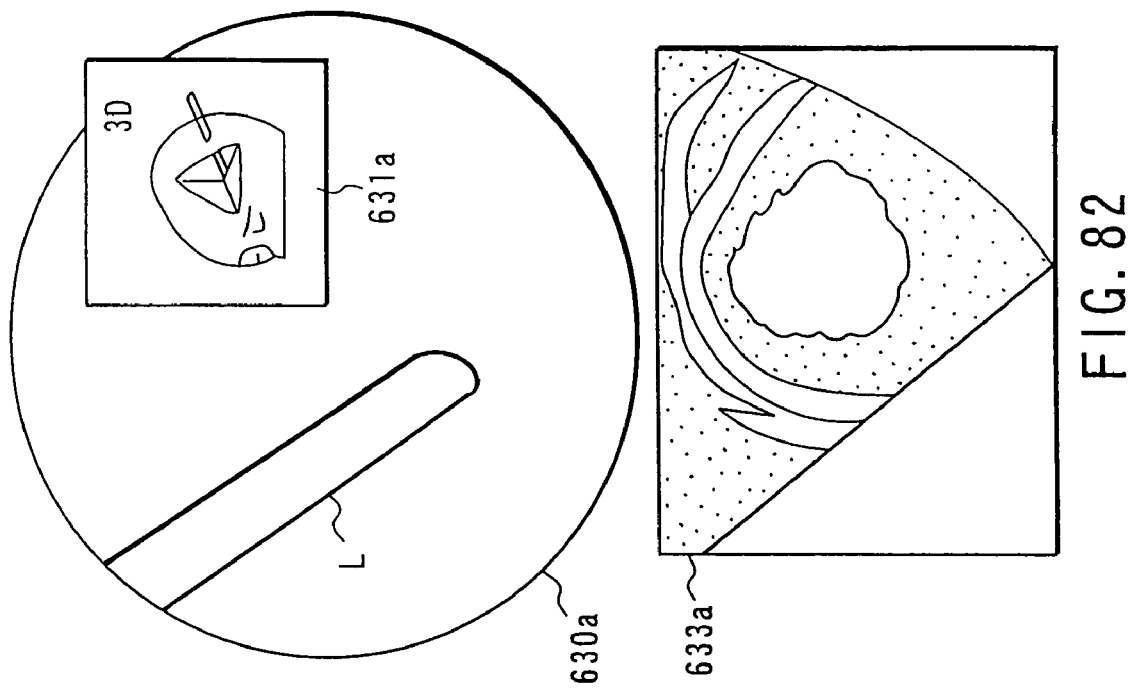
FIG. 82 is a diagram showing a second ultrasonic observation state of the seventeenth embodiment.

During driving of the ultrasonic probe 650, the ultrasonic wave outputted from the ultrasonic piezoelectric transducer 654 is reflected forward by the mirror 655, and radiated to the front of the ultrasonic transmitting cap 652. In this case, the ultrasonic wave reflected by the tumor portion 610*a* of the operative portion 610 is received by the sensor (not shown) of the ultrasonic probe 650 and transmitted to the ultrasonic observation apparatus 625. Subsequently, the ultrasonic observation apparatus 625 analyzes the signal transmitted from the ultrasonic probe 650, processes the image, and displays the tumor tomographic image in the large screen display 633*a* as shown in FIG. 82. Furthermore, the navigation image (three-dimensionally constructed image 3D) is displayed in the small screen display 631*a* together with the microscope image L of the ultrasonic probe 650 in the microscope observation field 630*a*.

Figure 83:
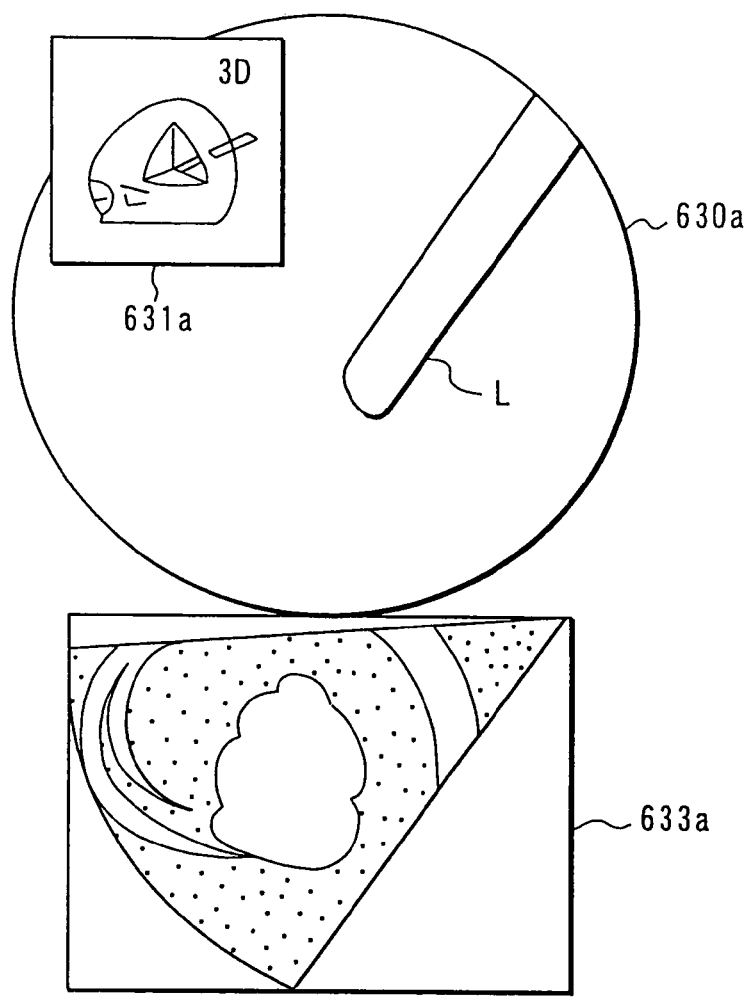
FIG. 83 is a diagram showing a third ultrasonic observation state of the seventeenth embodiment.

Moreover, when an image display direction is reversed by the image display direction display 656, as shown in FIG. 83, the direction of the tumor tomographic image displayed in the large screen display 633*a* can horizontally be changed. Therefore, when the ultrasonic probe 650 for observing the tomographic image of a front direction is used, the tomographic image is displayed in accordance with the insertion direction of the probe.

Therefore, according to the seventeenth embodiment, in addition to the effect similar to that of the operation microscope apparatus of the sixteenth embodiment, the image display direction can be changed in accordance with the insertion direction of the ultrasonic probe 650 for forward scanning. This facilitates recognition of the position of the ultrasonic image, and the operation can be securely carried out.

Figure 84:
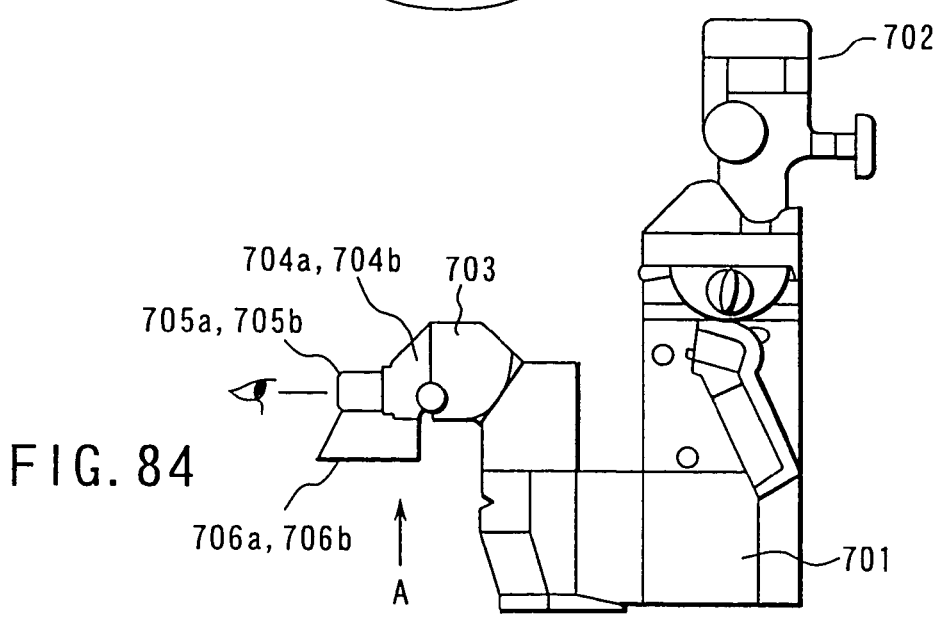
FIG. 84 is a constitution diagram of the entire microscope body section of the operation microscope according to an eighteenth embodiment of the present invention.
Figure 85:
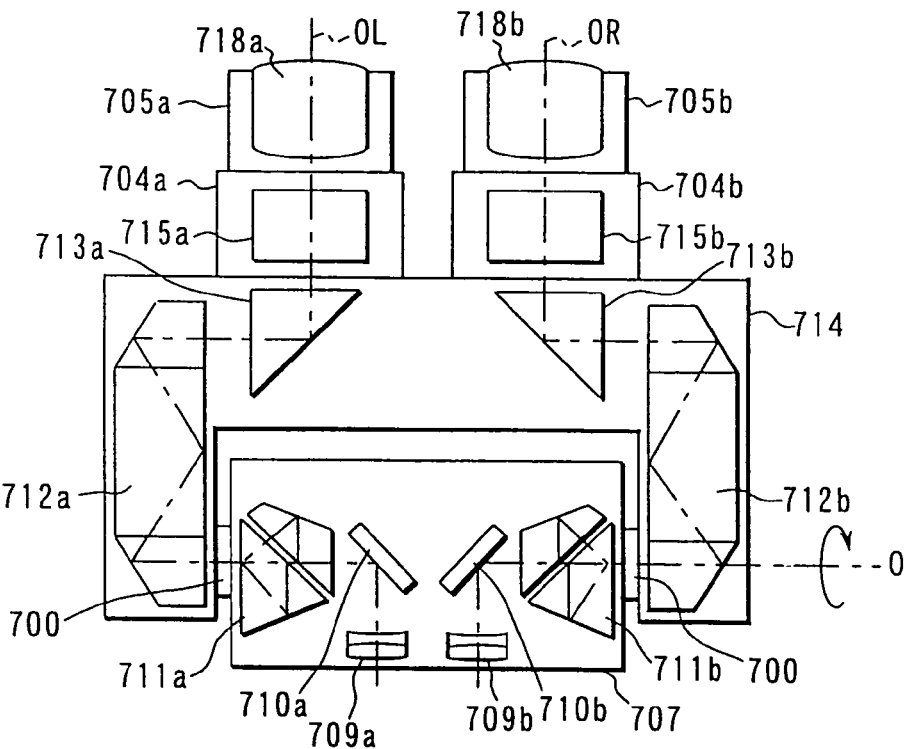
FIG. 85 is a diagram of a cross section as seen along arrow A in FIG. 84, showing an internal optical constitution of the binocular eyepiece lens tube of the eighteenth embodiment.
Figure 86:
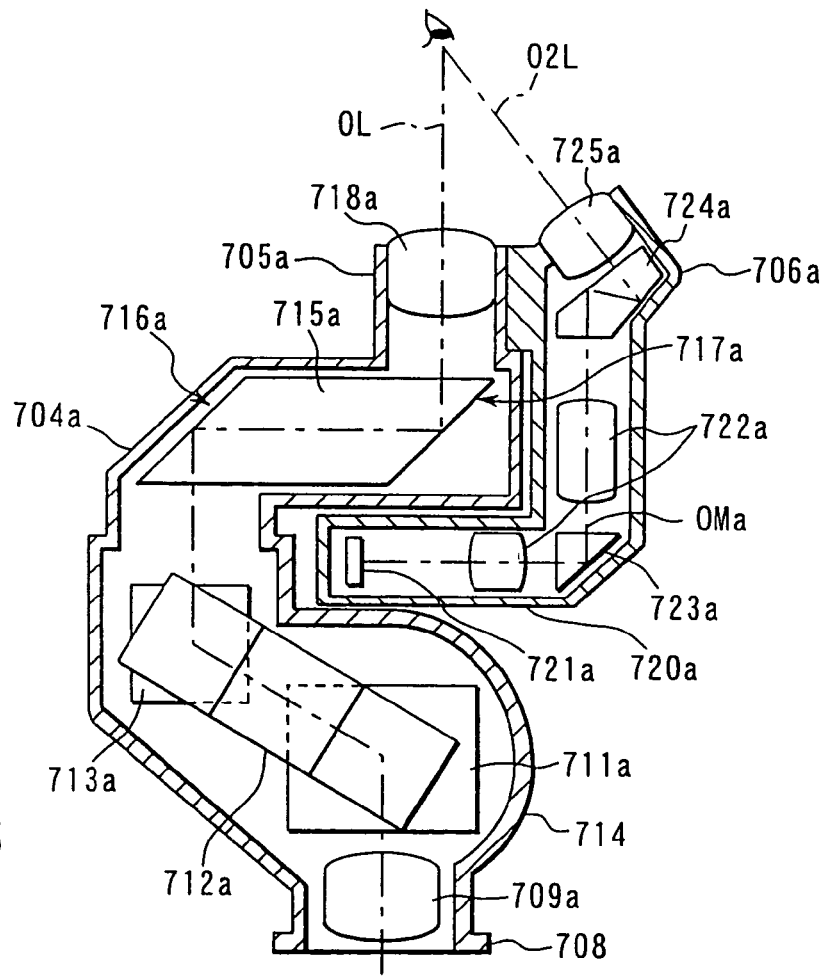
FIG. 86 is a side view showing a left side optical observation system of the operation microscope of the eighteenth embodiment.
Figure 87:
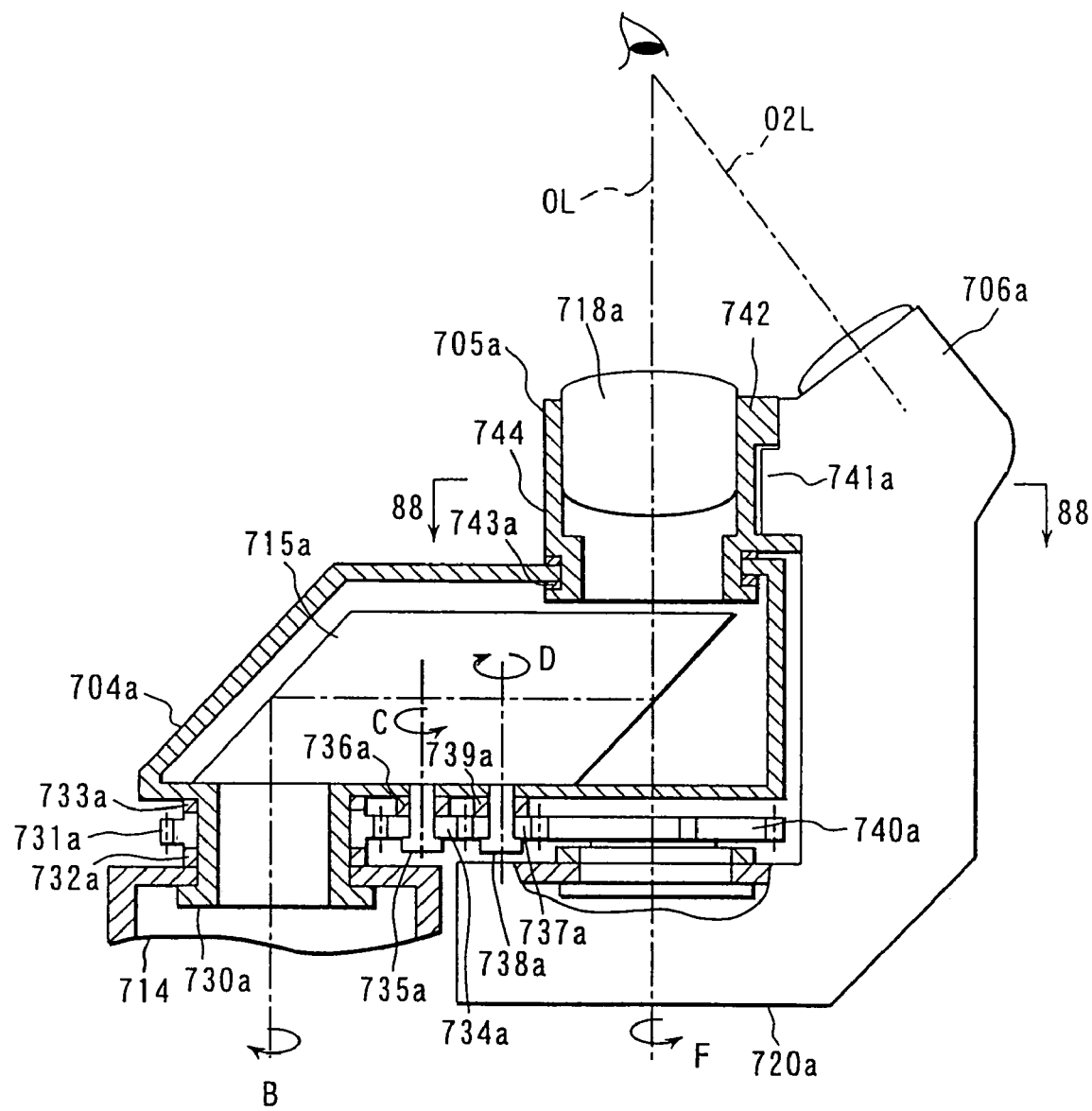
FIG. 87 is a longitudinal side sectional view of an eye distance adjustment mechanism of the binocular eyepiece lens tube in the operation microscope of the eighteenth embodiment.
Figure 88:
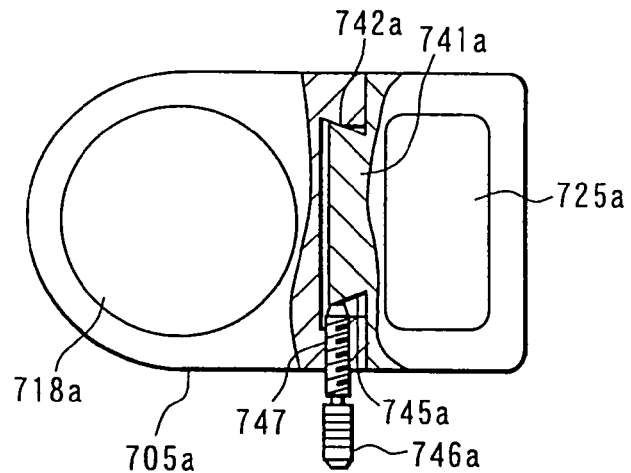
FIG. 88 is a sectional view taken along line 88-88 of FIG. 87.
Figure 89:
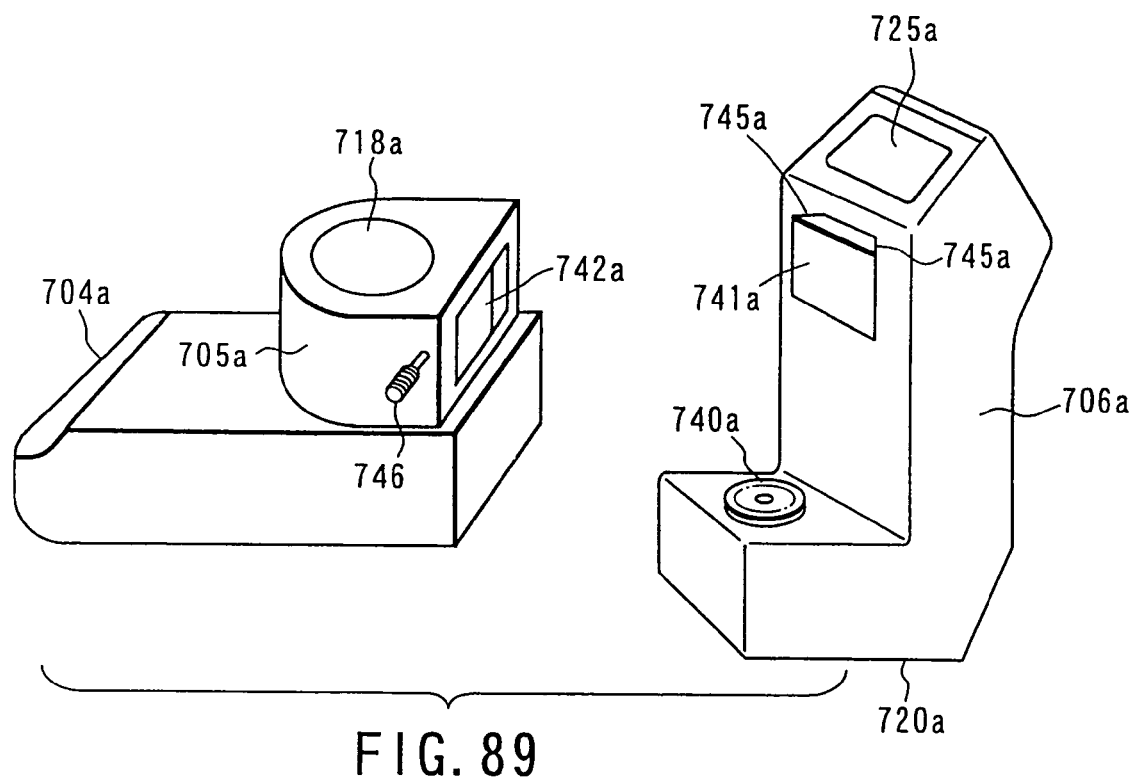
FIG. 89 is a perspective view showing a housing constitution of an eye distance adjustment section in the operation microscope of the eighteenth embodiment.
Figure 90:
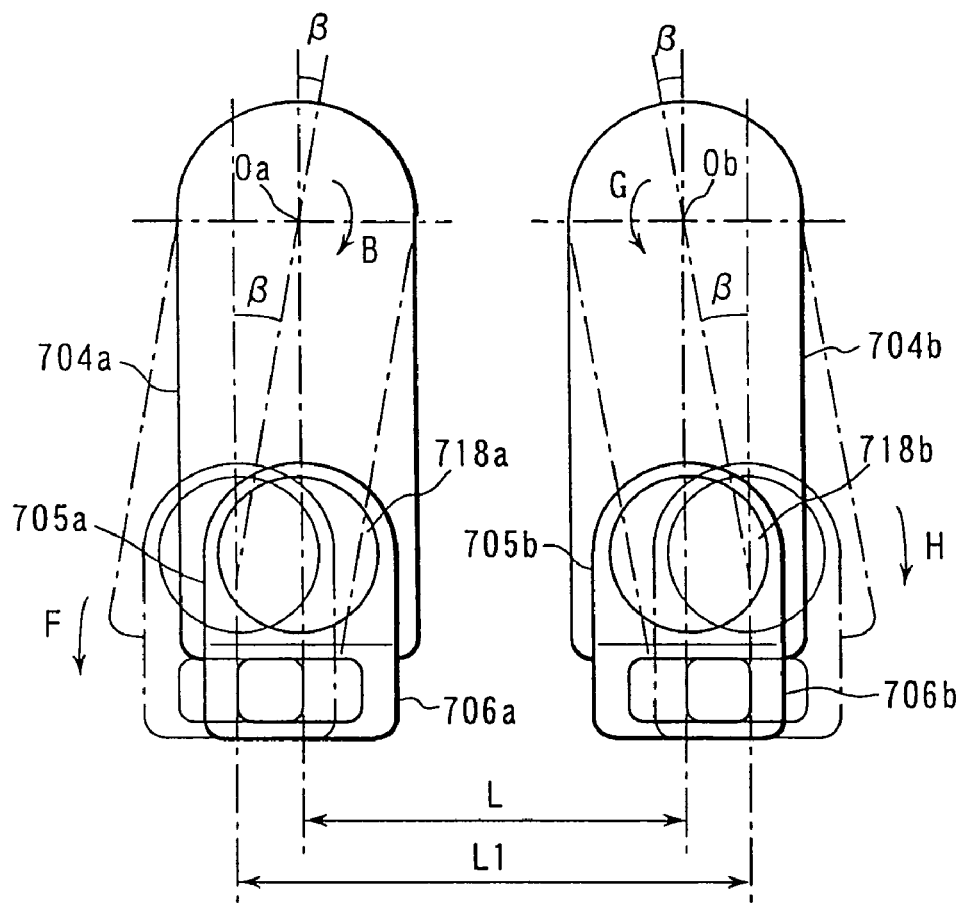
FIG. 90 is a diagram showing arrangement (movement) of an optical eyepiece system when eye distance adjustment is performed in the operation microscope of the eighteenth embodiment.
Figure 91:
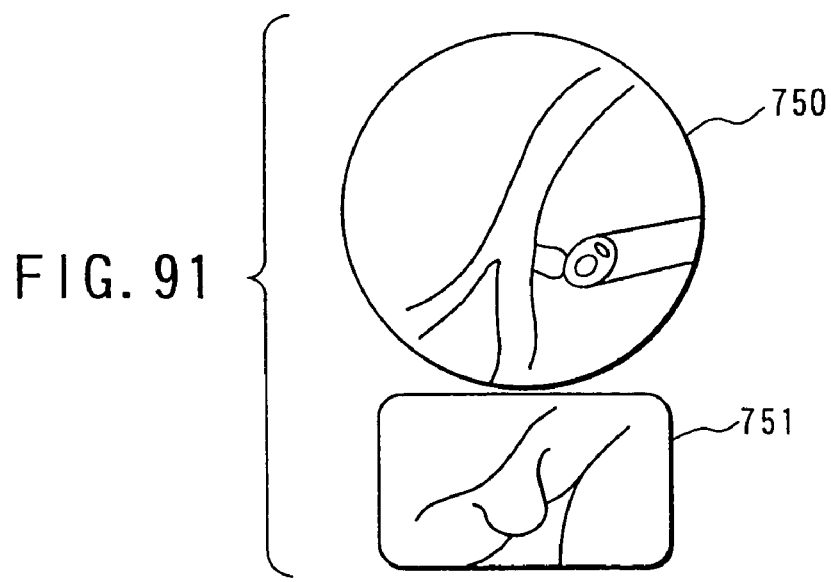
FIG. 91 is a diagram showing an image display state in the operation microscope observation field of the eighteenth embodiment.

FIG. 84 to FIG. 91 show an eighteenth embodiment. FIG. 84 is a constitution diagram of the entire microscope body of the operation microscope, FIG. 85 is a diagram of a binocular eyepiece lens tube as seen along arrow A in FIG. 84, showing an internal optical constitution of the tube, FIG. 86 is a side view showing a left side optical observation system in FIG. 85, FIG. 87 is a diagram showing details of an eye distance adjustment mechanism of the binocular eyepiece lens tube, FIG. 88 is a sectional view taken along line 88-88 of FIG. 87, FIG. 89 is a diagram showing a housing constitution of an eye distance adjustment section, FIG. 90 is a diagram showing arrangement (movement) of the optical eyepiece system when eye distance adjustment is performed, and FIG. 91 is a diagram showing an image display state in the observation field of the operation microscope.

An entire constitution of an operation microscope body 701 will be described with reference to FIG. 84. This operation microscope body 701 includes a pair of left and right optical observation systems. A tip end 702 of the operation microscope body 701 is attached to a stand arm (not shown), and can be disposed/fixed in a three-dimensionally free position.

Moreover, an eyepiece lens tube 703 is disposed in the operation microscope body 701. The eyepiece lens tube 703 similarly includes a pair of left and right optical systems for receiving left and right observation fluxes emitted from the microscope body 701. Furthermore, the eyepiece lens tube 703 is provided with a pair of left and right eye distance adjustment housings 704a, 704b including a parallel prism described later.

A pair of left and right first eyepiece housings 705a, 705b including a first optical eyepiece system described later are attached on an operating person's eye side of the eye distance adjustment housings 704a, 704b. Furthermore, in the constitution, a second pair of left and right eyepiece housings 706a, 706b including a second optical observation system described later can integrally be attached to the first eyepiece housings 705a, 705b.

A constitution of the eyepiece lens tube 703 will next be described with reference to FIG. 85 and FIG. 86. A fixed housing 707 is integrally attached to the microscope body 701 via a connection member 708. A pair of left and right image forming lenses 709a, 709b are disposed in the fixed housing 707. The image forming lenses 709a, 709b are optically connected to the optical observation system (not shown) of the microscope body 701. Moreover, the left and right observation fluxes emitted from the microscope body 701 are incident upon the image forming lenses 709a, 709b.

Furthermore, mirrors 710a, 710b for reflecting the fluxes incident through the image forming lenses 709a, 709b outwardly by 90° are disposed inside the image forming lenses 709a, 709b. Image rotator prisms 711a, 711b are disposed on outgoing light axes of the respective mirrors 710a, 710b.

Prisms 712a, 712b for reversing the opposite observation fluxes by 180° are disposed behind the image rotator prisms 711a, 711b. Furthermore, triangular prisms 713a, 713b are optically disposed/fixed behind the prisms. Additionally, the outgoing light axes from the respective prisms 712a, 712b are reflected in parallel to observation light axes OL, OR by the first optical eyepiece system described later by the triangular prisms 713a, 713b. These prisms 712a, 712b, and triangular prisms 713a, 713b are contained in a movable housing 714.

The movable housing 714 can rotate around an axis O, that is, incident light axes to the prisms 712a, 712b via a connection member 700. Moreover, the image rotator prisms 711a, 711b can rotate centering on the axis O by an angle of ½ of an angle of rotation of the movable housing 714 with respect to the fixed housing 707 by a cam mechanism (not shown).

Moreover, parallel prisms 715a, 715b are contained in the eye distance adjustment housings 704a, 704b. As shown in FIG. 86, the parallel prisms 715a, 715b include incident reflection surfaces 716a, 716b and outgoing reflection surfaces 717a, 717b. Furthermore, the fluxes from the outgoing reflection surfaces 717a, 717b of the respective parallel prisms 715a, 715b are led to a first pair of left and right optical eyepiece systems 718a, 718b contained in the respective eyepiece housings 705a, 705b. This constitutes the left and right observation light axes OL, OR of the microscope optical observation image observed by the first pair of left and right optical eyepiece systems 718a, 718b.

Moreover, the second optical observation system contained in the second eyepiece housings 706a, 706b (only one second eyepiece housing 706a is shown in FIG. 86) is constituted as follows. FIG. 86 shows only the left light path, but the right light path is similarly constituted. Bent sections 720a, 720b bent substantially in L shapes are formed in lower parts of the second eyepiece housings 706a, 706b. The bent sections 720a, 720b are disposed between the second eyepiece housings and the movable housing 714 disposed under the eye distance adjustment housings 704a, 704b.

Moreover, small-sized LCD monitors 721a, 721b are disposed in terminal ends of the respective bent sections 720a, 720b. The endoscope image is displayed as the electronic image in each of the small-sized LCD monitors 721a, 721b by control from a controller (not shown).

Furthermore, prisms 723a, 723b for reflecting outgoing light axes OMa, OMb from the LCD monitors 721a, 721b are disposed in connection sections with the respective bent sections 720a, 720b in the second eyepiece housings 706a, 706b. Additionally, optical relay systems 722a, 722b are disposed before and after respective prisms 723a, 723b on the outgoing light axes OMa, OMb from the LCD monitors 721a, 721b.

Moreover, prisms 724a, 724b for deflecting the light axes reflected by the prisms 723a, 723b in directions of the observation light axes OL, OR are disposed on upper ends of the second eyepiece housings 706a, 706b. Furthermore, second optical eyepiece systems 725a, 725b are optically disposed/connected on outgoing light axes O2L, O2R of the respective prisms 724a, 724b. Additionally, the observation light axes OL and O2L, or OR and O2R intersect each other in the vicinity of the emission pupil position.

A constitution of an eye distance adjustment mechanism will next be described with reference to FIG. 87. Only shows the left light path in FIG. 87, but the right light path is similarly constituted as described above. Here, a cylindrical member 730a is integrally attached to a lower end of the eye distance adjustment housing 704a. This cylindrical member 730a is attached to the fixed housing 714 so that the body can rotate around incident light axis O1 of the parallel prism 715a, and a so-called G ten top eye distance adjustment mechanism is constituted.

Moreover, a gear 731a is integrally attached to the cylindrical member 730a. Furthermore, washers 732a, 733a are attached on opposite sides of the gear 731a in an outer periphery of the cylindrical member 730a. Here, one washer 732a is inserted between the gear 731a and the movable housing 714, and the other washer 733a is inserted between the gear 731a and the eye distance adjustment housing 704a.

Moreover, a first idle gear 734a meshes with the gear 731a. The first idle gear 734a is supported so as to be rotatable around a shaft 735a attached to the eye distance adjustment housing 704a. Furthermore, a second idle gear 737a meshes with the first idle gear 734a. The second idle gear 737a is similarly supported to be rotatable around a shaft 738a attached to the eye distance adjustment housing 704a. Additionally, washers 736a, 739a are inserted between the idle gears 734a, 737a and the eye distance adjustment housing 704a, respectively.

Furthermore, a gear 740a is integrally attached to the bent section 720a of the second eyepiece housing 706a. The gear 740a meshes with the idle gear 737a.

Additionally, the gear 731a is constituted of the same number of teeth and modules as those of the gear 740a. That is, a transmission mechanism of a gear mechanism with a reduction ratio of 1 is constituted by the gears 731a, 740a and idle gears 734a, 737a.

Moreover, a connection portion 741a projects from a side portion of the second eyepiece housing 706a. The connection portion 741a is integrally connectable to a connection mount 742a of the first eyepiece housing 705a. Furthermore, while the connection portion 741a is connected to the connection mount 742a, a position relation is constituted such that a rotation center of the gear 740a agrees with the observation light axis OL of the first optical eyepiece system 718a.

Furthermore, a cylindrical member 743a is integrally disposed on a lower end of the first eyepiece housing 705a. A center axis of the cylindrical member 743a agrees with the observation light axis OL. Furthermore, a washer 744 is inserted between the first eyepiece housing 705a and the eye distance adjustment housing 704a around the cylindrical member 743a.

Additionally, as shown in FIG. 88, the connection portion 741a of the second eyepiece housing 706a is formed in a male dovetail sectional shape which is broadened toward a tip end and gradually narrowed toward a root side. Moreover, engaging slopes 745a are formed on opposite sides of the connection portion 741a.

Furthermore, a female dovetail shaped engagement groove corresponding to the male dovetail sectional shape of the connection portion 741a is formed in the connection mount 742a of the first eyepiece housing 705a. Moreover, a pressing pin 746 is attached to a side portion of the first eyepiece housing 705a. A male screw 747 is formed on a tip end of the pressing pin 746. Furthermore, the male screw 747 of the pressing pin 746 can be detachably attached to the slope 745a of the connection portion 741a.

Operation of the eighteenth embodiment will next be described. The operating person operates the stand arm (not shown) and disposes/fixes the microscope body 701 in a desired position. Furthermore, the movable housing 714 of the eyepiece lens tube 703 is rotated around the axis O, and the first optical eyepiece systems 718a, 718b are disposed in an operating person's eye positions. In this case, the image rotator prisms 711a, 711b in the fixed housing 707 of the eyepiece lens tube 703 are rotated by ½ with respect to the rotation of the movable housing around the axis O.

A light emitted from the operative portion is incident upon the image forming lenses 709a, 709b via an optical magnification system (not shown) in the microscope body 701. In this case, the left and right fluxes are passed through the image rotator prisms 711a, 711b, and, by the rotation of the movable housing 714 around the axis O, the rotation of the image is corrected. Thereafter, the fluxes are reflected by the triangular prisms 713a, 713b, passed through the parallel prisms 715a, 715b, and led to the first optical eyepiece systems 718a, 718b. The operating person performs stereoscopic observation at a desired enlargement magnification.

On the other hand, when the endoscope observation image, and the CT or MR image are simultaneously observed with the microscope observation image, the operating person operates a control unit (not shown), and displays the desired electronic image in the LCD monitors 721a, 721b. In this case, the lights emitted from the LCD monitors 721a, 721b are passed through the optical relay systems 722a, 722b. Furthermore, the light axes OMa, OMb are bent substantially in parallel to the observation light axes OL, OR by the prisms 723a, 723b. Subsequently, through the prisms 724a, 724b, light axes O2L, O2R forming an angle α with the observation light axes OL, OR are led to the second optical eyepiece systems 725a, 725b. Thereby, as shown in FIG. 91, the observation image by the second optical eyepiece systems 725a, 725b, that is, an electronic image 751 by the LCD monitor is displayed below an optical observation image 750 by the first optical eyepiece system 718a, 718b. The operating person can observe the electronic image similarly as the optical image only by turning the line of sight downward substantially by the angle of α without largely moving the face.

Subsequently, when the operating person observes the operative portion straight on, the person turns both eyes to a front side of the lens eyepiece tube 703 away from the first and second optical eyepiece systems 718a, 718b, 725a, 725b. In this case, the second optical observation systems contained in the second eyepiece housings 706a, 706b partially enter the lower parts of the eye distance adjustment housings 704a, 704b by the prisms 723a, 723b. Therefore, the operating person moves the face only to avoid the projections of the second eyepiece housings 706a, 706b, and observes the operative portion straight on.

Eye distance adjustment performed by the operating person to align the emission pupils of the eyepiece lens tube 703 with the operating person's left and right pupil positions will next be described. First, the operating person adjusts the distance between the observation light axes OL and OR to match their eyes by changing a distance between the left and right observation light axes OL and OR of the first optical eyepiece systems 718a, 718b to L1 from L in FIG. 90. In this case, the left and right eye distance adjustment housings 704a, 704b are rotated in the directions of arrows B and G. Then, the gear 731a of the left light path eye distance adjustment housing 704a similarly rotates in the direction B. A rotary force is applied to the gear 740a of the second eyepiece housing 706a in a direction of an arrow F successively via the first idle gear 734a and second idle gear 737a. Thereby, the first eyepiece housing 705a and second eyepiece housing 706a of the left light path are rotated by the same angle (β in FIG. 90) as that of the eye distance adjustment housing 704a in a direction of an arrow H centering on a center line Oa of the cylindrical member 730a.

Similarly, the first eyepiece housing 705b and second eyepiece housing 706b of the right light path are also rotated in the direction of the arrow H by the angle β. That is, parallel states of the first optical eyepiece systems 718a, 718b, and the second optical eyepiece systems 725a, 725b are held. The horizontal light axis interval is changed to L1 from L. Therefore, the operating person can observe both the microscope observation image and the electronic observation image with opposite eyes.

Subsequently, in a case in which the operating person requires no electronic image, when the male screw 747 of the pressing pin 746 disposed on the first eyepiece housing 705a is loosened, the pressure of the pressing pin 746 on the slope 745a of the connection portion 741a is released. Therefore, the connection portion 741a can be detached from the connection mount 742a, and the second eyepiece housing 706a can be detached from the first eyepiece housing 705a.

Moreover, similarly for the second eyepiece housing 706b of the right light path, when the male screw 747 of the pressing pin 746 is similarly loosened, the second eyepiece housing can be removed from the first eyepiece housing 705b. Therefore, in the case in which no electronic image is necessary, it is possible to observe the operative portion in an enlarged size with an operation feeling similar to that of the usual binocular eyepiece lens tube without being limited by the second eyepiece housings 706a, 706b.

Therefore, the following effect is achieved in the aforementioned constitution. That is, in the eighteenth embodiment, the second eyepiece housings 706a, 706b can easily be removed from the first eyepiece housings 705a, 705b as desired by the operating person. Therefore, it is easy to use only the first optical observation system as the usual optical observing observation lens tube.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An operation microscope apparatus comprising:
   a microscope body including an optical eyepiece system for stereoscopically observing an operative portion of a surgical operation;
   a microscope image observer for observing an observation image formed for stereoscopic observation by the microscope body;
   at least one image forming section for forming an image other than the observation image of the microscope image observer;
   an image display for displaying the image formed by the image forming section in said microscope image observer;
   display condition changing means for changing a display condition of the images displayed in the image display;
   an endoscope which forms an image source of the image other than the observation image;
   a holder for movably supporting the endoscope;
   a holder fixing section for releasably fixing a moving position of the holder; and
   detecting means for detecting a fixed/released state of the holder fixing section,
   wherein the display condition changing means causes the image display to display the image formed by the endoscope when the detecting means detects the released state of the holder fixing section, and causes the image display not to display the image formed by the endoscope when the detecting means detects the fixed state of the holder fixing section.

2. An operation microscope apparatus comprising:
   a microscope body including an optical eyepiece system for stereoscopically observing an operative portion of a surgical operation;
   a microscope image observer for observing an observation image formed for stereoscopic observation by the microscope body;
   a plurality of image forming sections for forming images other than the observation image of said microscope image observer;
   an image display for selectively displaying the respective images of said plurality of image forming sections in said microscope image observer;
   a display driver for controlling display states of the plurality of images formed by said plurality of image forming sections independently of one another;
   a controller for controlling an operation of the display driver;
   an endoscope which forms an image source of the image other than the observation image;
   a holder for moveably supporting the endoscope; and
   a holder fixing section for releasably fixing a moving position of the holder, wherein said display driver comprises:
      an image selector for selecting respective display images of said plurality of image forming sections;
      a display controller for displaying the image selected by said image selector in said corresponding image display; and
      an operation input section for operating said display controller and the image selectors, the operation input section comprising:
         an automatic controller for automatically controlling at least one of said display controller and said image selector; and
         detecting means for detecting a fixed/released state of the holder fixing section;
         wherein the automatic controller causes the image display to display the image formed by the endoscope when the detecting means detects the released state of the holder fixing section, and causes the image display not to display the image formed by the endoscope when the detecting means detects the fixed state of the holder fixing section.

3. The operation microscope apparatus according to claim 2, wherein said image display comprises:
   an in-field image display which displays an image of one of said plurality of image forming sections in a field of the observation image of the microscope image observer; and
   an out-of-field image display which displays an image of another of said plurality of image forming sections out of the field of the observation image of the microscope image observer,
   wherein said image display changes a display mode of a plurality of display images of said in-field display in accordance with a state of said holder fixing section.

4. The operation microscope apparatus according to claim 3,
   wherein the image forming section comprises an endoscope image forming section for forming an observation image by an endoscope;
   wherein when the holder moves, an image of the endoscope is displayed in the field of the observation image of the microscope image observer, and the observation image of the endoscope is displayed in the in-field image display, and the out-of-field image display is kept in a non-display state, and when the holder is fixed, the image of the endoscope is displayed in the field of the observation image of the microscope image observer, and the observation image of the endoscope is displayed in the out-of-field image display, and the in-field image display changes the display mode to a state in which a non-display state is maintained.

* * * * *